(12) United States Patent
Bagrodia et al.

(10) Patent No.: US 10,071,100 B2
(45) Date of Patent: Sep. 11, 2018

(54) THERAPEUTIC NANOPARTICLES COMPRISING A THERAPEUTIC AGENT AND METHODS OF MAKING AND USING THE SAME

(71) Applicant: PFIZER INC., New York, NY (US)

(72) Inventors: Shubha Bagrodia, San Diego, CA (US); Jennifer Lafontaine, San Diego, CA (US); Zach Lovatt, Belmont, MA (US); Eyoung Shin, Marlborough, MA (US); Young Ho Song, Natick, MA (US); Greg Troiano, Pembroke, MA (US); Hong Wang, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/860,881

(22) Filed: Jan. 3, 2018

(65) Prior Publication Data
US 2018/0125854 A1 May 10, 2018

Related U.S. Application Data

(63) Continuation of application No. 14/656,899, filed on Mar. 13, 2015, now Pat. No. 9,895,378.

(60) Provisional application No. 61/953,628, filed on Mar. 14, 2014.

(51) Int. Cl.
| | | |
|---|---|---|
| *A61K 9/16* | (2006.01) | |
| *A61K 31/5377* | (2006.01) | |
| *A61K 9/51* | (2006.01) | |
| *A61K 9/107* | (2006.01) | |
| *A61K 47/34* | (2017.01) | |
| *A61K 47/28* | (2006.01) | |
| *A61K 47/12* | (2006.01) | |

(52) U.S. Cl.
CPC ........ *A61K 31/5377* (2013.01); *A61K 9/1075* (2013.01); *A61K 9/5153* (2013.01); *A61K 47/12* (2013.01); *A61K 47/28* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 5,302,401 A | 4/1994 | Liversidge | |
| 5,543,158 A | 8/1996 | Gref | |
| 5,563,122 A | 10/1996 | Endo | |
| 5,578,325 A | 11/1996 | Domb | |
| 5,766,635 A | 6/1998 | Spenleuhauer | |
| 6,007,845 A | 12/1999 | Domb | |
| 6,136,846 A | 10/2000 | Rubinfeld | |
| 6,139,870 A | 10/2000 | Verrecchia | |
| 6,201,072 B1 | 3/2001 | Rathi | |
| 6,254,890 B1 | 7/2001 | Hirosue | |
| 6,265,609 B1 | 7/2001 | Jackson | |
| 6,395,718 B1 | 5/2002 | Slusher | |
| 6,346,274 B1 | 12/2002 | Koll | |
| 6,528,499 B1 | 3/2003 | Kozikowski | |
| 6,841,547 B2 | 1/2005 | Brown | |
| 6,875,886 B2 | 4/2005 | Frangioni | |
| 6,890,946 B2 | 5/2005 | Nakshatri | |
| 6,890,950 B2 | 5/2005 | Boothman | |
| 6,899,898 B2 | 5/2005 | Albayrak | |
| 6,902,743 B1 | 6/2005 | Setterstrom | |
| 6,916,788 B2 | 7/2005 | Seo | |
| 7,422,902 B1 | 9/2008 | Wheeler | |
| 7,687,071 B1 | 3/2010 | Heger | |
| 8,003,128 B2 | 8/2011 | Kreuter | |
| 8,034,765 B2 | 10/2011 | De | |
| 8,039,469 B2 | 10/2011 | Venkatesan | |
| 8,206,747 B2 | 6/2012 | Zale | |
| 8,211,473 B2 | 7/2012 | Troiano | |
| 8,217,036 B2 | 7/2012 | Venkatesan | |
| 8,236,330 B2 | 8/2012 | Zale | |
| 8,246,968 B2 | 8/2012 | Zale | |
| 8,273,363 B2 | 9/2012 | Zale | |
| 8,293,276 B2 | 10/2012 | Troiano | |
| 8,318,208 B1 | 11/2012 | Zale | |
| 8,318,211 B2 | 11/2012 | Zale | |
| 8,357,401 B2 | 1/2013 | Troiano | |
| 8,367,113 B2 | 2/2013 | Gu | |
| 8,420,123 B2 | 4/2013 | Troiano | |
| 8,518,963 B2 | 8/2013 | Ali | |
| 8,563,041 B2 | 10/2013 | Grayson | |
| 8,575,159 B2 | 11/2013 | Venkatesan | |
| 8,603,534 B2 | 12/2013 | Zale | |

(Continued)

FOREIGN PATENT DOCUMENTS

| | | |
|---|---|---|
| CN | 1957911 | 5/2007 |
| CN | 1961864 | 5/2007 |

(Continued)

OTHER PUBLICATIONS

Pinkerton et al, (Mol Pharmaceutics 10:319-328 available online Dec. 24, 2012) (Year: 2012).*

Foss, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, (Sep. 7-10, 2005) (1 page).

Fournier et al., "Experimental studies and preliminary clinical trial of vinorelbine-loaded polymeric bioresorbable implants for the local treatment of solid tumors," Cancer Research, 51(19):5384-5391 (1991).

(Continued)

*Primary Examiner* — Craig D Ricci
(74) *Attorney, Agent, or Firm* — David Rubin

(57) ABSTRACT

The present disclosure generally relates to nanoparticles comprising a substantially hydrophobic acid and a therapeutic agent (1-(4-{[4-(dimethylamino)piperidin-1-yl]carbonyl}phenyl)-3-[4-(4,6-dimorpholin-4-yl-1,3,5-triazin-2-yl)phenyl]urea), or pharmaceutically acceptable salts thereof, and a polymer. Other aspects include methods of making and using such nanoparticles.

3 Claims, 13 Drawing Sheets

(56) References Cited

U.S. PATENT DOCUMENTS

| | | |
|---|---|---|
| 8,603,535 B2 | 12/2013 | Troiano |
| 8,609,142 B2 | 12/2013 | Troiano |
| 8,613,951 B2 | 12/2013 | Zale |
| 8,613,954 B2 | 12/2013 | Zale |
| 8,617,608 B2 | 12/2013 | Zale |
| 8,623,417 B1 | 1/2014 | Zale |
| 8,637,083 B2 | 1/2014 | Troiano |
| 8,652,528 B2 | 2/2014 | Troiano |
| 8,663,700 B2 | 3/2014 | Troiano |
| 8,709,483 B2 | 4/2014 | Farokhzad |
| 8,748,421 B2 | 6/2014 | Venkatesan |
| 8,859,542 B2 | 10/2014 | Venkatesan |
| 2002/0045582 A1 | 4/2002 | Margolin |
| 2002/0119916 A1 | 8/2002 | Hassan |
| 2003/0068377 A1 | 4/2003 | Fowers |
| 2003/0143184 A1 | 7/2003 | Seo |
| 2003/0232887 A1 | 12/2003 | Johnson |
| 2003/0235619 A1 | 12/2003 | Allen |
| 2004/0054190 A1 | 3/2004 | Pomper |
| 2004/0071768 A1 | 4/2004 | Sarris |
| 2004/0081688 A1 | 4/2004 | Del Curto |
| 2004/0086544 A1 | 5/2004 | Bezemer |
| 2004/0096477 A1 | 5/2004 | Chauhan |
| 2004/0185170 A1 | 9/2004 | Chungi |
| 2004/0219224 A1 | 11/2004 | Yakovlevsky |
| 2004/0220081 A1 | 11/2004 | Kreitz |
| 2004/0247624 A1 | 12/2004 | Unger |
| 2004/0247680 A1 | 12/2004 | Farokhzad |
| 2005/0037075 A1 | 2/2005 | Farokhzad |
| 2005/0037086 A1 | 2/2005 | Tyo |
| 2005/0063976 A1 | 3/2005 | Schultes |
| 2005/0123617 A1 | 6/2005 | Chang |
| 2005/0136258 A1 | 6/2005 | Nie |
| 2005/0142205 A1 | 6/2005 | Rashba-Step |
| 2005/0201972 A1 | 9/2005 | Seo |
| 2005/0256071 A1 | 11/2005 | Davis |
| 2005/0266067 A1 | 12/2005 | Sengupta |
| 2006/0002852 A1 | 1/2006 | Saltzman |
| 2006/0002971 A1 | 1/2006 | Saltzman |
| 2006/0034925 A1 | 2/2006 | Au |
| 2006/0057219 A1 | 3/2006 | Nagasaki |
| 2006/0110460 A1 | 5/2006 | Ferret |
| 2006/0165987 A1 | 7/2006 | Hildgen |
| 2007/0031402 A1 | 2/2007 | Zhang |
| 2007/0041901 A1 | 2/2007 | Diener |
| 2007/0043066 A1 | 2/2007 | Sum |
| 2007/0053845 A1 | 3/2007 | Sengupta |
| 2007/0154554 A1 | 7/2007 | Burgermeister |
| 2008/0057102 A1 | 3/2008 | Roorda |
| 2008/0124400 A1 | 5/2008 | Liggins |
| 2008/0193381 A1 | 8/2008 | Babich |
| 2008/0267876 A1 | 10/2008 | Benita |
| 2009/0022806 A1 | 1/2009 | Mousa |
| 2009/0053293 A1 | 2/2009 | Liang |
| 2009/0053315 A1 | 2/2009 | Brough |
| 2009/0061009 A1 | 3/2009 | Schwarz |
| 2009/0074753 A1 | 3/2009 | Lynch |
| 2009/0074828 A1 | 3/2009 | Alexis |
| 2009/0155326 A1 | 6/2009 | Mack |
| 2009/0155349 A1 | 6/2009 | Heller |
| 2009/0170753 A1 | 7/2009 | Welz |
| 2009/0196933 A1 | 8/2009 | De |
| 2009/0247552 A1 | 10/2009 | Sawa |
| 2009/0306120 A1 | 12/2009 | Lim |
| 2009/0312402 A1 | 12/2009 | Contag |
| 2009/0317479 A1 | 12/2009 | Ishihara |
| 2010/0008998 A1 | 1/2010 | Kang |
| 2010/0015050 A1 | 1/2010 | Panyam |
| 2010/0040537 A1 | 2/2010 | Gu |
| 2010/0087337 A1 | 4/2010 | Dewitt |
| 2010/0104645 A1 | 4/2010 | Ali |
| 2010/0166866 A1 | 7/2010 | Fischer |
| 2010/0216804 A1 | 8/2010 | Zale |
| 2010/0303723 A1 | 12/2010 | Farokhzad |
| 2010/0303900 A1 | 12/2010 | Ramstack |
| 2010/0316725 A1 | 12/2010 | Ryde |
| 2011/0125090 A1 | 5/2011 | Peyman |
| 2011/0159079 A1 | 6/2011 | Li |
| 2011/0200677 A1 | 8/2011 | Chandran |
| 2011/0217377 A1 | 9/2011 | Zale |
| 2011/0275704 A1 | 11/2011 | Troiano |
| 2011/0294717 A1 | 12/2011 | Ali |
| 2012/0276162 A1 | 11/2012 | Zale |
| 2013/0034608 A1 | 2/2013 | Zale |
| 2013/0101672 A1 | 4/2013 | Cheng |
| 2013/0108668 A1 | 5/2013 | Figueiredo |
| 2013/0115293 A1 | 5/2013 | Sabnis |
| 2013/0172406 A1 | 7/2013 | Zale |
| 2013/0189315 A1 | 7/2013 | Zale |
| 2013/0230568 A1 | 9/2013 | Troiano |
| 2013/0236500 A1 | 9/2013 | Zale |
| 2013/0243827 A1 | 9/2013 | Troiano |
| 2013/0243863 A1 | 9/2013 | Troiano |
| 2013/0302433 A1 | 11/2013 | Troiano |
| 2014/0030351 A1 | 1/2014 | Zale |
| 2014/0093579 A1 | 4/2014 | Zale |
| 2014/0142165 A1 | 5/2014 | Grayson |
| 2014/0178475 A1 | 6/2014 | Figueiredo |
| 2014/0186452 A1 | 7/2014 | Figueiredo |
| 2014/0186453 A1 | 7/2014 | Zale |
| 2014/0248358 A1 | 9/2014 | Figueiredo |
| 2014/0249158 A1 | 9/2014 | Figueiredo |
| 2014/0308363 A1 | 10/2014 | Zale |
| 2014/0356443 A1 | 12/2014 | Brisander et al. |

FOREIGN PATENT DOCUMENTS

| | | |
|---|---|---|
| CN | 1969816 | 5/2007 |
| CN | 1969818 | 5/2007 |
| CN | 101053553 | 10/2007 |
| CN | 101396340 | 4/2009 |
| CN | 101396342 | 4/2009 |
| CN | 101433520 | 5/2009 |
| EA | 011594 | 12/2007 |
| EP | 0805678 | 11/1997 |
| EP | 1985309 | 10/2008 |
| EP | 2106806 | 10/2009 |
| JP | H10-194995 | 7/1998 |
| JP | 2006131577 | 5/2006 |
| JP | 2006321763 | 11/2006 |
| KR | 10-0418916 | 3/2002 |
| KR | 20020041712 | 6/2002 |
| RU | 2007140909 | 5/2009 |
| WO | 1989000846 | 2/1989 |
| WO | 1994028874 | 12/1994 |
| WO | 1995003357 | 2/1995 |
| WO | 1995035097 | 12/1995 |
| WO | 1997041837 | 11/1997 |
| WO | 2000000222 | 1/2000 |
| WO | 2000019996 | 4/2000 |
| WO | 2001087345 | 11/2001 |
| WO | 2002045689 | 6/2002 |
| WO | 2002080846 | 10/2002 |
| WO | 2002098885 | 12/2002 |
| WO | 2003017987 | 3/2003 |
| WO | 2003032906 | 4/2003 |
| WO | 2003055469 | 7/2003 |
| WO | 2003086369 | 10/2003 |
| WO | 2004060059 | 7/2004 |
| WO | 2004084871 | 10/2004 |
| WO | 2004089291 | 10/2004 |
| WO | 2005009357 | 2/2005 |
| WO | 2005020989 | 3/2005 |
| WO | 2005046572 | 5/2005 |
| WO | 2006093991 | 9/2006 |
| WO | 2007024323 | 3/2007 |
| WO | 2007028341 | 3/2007 |
| WO | 2007034479 | 3/2007 |
| WO | 2007074604 | 7/2007 |
| WO | 2007110152 | 10/2007 |
| WO | 2007133807 | 11/2007 |
| WO | 2008016602 | 2/2008 |
| WO | 2008019142 | 2/2008 |
| WO | 2008051245 | 5/2008 |

(56) References Cited

FOREIGN PATENT DOCUMENTS

| WO | 2008058192 | | 5/2008 | | |
|---|---|---|---|---|---|
| WO | 2008105773 | | 9/2008 | | |
| WO | 2008109163 | | 9/2008 | | |
| WO | 2008121949 | | 10/2008 | | |
| WO | 2008124632 | | 10/2008 | | |
| WO | 2008124634 | | 10/2008 | | |
| WO | 2008124639 | | 10/2008 | | |
| WO | 2008139804 | | 11/2008 | | |
| WO | 2009070302 | | 6/2009 | | |
| WO | 2009074274 | | 6/2009 | | |
| WO | 2009084801 | | 7/2009 | | |
| WO | 2009121631 | | 10/2009 | | |
| WO | 2009143313 | | 11/2009 | | |
| WO | 2010005721 | | 1/2010 | | |
| WO | 2010005723 | | 1/2010 | | |
| WO | 2010005725 | | 1/2010 | | |
| WO | 2010005726 | | 1/2010 | | |
| WO | WO 2010/005721 | * | 1/2010 | ............... | A61K 9/16 |
| WO | 2010068866 | | 6/2010 | | |
| WO | 2010075072 | | 7/2010 | | |
| WO | 2010114768 | | 10/2010 | | |
| WO | 2010114770 | | 10/2010 | | |
| WO | 2010117668 | | 10/2010 | | |
| WO | 2011072218 | | 6/2011 | | |
| WO | 2011079279 | | 6/2011 | | |
| WO | 2011084513 | | 7/2011 | | |
| WO | 2011084518 | | 7/2011 | | |
| WO | 2011084521 | | 7/2011 | | |
| WO | 2011119995 | | 9/2011 | | |
| WO | 2012040513 | | 3/2012 | | |
| WO | 2012054923 | | 4/2012 | | |
| WO | 2012166923 | | 12/2012 | | |
| WO | 2013044219 | | 3/2013 | | |
| WO | 2013127490 | | 9/2013 | | |
| WO | 2014043618 | | 3/2014 | | |
| WO | 2014043625 | | 3/2014 | | |
| WO | 2014210485 | | 12/2014 | | |

OTHER PUBLICATIONS

Galsky et al., "Cabazitaxel" Nature Reviews, 9(9):677-678 (2010).
Gao et al., "In vivo cancer targeting and imaging with semiconductor quantum dots," Nature Biotechnology, 22 (8):969-976 (2004).
Gill et al., "Modulated differential scanning calorimetry," Journal of Thermal Analysis, 40:931-939 (1993).
Govender et al., "Defining the drug incorporation properties of PLA-PEG nanoparticles," International Journal of Pharmaceutics, 199(1):95-110 (2000).
Govender et al., "PLGA nanoparticles prepared by nanoprecipitation: drug loading and release studies of a water soluble drug," Journal of Controlled Release, 57(2):171-185 (1999).
Gref et al., "'Stealth' corona-core nanoparticles surface modified by polyethylene glycol (PEG): influences of the corona (PEG chain length and surface density) and of the core composition on phagocytic uptake and plasma protein adsorption," Colloids and Surfaces B: Biointerfaces, 18(3-4):301-313 (2000).
Gref et al., "Biodegradable long-circulating polymeric nanospheres," Science, 263(5153):1600-1603 (1994).
Gref et al., "Development and characterization of CyA-loaded poly(lactic acid)-poly(ethylene glycol)PEG micro- and nanoparticles. Comparison with conventional PLA particulate carriers," European Journal of Pharmaceutics and Biopharmaceutics, 51(2):111-118 (2001).
Gross, "Oral pH-modified release budesonide for treatment of inflammatory bowel disease, collagenous and lymphocytic colitis," Expert Opinion on Pharmacotherapy, 9(7):1257-1265 (2008).
Gu et al., "Precise engineering of targeted nanoparticles by using self-assembled biointegrated block copolymers", PNAS, 105(7):2586-2591 (2008).
Heald et al., "Poly(lactic acid)-Poly(ethylene oxide) (PLA-PEG) nanoparticles: NMR studies of the central solidlike PLA core and the liquid PEG corona," Langmuir. 18:3669-3675 (2002).
Hederstrom et al., "Purification and surface modification of polymeric nanoparticles for medical applications," Masters Thesis. SINTEF Materials and Chemistry, Trondheim, Norway, Mar. 3, 2008 (95 pages).
Heldman et al., "Paclitaxel stent coating inhibits neointimal hyperplasia at 4 weeks in a porcine model of coronary restenosis," Circulation, 103(18):2289-2295 (2001).
Hrkach et al., "Preclinical development and clinical translation of a PSMA-targeted Docetaxel nanoparticle with a differentiated pharmacological profile," Science Translational Medicine, 4(128):1-11 (2012).
Humblet et al., "An HPLC/mass spectrometry platform for the development of multimodality contrast agents and targeted therapeutics: prostate-specific membrane antigen small molecule derivatives," Contrast Media and Molecular Imaging, 1(5):196-211 (2006).
Humblet et al., "High-affinity near-infrared fluorescent small-molecule contrast agents for in vivo imaging of prostate-specific membrane antigen," Molecular Imagining, 4(4):448-462 (2005).
Jayaprakash et al., "Design and synthesis of a PSMA inhibitor-doxorubicin conjugate for targeted prostate cancer therapy," ChemMedChem, 1(3)299-302 (2006).
Jenning et al., "Characterisation of a novel solid lipid nanoparticle carrier system based on binary mixtures of liquid and solid lipids," International Journal of Pharmaceutics, 199(2):167-177 (2000).
Jeong et al., "Effect of cryoprotectants on the reconstitution of surfactant-free nanoparticles of poly(DL-lactide-co-glycolide)," Journal of Microencapsulation, 22(6):593-601 (2005).
Jiang et al., "Preparation of PLA and PLGA nanoparticles by binary organic solvent diffusion method," Journal of Central South University of Technology, 10(3):202-206 (2003).
Kimura et al., "Local delivery of imatinib mesylate (STI571)-incorporated nanoparticle ex vivo suppresses vein graft neointima formation," Cancer Research, 118(14 Suppl):S65-70 (2008).
Koziara et al., "Blood compatibility of cetyl alcohol/polysorbate-based nanoparticles," Pharmaceutical Research, 22 (11):1821-1828 (2005).
Kozikowski et al., "Design of remarkably simple, yet potent urea-based inhibitors of glutamate carboxypeptidase II (NAALADase)," Journal of Medicinal Chemistry, 44(3):298-301 (2001).
Kozikowski et al., "Synthesis of urea-based inhibitors as active site probes of glutamate carboxypeptidase II: efficacy as analgesic agents," Journal of Medicinal Chemistry, 47(7):1729-1738 (2004).
Kwon, "Long acting porous microparticle for pulmonary protein delivery," International Journal of Pharmaceutics, 333 (1-2):5-9 (2007).
Lewis "Hawley's Condensed Chemical Dictionary, 15th ed.," Wiley-Interscience entries for "acid," "base," "dissociation constant," "partition coefficient," and "pK," pp. 16, 127, 472, 947, and 998 (2007) (7 pages).
Li et al., "Post-operative imatinib in patients with intermediate or high risk gastrointestinal stromal tumor," European Journal of Surgical Oncology, 37(4):319-324 (2011).
Liao et al., "Comparison of nine programs predicting pK(a) values of pharmaceutical substances," Journal of Chemical Information and Modeling, 49(12):2801-2812 (2009).
Lyseng-Williamson et al., "Docetaxel: a review of its use in metastatic breast cancer," Drugs, 65(17):2513-16 (2005).
Majer et al., "Synthesis and biological evaluation of thiol-based inhibitors of glutamate carboxypeptidase II: discovery of an orally active GCP II inhibitor," Journal of Medicinal Chemistry, 46(10):1989-1996 (2003).
Mallon et al., "Antitumor efficacy of PKI-587, a highly potent dual PI3K/mTOR kinase inhibitor," Clinical Cancer Research, 17(10):3193-203 (2011).
Maresca et al., "A series of halogenated heterodimeric inhibitors of prostate specific membrane antigen (PSMA) as radiolabeled probes for targeting prostate cancer," Journal of Medicinal Chemistry, 52(2):347-357 (2009).
Matsumoto et al., "Preparation of nanoparticles consisted of poly(L-lactide)-poly(ethylene glycol)-poly(L-lactide) and their evaluation in vitro," International Journal of Pharmaceutics, 185(1):93-101 (1999).

(56) References Cited

OTHER PUBLICATIONS

Mease et al., "N-[N-[(S)-1,3-Dicarboxypropyl]carbamoyl]-4-[18F]fluorobenzyl-L-cysteine, [18F]DCFBC: a new imaging probe for prostate cancer," Clinical Cancer Research, 14(10):3036-3043 (2008).
Merck (Betamethasone, Merck Index (Knovel, copyright 2006, 2012) (retrieved May 28, 2013 from www.knovel.com/web/portal/knovel_content?p_p_id=EST_NOVEL_CONTENT&p_p_action=) (3 pages).
Misra et al., "Production of multimeric prostate-specific membrane antigen small-molecule radiotracers using a solid-phase 99mTc preloading strategy," Journal of Nuclear Medicine, 48(8)1379-1389 (2007).
Murugesan et al., "Pegylated poly(lactide-co-glycolide (PLGA) nanoparticulate delivery of Docetaxel: synthesis of diblock copolymers, optimization of Preparation variables on formulation characteristics and in vitro release studies." Journal of Biomedical Nanotechnology, 3(9):52-60 (2007).
Musumeci et al., "Lyoprotected nanosphere formulations for paclitaxel controlled delivery," Journal for Nanoscience and Nanotechnology, 6(9-10):3118-3125 (2006).
Musumeci et al., "PLA/PLGA nanoparticles for sustained release of docetaxel," International Journal of Pharmaceutics, 325(1-2):172-179 (2006).
Ojer, "Spray-drying of poly(anhydride) nanoparticles for drug/antigen delivery," Journal of Drug Delivery Science and Technology, 20(5):353-359 (2010).
Okassa et al., "Optimization of iron oxide nanoparticles encapsulation within poly(D,L-lactide-co-glycolide) sub-micron particles," European Journal of Pharmaceutics and Biopharmaceutics, 67(1):31-8 (2007).
Oliver et al., "Conformational and SAR analysis of NAALADase and PSMA inhibitors," Bioorganic and Medicinal Chemistry, 11(20):4455-4461 (2003).
Olivier, "Drug transport to brain with targeted nanoparticles," Journal of the American Society for Experimental NeuroTherapeutics, 2(1):108-119 (2005).
Omelczuk et al., "The influence of polymer glass transition temperature and molecular weight on drug release from tablets containing poly(DL-lactic acid)," Pharmaceutical Research, 9(1):26-32 (1992).
PCT International Preliminary Report on Patentability for Application No. PCT/US2010/060575, dated Jun. 19, 2012 (WO 2011/084521) (11 pages).
PCT International Search Report and Written Opinion for Application No. PCT/US2014/044617, dated Oct. 3, 2014 (WO 2014/210485) (2 pages).
PCT International Search Report for Application No. PCT/US2008/013158, dated Feb. 17, 2009 (WO 2009/070302) (2 pages).
PCT International Search Report for Application No. PCT/US2008/058873, dated Aug. 28, 2008 (WO 2008/121949) (3 pages).
PCT International Search Report for Application No. PCT/US2009/047513, dated Jan. 18, 2010 (WO 2010/005721) (3 pages).
PCT International Search Report for Application No. PCT/US2009/047515, dated Jan. 19, 2010 (WO 2010/005723) (3 pages).
PCT International Search Report for Application No. PCT/US2009/047517 dated Mar. 2, 2010 (WO 2010/005725).
PCT International Search Report for Application No. PCT/US2009/047518, dated Mar. 5, 2010 (WO 2010/005726) 3 pages).
PCT International Search Report for Application No. PCT/US2009/067672, dated Aug. 23, 2010 (WO 2010/068866) (3 pages).
PCT International Search Report for Application No. PCT/US2009/068028, dated Aug. 23, 2010 (WO 2010/075072) (3 pages).
PCT International Search Report for Application No. PCT/US2010/059879, dated Aug. 30, 2011 (WO 2011/072218) (4 pages).
PCT International Search Report for Application No. PCT/US2010/060564, dated Sep. 29, 2011 (WO 2011/084513) (4 pages).
PCT International Search Report for Application No. PCT/US2010/060570, dated Aug. 25, 2011 (WO 2011/084518) (14 pages).
PCT International Search Report for Application No. PCT/US2010/060575, dated Aug. 25, 2011 (WO 2011/084521) (4 pages).
PCT International Search Report for Application No. PCT/US2011/057498, dated May 10, 2012 (WO 2012/054923) (5 pages).
PCT International Search Report for Application No. PCT/US2012/040215, dated Nov. 16, 2012 (WO 2012/166923) (19 pages).
PCT International Search Report for Application No. PCT/US2012/056891, dated Jan. 4, 2013 (WO 2013/044219) (4 pages).
PCT International Search Report for Application No. PCT/US2013/059936, dated Feb. 4, 2014 (WO 2014/043618 ) (8 pages).
PCT International Search Report for Application No. PCT/US2013/059949, dated Jan. 2, 2014 (WO 2014/043625) (5 pages).
Peracchia et al., "PEG-coated nanospheres from amphiphilic diblock and multiblock copolymers: investigation of their drug encapsulation and release characteristics," Journal of Controlled Release, 46(3):223-231 (1996).
Pomper et al., Department of Radiology and Radiological Science, Johns Hopkins University, "New developments in molecular imaging of prostate cancer," Topical Symposium on: Advanced Molecular Imaging Techniques in the Detection, Diagnosis, Therapy, and Follow-up of Prostate Cancer, Palazzo Barberini, Rome, Dec. 6, 2005 (45 pages).
Pourcelle et al., "PCL-PEG-based nanoparticles grafted with GRGDS peptide: preparation and surface analysis by XPS," Biomacromolecules, 8(12):3977-3983 (2007).
Pulkkinen et al., "Three-step tumor targeting of paclitaxel using biotinylated PLA-PEG nanoparticles and avidin-biotin technology: formulation development and in vitro anticancer activity", European Journal of Pharmaceutics and Biopharmaceutics, 70(1):66-74 (2008).
Ren et al., "Preparation and characterization of magnetic PLA-PEG composite nanoparticles for drug targeting," Reactive and Functional Polymers, 66(9):944-951 (2006).
Riley et al., "Colloidal stability and drug incorporation aspects of micellar-like PLA-PEG nanoparticles," Colloids and Surfaces B: Biointerfaces, 16(1-4):147-59 (1999).
Sapra et al., "Ligand-targeted liposomal anticancer drugs," Progress in Lipid Research, 42(5):439-462 (2003).
Senthilkumar et al., "Long circulating PEGylated poly(D,L-lactide-co-glycolide) nanoparticulate delivery of Docetaxel to solid tumors," Journal of Drug Targeting, 16(5):424-435 (2008).
Stolnik et al., "Polylactide-poly(ethylene glycol) micellar-like particles as potential drug carriers: production, colloidal properties and biological performance," Journal of Drug Targeting, 9(5):361-378 (2001).
Sweetman, "Martindale: The Complete Drug Reference," 33rd ed., Pharmaceutical Press, entry for Docetaxel, p. 534 (2002).
Takacs-Novak et al., "Ion-pair partition of quarternary ammonium drugs: the influence of counter ions of different lipophilicity, size, and flexibility," Pharmaceutical Research, 16(10):1633-1638 (1999).
Tamilvanan et al., "Manufacturing techniques and excipients used during the design of biodegradable polymer-based microspheres containing therapeutic peptide/protein for parenteral controlled drug delivery," PDA Journal of Pharmaceutical Science and Technology, 62(2):125-154 (2008).
Tang et al., "Prostate targeting ligands based on N-acetylated alpha-linked acidic dipeptidase," Biochemical and Biophysical Research Communications, 307(1):8-14 (2003).
Taxotere Dosage, [retrieved on Mar. 28, 2013] http://www.drugs.com/dosage/taxotere.html (7 pages).
Tobio et al., "Stealth PLA-PEG nanoparticles as protein carriers for nasal administration," Pharmaceutical Research, 15(2):270-275 (1998).
Toxnet database "Chemical/Physical Properties" for "Oleic Acid," "Dodecanoic Acid," "Procaine," "Sunitinib," and "Vincristine," pp. 1-22 (retrieved on Sep. 3, 2014 from <http://toxnet.nlm.nih.gov/>.
Van Vlerken et al., "Multi-functional polymeric nanoparticles for tumour-targeted drug delivery," Expert Opinion on Drug Delivery, 3(2):205-216 (2006).

(56) References Cited

OTHER PUBLICATIONS

Verrecchia et al., "Non-stealth (poly(lactic acid/albumin)) and stealth (poly(lactic acid-polyethylene glycol)) nanoparticles as injectable drug carriers," Journal of Controlled Release, 36(1-2):49-61 (1995).
Vicari et al., "Paclitaxel loading in PLGA nanospheres affected the in vitro drug cell accumulation and antiproliferative activity," BMC Cancer, 8:212 (2008) (11 pages).
Yamamoto et al., "Long-circulating poly(ethylene glycol)-poly(D,L-lactide) block copolymer micelles with modulated surface charge," Journal of Controlled Release, 77(1-2):27-38 (2001).
Yoo et al., "Protein-fatty acid complex for enhanced loading and stability within biodegradable nanoparticles," Journal of Pharmaceutical Sciences, 90(2):194-201 (2001).
Zhang et al., "Neointimal Hyperplasia Persists at Six Months after Sirolimus-Eluting Stent Implantation in Diabetic Porcine," Cardiovascular Diabetology, 6(16):1-7 (2007).
Zhou et al., "NAAG peptidase inhibitors and their potential for diagnosis and therapy," Nature Reviews Drug Discovery, 4:1015-1026 (2005).
Venkatesan et al., "Bis(morpholino-1,3,5-triazine) derivatives: potent adenosine 5'-triphosphate competitive phosphatidylinositol-3-kinase/mammalian target of rapamycin inhibitors: discovery of compound 26 (PKI-587), a highly efficacious dual inhibitor," Journal of Medicinal Chemistry, 53(6)2636-2645 (2010).
Chio et al., "Hydrophobic Ion Pair Formation between Leuprolide and Sodium Oleate for Sustained Release from Biodegradable Polymeric Microspheres," International Journal of Pharmaceutics, 203(1-2):193-202 (1998).
Gutali et al., "Lipophilic Drug Derivatives in Liposomes," International Journal of Pharmaceutics, 165:129-168 (1998).
Mackay et al., "Physical-Chemical Properties and Environmental Fate for Organic Chemicals," Taylor & Francis, Chapter 13, carboxylic acids, pp. 2688-2778 (2006).
Merck Index Online, Royal Society of Chemistry, entry for "Imatinib", pp. 1-2 (2013).
Meyer et al., "Hydrophobic Ion Pairing: Altering the Solubility Properties of Biomolecules," Pharmaceutical Research, 15(2):188-193 (1998).
Pinkerton et al., "Formation of Stable Nanocarriers by in Situ Ion Pairing During Block-Copolymer-Directed Rapid Precipitation," Molecular Pharmaceutics, 10(1):319-328 (2013).
www.selleckchem.com, PF-05212384 (PKI-587), (published on website on Feb. 4, 2013).
Battalia et al., "Methotrexate-loaded SLNs prepared by coacervation technique: in vitro cytotoxicity and in vivo pharacokinetics and biodistribution," Nanomedicine, 6(9): 1561-1573, 2011—Abstract Only.
Abdelwahed et al., "Freeze-drying of nanoparticles: formulation, process and storage considerations," Advanced Drug Delivery Reviews, 58(15):1688-1713 (2006).
Abizaid et al., "Sirolimus-Eluting Stents Inhibit Neointimal Hyperplasia in Diabetic Patients," European Heart Journal, 25(2):104-112 (2006).
Adams et al., "Amphiphilic block copolymers for drug delivery," Journal of Pharmaceutical Sciences, 92(7):1343-1355 (2003).
Altmann, "Epothilone B and its analogs—a new family of anticancer agents," Mini-Reviews in Medicinal Chemistry 3 (2):149-158 (2003); Abstract Only [retrieved from Bentham Science, < URL: http://www.eurekaselect.com/80911/article>] (1 page).
Avgoustakis, "Pegylated poly(lactide) and poly(lactide-co-glycolide) nanoparticles: preparation, properties and possible applications in drug delivery," Current Drug Delivery, 1(4):321-333 (2004).
Barinka et al., "Structural insight into the pharmacophore pocket of human glutamate carboxypeptidase II," Journal of Medicinal Chemistry, 50(14):3267-3273 (2007).
Barinka et al., "Interactions between human glutamate carboxypeptidase II and urea-based inhibitors: structural characterization," Journal of Medicinal Chemistry, 51(24):7737-7743 (2008).

Bilati et al., "Nanoprecipitation versus emulsion-based techniques for the encapsulation of proteins into biodegradable nanoparticles and process-related stability issues," AAPS PharmSciTech, 6(4):E594-E604 (2005).
Blindt et al., "A novel drug-eluting stent coated with an integrin-binding cyclic Arg-Gly-Asp peptide inhibits neointimal hyperplasia by recruiting endothelial progenitor cells," Journal of the American College of Cardiology, 47(9):1786-1795 (2006).
Caliceti et al., "Effective protein release from PEG/PLA nanoparticles produced by compressed gas anti-solvent precipitation techniques," Journal of Controlled Release, 94(1):195-205 (2004).
Chandran et al., "Characterization of a targeted nanoparticle functionalized with a urea-based inhibitor of prostate-specific membrane antigen (PSMA)," Cancer Biology and Therapy, 7(6):974-982 (2008).
Chen et al., "Radiohalogenated prostate-specific membrane antigen (PSMA)-based ureas as imaging agents for prostate cancer," Journal of Medicinal Chemistry, 51(24):7933-7943 (2008).
Cheng et al., "Formulation of functionalized PLGA-PEG nanoparticles for in vivo targeted drug delivery," Biomaterials, 28(5):869-876 (2007).
Clinical Trials, "A Study of BIND-014 Given to Patients with Advanced or Mestastatic Cancer," Apr. 30, 2013 [retrieved on Sep. 5, 2014] Retrieved from the internet <URL:http://clinicaltrials.gov/archive/NCT01300533/2013_04_30> (4 pages).
Dancey, "Therapeutic targets: mTOR and related pathways," Cancer Biology and Therapy, 5(9):1065-1073 (2006).
Davaran, "Preparation and in vitro evaluation of linear and star-branched PLGA nanoparticles for insulin delivery," Journal of Bioactive and Compatible Polymers, 23(2):115-131 (2008).
De Jaeghere et al., "Freeze-drying and lyopreservation of diblock and triblock poly(lactic acid)-poly(ethylene oxide) (PLA-PEO) copolymer nanoparticles," Pharmaceutical Development and Technology, 5(4):473-483 (2000).
De Jaeghere et al., "Formulation and lyoprotection of poly(lactic acid-co-ethylene oxide) nanoparticles: influence on physical stability and in vitro cell uptake," Pharmaceutical Research, 16(6):859-866 (1999).
Docetaxel Dosage, [retrieved on Mar. 28, 2013] http://www.drugs.com/dosage/docetaxel.html (7 pages).
Dong et al., "Methoxy poly(ethylene glycol)-poly(lactide) (MPEG-PLA) nanoparticles for controlled delivery of anticancer drugs," Biomaterials, 25(14):2843-2849 (2004).
Dong et al., "In vitro and in vivo evaluation of methoxy polyethylene glycol-polylactide (MPEG-PLA) nanoparticles for small-molecule drug chemotherapy," Biomaterials, 28(28)4154-4160 (2007).
Dorati et al., "Polyethylenglycol-co-poly-D,L-lactide copolymer based microspheres: preparation, characterization and delivery of a model protein," Journal of Microencapsulation, 25(5):330-338 (2008).
Eurasian Official Action for EA201170038, dated Aug. 12, 2013 (2 pages).
Eurasian Official Action for EA201170040, dated Jun. 29, 2012 (2 pages).
Eurasian Search Report for Application No. EA201100765, dated Aug. 2, 2013 (4 pages).
Eurasian Search Report for Application No. EA201170038, dated Jul. 8, 2011 (2 pages).
Eurasian Search Report for Application No. EA201170039, dated Nov. 21, 2011 (4 pages).
Eurasian Search Report for Application No. EA201290497, dated Jan. 15, 2013 (3 pages).
European Examination Report for EP09794913.5, dated Jul. 16, 2012 (8 pages).
European Extended Search Report for Application No. EP 10842557.0, dated Jul. 8, 2013 (11 pages).
European Extended Search Report for Application No. EP 11835279.8, dated Feb. 28, 2014 (8 pages).
European Extended Search Report for Application No. EP 13162786.1, dated Aug. 30, 2013 (7 pages).
European Extended Search Report for Application No. EP09794913.5 dated Jul. 8, 2011 (10 pages).

(56) References Cited

OTHER PUBLICATIONS

European Extended Search Report for Application No. EP09794913.5, dated Jul. 4, 2013 (9 pages).
European Extended Search Report for Application No. EP09794915.0, dated Jan. 25, 2012 (8 pages).
European Extended Search Report for Application No. EP09794917.6, dated Aug. 7, 2013 (8 pages).
European Extended Search Report for Application No. EP09835578.7, dated May 18, 2012 (8 pages).
European Extended Search Report for Application No. EP10836748.3, dated Mar. 21, 2013 (11 pages).
European Extended Search Report for Application No. EP10842554.7, dated Jul. 10, 2013 (9 pages).
European Extended Search Report for Application No. EP10842556.2, dated Jul. 8, 2013 (9 pages).
European Extended Search Report for Application No. EP11186037.5, dated Mar. 2, 2012 (6 pages).
European Extended Search Report for Application No. EP13162789.5, dated Aug. 30, 2013 (6 pages).
European Extended Search Report for Application No. EP14150948.9, dated Jul. 8, 2014 (8 pages).

Ewesuedo et al., "Chapter 1: Systemically Administered Drugs," Drug Delivery Systems in Cancer Therapy, Ed. D. M. Brown, Totowa:Humana, pp. 3-14 (2003) (12 pages).
Faivre et al., "Molecular basis for sunitinib efficacy and future clinical development," Nature Reviews Drug Discovery, 6(9):734-745 (2007).
Farokhzad et al., "Nanoparticle-aptamer bioconjugates for cancer targeting," Expert Opinion on Drug Delivery, (3):311-324 (2006).
Farokhzad et al., "Nanoparticle-aptamer bioconjugates: a new approach for targeting prostate cancer cells," Cancer Research, 64(21):7668-7672 (2004).
Farokhzad et al., "Targeted nanoparticle-aptamer bioconjugates for cancer chemotherapy in vivo," PNAS, 103 (16):6315-6320 (2006).
Feng et al., "Nanoparticles of biodegradable polymers for clinical administration of paclitaxel," Current Medicinal Chemistry, 11(4):413-424 (2004).
Foss et al., "Radiolabeled small-molecule ligands for prostate-specific membrane antigen: in vivo imaging in experimental models of prostate cancer," Clinical Cancer Research, 11(11):4022-4028 (2005).

* cited by examiner

THERAPEUTIC NANOPARTICLES COMPRISING A THERAPEUTIC AGENT AND METHODS OF MAKING AND USING THE SAME

CROSS-REFERENCE TO RELATED APPLICATIONS

This application is a Continuation of U.S. Non-Provisional application Ser. No. 14/656,899 filed on Mar. 13, 2015, now allowed, which claims the benefit of U.S. provisional application 61/953,628, filed on Mar. 14, 2014, which is incorporated by reference herein in its entirety.

BACKGROUND

Systems that deliver certain drugs to a patient (e.g., targeted to a particular tissue or cell type or targeted to a specific diseased tissue but not normal tissue) or that control release of drugs have long been recognized as beneficial.

For example, therapeutics that include an active drug and that are, e.g., targeted to a particular tissue or cell type or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach.

Therapeutics that offer controlled release and/or targeted therapy also must be able to deliver an effective amount of drug, which is a known limitation in other nanoparticle delivery systems. For example, it can be a challenge to prepare nanoparticle systems that have an appropriate amount of drug associated with each nanoparticle, while keeping the size of the nanoparticles small enough to have advantageous delivery properties.

Therapeutic agents containing at least one basic nitrogen atom (i.e., protonatable nitrogen-containing therapeutic agents) represent an important group of therapeutic agents. However, nanoparticle formulations of this class of drugs are often hindered by undesirable properties, e.g., unfavorable burst release profiles and poor drug loading.

Accordingly, a need exists for nanoparticle therapeutics and methods of making such nanoparticles that are capable of delivering therapeutic levels of protonatable nitrogen-containing therapeutic agents to treat diseases such as cancer, while also reducing patient side effects.

SUMMARY

The present invention relates to a therapeutic nanoparticle of the therapeutic drug, 1-(4-{[4-(dimethylamino)piperidin-1-yl]carbonyl}phenyl)-3-[4-(4,6-dimorpholin-4-yl-1,3,5-triazin-2-yl)phenyl]urea or pharmaceutically acceptable salts thereof. More specifically, the present invention relates to a therapeutic nanoparticle comprising 1-(4-{[4-(dimethylamino)piperidin-1-yl]carbonyl}phenyl)-3-[4-(4,6-dimorpholin-4-yl-1,3,5-triazin-2-yl)phenyl]urea or pharmaceutically acceptable salts thereof and further comprising a substantially hydrophobic acid. Additionally, the present invention relates to a therapeutic nanoparticle comprising 1-(4-{[4-(dimethylamino)piperidin-1-yl]carbonyl}phenyl)-3-[4-(4,6-dimorpholin-4-yl-1,3,5-triazin-2-yl)phenyl]urea or pharmaceutically acceptable salts thereof, a substantially hydrophobic acid, and a polymer selected from diblock poly(lactic) acid-poly(ethylene)glycol copolymer, a diblock poly(lactic acid-co-glycolic acid)-poly(ethylene)glycol copolymer and combination thereof, wherein the therapeutic nanoparticle comprises about 10 to about 30 weight percent poly(ethylene)glycol. The present invention also relates to a pharmaceutical composition comprising such nanoparticles, including a plurality of such nanoparticles, and a pharmaceutically acceptable excipient. In addition, the present invention relates to a therapeutic nanoparticle comprising about 0.05 to about 30 weight percent of a substantially hydrophobic acid, about 0.2 to about 25 weight percent of 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof and about 50 to about 99.75 weight percent of a copolymer selected from diblock poly(lactic) acid-poly(ethylene)glycol copolymer, a diblock poly(lactic acid-co-glycolic acid)-poly(ethylene)glycol copolymer and combination thereof, wherein the therapeutic nanoparticle comprises about 10 to about 30 weight percent poly(ethylene)glycol, as well as a pharmaceutical composition comprising the therapeutic nanoparticle and a and a pharmaceutically acceptable excipient. The present invention also relates to a therapeutic nanoparticle comprising about 0.05 to about 30 weight percent of a substantially hydrophobic acid, about 0.2 to about 20 weight percent of 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof and about 50 to about 99.75 weight percent of a copolymer selected from diblock poly(lactic) acid-poly(ethylene)glycol copolymer, a diblock poly(lactic acid-co-glycolic acid)-poly(ethylene)glycol copolymer and combination thereof, wherein the therapeutic nanoparticle comprises about 10 to about 30 weight percent poly(ethylene)glycol, as well as a pharmaceutical composition comprising the therapeutic nanoparticle and a and a pharmaceutically acceptable excipient.

Described herein are polymeric nanoparticles that include the therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof. This compound is basic and it is a protonatable nitrogen-containing therapeutic agent, as defined herein below. Also described herein are methods of making and using such therapeutic nanoparticles.

In one aspect, a therapeutic nanoparticle is provided. In this aspect, the therapeutic nanoparticle comprises about 0.05 to about 30 weight percent of a substantially hydrophobic acid, about 0.2 to about 25 weight percent of 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof, wherein the $pK_a$ of the protonated form of the therapeutic agent is at least about 1.0 $pK_a$ units greater than the $pK_a$ of the hydrophobic acid, and about 50 to about 99.75 weight percent of a copolymer selected from diblock poly(lactic) acid-poly(ethylene)glycol copolymer, a diblock poly(lactic acid-co-glycolic acid)-poly(ethylene)glycol copolymer and combination thereof, wherein the therapeutic nanoparticle comprises about 10 to about 30 weight percent poly(ethylene)glycol. In one embodiment, the therapeutic nanoparticle comprises about 0.05 to about 30 weight percent of a substantially hydrophobic acid, about 0.2 to about 20 weight percent of 1-(4-{[4-(dimethylamino)piperidin-1-yl]carbonyl}phenyl)-3-[4-

(4,6-dimorpholin-4-yl-1,3,5-triazin-2-yl)phenyl]urea or a pharmaceutically acceptable salt thereof, wherein the $pK_a$ of the protonated form of the therapeutic agent is at least about 1.0 $pK_a$ units greater than the $pK_a$ of the hydrophobic acid, and about 50 to about 99.75 weight percent of a copolymer selected from diblock poly(lactic) acid-poly(ethylene)glycol copolymer, a diblock poly(lactic acid-co-glycolic acid)-poly(ethylene)glycol copolymer and combination thereof, wherein the therapeutic nanoparticle comprises about 10 to about 30 weight percent poly(ethylene)glycol.

In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of about 1:7 (therapeutic agent:PLA-PEG). In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of about 1:5 (therapeutic agent:PLA-PEG). In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of about 1:4 (therapeutic agent:PLA-PEG). In certain embodiments, the therapeutic nanoparticle comprises 1-(4-{[4-(dimethylamino)piperidin-1-yl]carbonyl}phenyl)-3-[4-(4,6-dimorpholin-4-yl-1,3, 5-triazin-2-yl)phenyl]urea and PLA-PEG (in a 16:5 molar ratio) in a weight ratio of about 1:14 (therapeutic agent:PLA-PEG). In certain embodiments, the therapeutic nanoparticle comprises 1-(4-{[4-(dimethylamino)piperidin-1-yl]carbonyl}phenyl)-3-[4-(4,6-dimorpholin-4-yl-1,3, 5-triazin-2-yl)phenyl]urea and PLA-PEG (in a 16:5 molar ratio) in a weight ratio of about 1:3 (therapeutic agent:PLA-PEG).

In another aspect, the therapeutic nanoparticle comprises a substantially hydrophobic acid, wherein the molar ratio of the substantially hydrophobic acid to the aforementioned therapeutic agent ranges from about 0.25:1 to about 2:1, about 0.2 to about 25 weight percent of the aforementioned therapeutic agent, wherein the $pK_a$ of the protonated therapeutic agent is at least about 1.0 $pK_a$ units greater than the $pK_a$ of the hydrophobic acid, and about 50 to about 99.75 weight percent of a polymer selected from diblock poly(lactic) acid-poly(ethylene)glycol copolymer, diblock poly(lactic acid-co-glycolic acid)-poly(ethylene)glycol copolymer and combination thereof, wherein the therapeutic nanoparticle comprises about 10 to about 30 weight percent poly(ethylene)glycol. In one embodiment, the therapeutic nanoparticle comprises a substantially hydrophobic acid, wherein the molar ratio of the substantially hydrophobic acid to the aforementioned therapeutic agent ranges from about 0.25:1 to about 2:1, about 0.2 to about 20 weight percent of the aforementioned therapeutic agent, wherein the $pK_a$ of the protonated therapeutic agent is at least about 1.0 $pK_a$ units greater than the $pK_a$ of the hydrophobic acid, and about 50 to about 99.75 weight percent of a polymer selected from diblock poly(lactic) acid-poly(ethylene)glycol copolymer, diblock poly(lactic acid-co-glycolic acid)-poly(ethylene)glycol copolymer and combination thereof, wherein the therapeutic nanoparticle comprises about 10 to about 30 weight percent poly(ethylene)glycol.

In certain embodiments, the therapeutic nanoparticle comprises a substantially hydrophobic acid and the aforementioned therapeutic agent, wherein the $pK_a$ of the protonated therapeutic agent is at least about 1.0 $pK_a$ units greater than the $pK_a$ of the hydrophobic acid, and a polymer selected from diblock poly(lactic) acid-poly(ethylene)glycol copolymer or a diblock poly(lactic acid-co-glycolic acid)-poly(ethylene)glycol copolymer and combination thereof.

In some embodiments, the therapeutic nanoparticle comprises the aforementioned therapeutic agent, a substantially hydrophobic acid, wherein the molar ratio of the substantially hydrophobic acid to the therapeutic agent ranges from about 0.25:1 to about 2:1 and wherein the $pK_a$ of the protonated therapeutic agent is at least about 1.0 $pK_a$ units greater than the $pK_a$ of the hydrophobic acid, and a polymer selected from diblock poly(lactic) acid-poly(ethylene)glycol copolymer or a diblock poly(lactic acid-co-glycolic acid)-poly(ethylene)glycol copolymer and combination thereof.

In some embodiments, the molar ratio of the substantially hydrophobic acid to the aforementioned therapeutic agent is about 0.5:1 to about 1.5:1. In certain embodiments, the molar ratio of the substantially hydrophobic acid to the aforementioned therapeutic agent is about 0.75:1 to about 1.25:1. In certain embodiments, the molar ratio of the substantially hydrophobic acid to the aforementioned therapeutic agent is about 0.25:1 to about 1:1. In certain embodiments, the $pK_a$ of the protonated form of the aforementioned therapeutic agent is at least about 2.0 $pK_a$ units greater than the $pK_a$ of the hydrophobic acid. In other embodiments, the $pK_a$ of the protonated form of the aforementioned therapeutic agent is at least about 4.0 $pK_a$ units greater than the $pK_a$ of the hydrophobic acid.

In another aspect, a the therapeutic nanoparticle comprises a hydrophobic ion-pair comprising a hydrophobic acid and the aforementioned therapeutic agent; wherein the difference between the $pK_a$ of the protonated form of the aforementioned therapeutic agent and the hydrophobic acid is at least about 1.0 $pK_a$ units, and about 50 to about 99.75 weight percent of a diblock poly(lactic) acid-poly(ethylene)glycol copolymer, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol. In certain embodiments of this aspect of the invention, the difference between the $pK_a$ of the protonated form of the aforementioned therapeutic agent and the hydrophobic acid is at least about 2.0 $pK_a$ units. In other embodiments, the difference between the $pK_a$ of the protonated form of the aforementioned therapeutic agent and the hydrophobic acid is at least about 4.0 $pK_a$ units.

In certain embodiments, the therapeutic nanoparticle comprises about 0.05 to about 20 weight percent of the hydrophobic acid.

In some embodiments, the substantially hydrophobic acid has a log P of about 2 to about 8, where P is the octanol/water partition coefficient of the hydrophobic acid. In some embodiments, the substantially hydrophobic acid has a log P of about 4 to about 8. In some embodiments, the substantially hydrophobic acid has a log P of about 2 to about 7.

In some embodiments, the substantially hydrophobic acid has a $pK_a$ in water of about −1.0 to about 5.0. In other embodiments, the substantially hydrophobic acid has a $pK_a$ in water of about 2.0 to about 5.0.

In certain embodiments, the substantially hydrophobic acid and the aforementioned therapeutic agent form a hydrophobic ion pair in the therapeutic nanoparticle.

In some embodiments, the hydrophobic acid is a fatty acid. For example, in certain embodiments, the fatty acid is a saturated fatty acid, including, but not limited to, caproic acid, enanthic acid, caprylic acid, pelargonic acid, capric acid, undecanoic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, or combinations thereof. In other embodiments, the fatty acid is an omega-3 fatty acid, including, but not limited to, hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, or combinations thereof. In still other embodiments, the fatty acid is an omega-6 fatty acid, including, but not limited to, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, or combinations thereof. In certain other embodiments, the fatty acid is an omega-9 fatty acid, including, but not limited to, oleic acid, eicosenoic acid, mead acid, erucic acid, nervonic acid, or combinations thereof. In other embodiments, the fatty acid is a polyunsaturated fatty acid, including, but not limited, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, or combinations thereof.

In certain embodiments, the hydrophobic acid is a bile acid. For example, in some embodiments, the bile acid includes but is not limited to, chenodeoxycholic acid, ursodeoxycholic acid, deoxycholic acid, hycholic acid, beta-muricholic acid, cholic acid, lithocholic acid, an amino acid-conjugated bile acid, or combinations thereof. In some embodiments, the bile acid is cholic acid. In other embodiments, the amino acid-conjugated bile acid is a glycine-conjugated bile acid or a taurine-conjugated bile acid.

In certain embodiments, the hydrophobic acid includes but is not limited to, dioctyl sulfosuccinic acid, 1-hydroxy-2-naphthoic acid, dodecylsulfuric acid, naphthalene-1,5-disulfonic acid, naphthalene-2-sulfonic acid, pamoic acid, undecanoic acid, or combinations thereof.

In other embodiments, the hydrophobic acid has a molecular weight of between about 200 Da and about 800 Da.

In certain embodiments, the hydrophobic acid is pamoic acid. In other embodiments, the hydrophobic acid is oleic acid. In some embodiments, the weight ratio of 1-(4-{[4-(dimethylamino)piperidin-1-yl]carbonyl}phenyl)-3-[4-(4,6-dimorpholin-4-yl-1,3,5-triazin-2-yl)phenyl]urea to oleic acid is about 6:1. In some embodiments, the weight ratio of 1-(4-{[4-(dimethylamino)piperidin-1-yl]carbonyl}phenyl)-3-[4-(4,6-dimorpholin-4-yl-1,3, 5-triazin-2-yl)phenyl]urea to ratio to pamoic acid is about 1.8:1.

In some embodiments, the therapeutic nanoparticle comprises about 1 to about 20 weight percent of the aforementioned therapeutic agent. In other embodiments, the therapeutic nanoparticle comprises about 1 to about 15 weight percent of the aforementioned therapeutic agent. In other embodiments, the therapeutic nanoparticle comprises about 2 to about 20 weight percent of the afore-mentioned therapeutic agent. In other embodiments, the therapeutic nanoparticle comprises about 2 to about 15 weight percent of the afore-mentioned therapeutic agent. In still other embodiments, the therapeutic nanoparticle of comprises about 4 to about 20 weight percent of the aforementioned therapeutic agent. In still other embodiments, the therapeutic nanoparticle of comprises about 4 to about 15 weight percent of the aforementioned therapeutic agent. In certain other embodiments, the therapeutic nanoparticle comprises about 5 to about 20 weight percent of the aforementioned therapeutic agent. In certain other embodiments, the therapeutic nanoparticle comprises about 5 to about 10 weight percent of the aforementioned therapeutic agent.

In some embodiments, the therapeutic nanoparticle substantially retains the therapeutic agent for at least 1 minute when placed in a phosphate buffer solution at 37° C. In certain embodiments, the therapeutic nanoparticle substantially immediately releases less than about 30% of the therapeutic agent when placed in a phosphate buffer solution at 37° C. In certain other embodiments, the therapeutic nanoparticle releases about 10 to about 45% of the therapeutic agent over about 1 hour when placed in a phosphate buffer solution at 37° C. In some embodiments, the therapeutic nanoparticle releases about 0.01 to about 15% of the therapeutic agent over about 4 hours when placed in a phosphate buffer solution at 37° C. In some embodiments, the therapeutic nanoparticle releases about 0.01 to about 15% of the therapeutic agent over about 10 hours when placed in a phosphate buffer solution at 37° C. In some embodiments, the therapeutic nanoparticle releases about 0.01 to about 25% of the therapeutic agent over about 20 hours when placed in a phosphate buffer solution at 37° C. In some embodiments, the therapeutic nanoparticle releases about 1 to about 40% of the therapeutic agent over about 40 hours when placed in a phosphate buffer solution at 37° C. In still other embodiments, the therapeutic nanoparticle has a release profile that is substantially the same as a release profile for a control nanoparticle that is substantially the same as the therapeutic nanoparticle except that it does not contain a fatty acid or bile acid.

In certain embodiments, the poly(lactic) acid-poly(ethylene)glycol copolymer has a poly(lactic) acid number average molecular weight fraction of about 0.6 to about 0.95. In certain other embodiments, the poly(lactic) acid-poly(ethylene)glycol copolymer has a poly(lactic) acid number average molecular weight fraction of about 0.6 to about 0.8. In still other embodiments, the poly(lactic) acid-poly(ethylene) glycol copolymer has a poly(lactic) acid number average molecular weight fraction of about 0.75 to about 0.85. In other embodiments, the poly(lactic) acid-poly(ethylene)glycol copolymer has a poly(lactic) acid number average molecular weight fraction of about 0.7 to about 0.9.

In certain embodiments, the therapeutic nanoparticle comprises about 10 to about 25 weight percent poly(ethylene)glycol. In certain other embodiments, the therapeutic nanoparticle comprises about 10 to about 20 weight percent poly(ethylene)glycol. In still other embodiments, the therapeutic nanoparticle comprises about 15 to about 25 weight percent poly(ethylene)glycol. In other embodiments, the therapeutic nanoparticle comprises about 20 to about 30 weight percent poly(ethylene)glycol.

In certain embodiments, the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.

In some embodiments, the therapeutic nanoparticle further comprises about 0.2 to about 30 weight percent poly (lactic) acid-poly(ethylene)glycol copolymer functionalized with a targeting ligand. In other embodiments, the therapeutic nanoparticle further comprises about 0.2 to about 30 weight percent poly(lactic) acid-co-poly(glycolic) acid-poly (ethylene)glycol copolymer functionalized with a targeting ligand. In certain embodiments, the targeting ligand is covalently bound to the poly(ethylene)glycol.

In certain embodiments, the hydrophobic acid is a polyelectrolyte. For example, in some embodiments, the polyelectrolyte includes but is not limited to poly(styrene sulfonic acid), polyacrylic acid, polymethacrylic acid, or combinations thereof.

In certain embodiments, a contemplated therapeutic nanoparticle further comprises a mixture of two or more substantially hydrophobic acids. For example, in some embodiments, a contemplated therapeutic nanoparticle comprises a mixture of two substantially hydrophobic acids, a mixture of three substantially hydrophobic acids, a mixture of four substantially hydrophobic acids, or a mixture of five substantially hydrophobic acids. In some embodiments, the mixture of substantially hydrophobic acids comprises oleic acid and cholic acid. In other embodiments, the mixture of two substantially hydrophobic acids are oleic acid and cholic acid.

In another aspect, the therapeutic nanoparticle is prepared by emulsification of a first organic phase comprising a first polymer, the aforementioned therapeutic agent, and a substantially hydrophobic acid, thereby forming an emulsion phase; quenching of the emulsion phase, thereby forming a quenched phase, and finally filtering of the quenched phase to recover the therapeutic nanoparticles.

In some embodiments, the hydrophobic acid used in preparing the therapeutic nanoparticle is a fatty acid. For example, in certain embodiments, the fatty acid used in preparing the therapeutic nanoparticle is a saturated fatty acid including, but not limited to, caproic acid, enanthic acid, caprylic acid, pelargonic acid, capric acid, undecanoic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, or combinations thereof. In other embodiments, the fatty acid used in preparing the therapeutic nanoparticle is an omega-3 fatty acid including, but not limited to, hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, or combinations thereof. In still other embodiments, the fatty acid used in preparing the therapeutic nanoparticle is an omega-6 fatty acid including, but not limited to, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, or combinations thereof. In certain other embodiments, the fatty acid used in preparing the therapeutic nanoparticle is an omega-9 fatty acid including, but not limited to, oleic acid, eicosenoic acid, mead acid, erucic acid, nervonic acid, or combinations thereof. In other embodiments, the fatty acid used in preparing the therapeutic nanoparticle is a polyunsaturated fatty acid including, but not limited to, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, or combinations thereof.

In certain embodiments, the hydrophobic acid used in preparing the therapeutic nanoparticle is a bile acid including, but not limited to, chenodeoxycholic acid, ursodeoxycholic acid, deoxycholic acid, hycholic acid, beta-muricholic acid, cholic acid, lithocholic acid, an amino acid-conjugated bile acid, or combinations thereof. In some embodiments, the bile acid is cholic acid. In other embodiments, the amino acid-conjugated bile acid is a glycine-conjugated bile acid or a taurine-conjugated bile acid.

In certain embodiments, the hydrophobic acid used in preparing the therapeutic nanoparticle includes, but is not limited to, dioctyl sulfosuccinic acid, 1-hydroxy-2-naphthoic acid, dodecylsulfuric acid, naphthalene-1,5-disulfonic acid, naphthalene-2-sulfonic acid, pamoic acid, undecanoic acid, or combinations thereof.

In other embodiments, the hydrophobic acid used in preparing the therapeutic nanoparticle has a molecular weight of between about 200 Da and about 800 Da.

In certain embodiments, the hydrophobic acid used in preparing the therapeutic nanoparticle is pamoic acid. In other embodiments, the hydrophobic acid used in preparing the therapeutic nanoparticle is oleic acid. In some embodiments, the weight ratio of 1-(4-{[4-(dimethylamino)piperidin-1-yl]carbonyl}phenyl)-3-[4-(4,6-dimorpholin-4-yl-1,3, 5-triazin-2-yl)phenyl]urea to oleic acid used in preparing the therapeutic nanoparticle is about 6:1. In some embodiments, the weight ratio of 1-(4-{[4-(dimethylamino)piperidin-1-yl] carbonyl}phenyl)-3-[4-(4,6-dimorpholin-4-yl-1,3,5-triazin-2-yl)phenyl]urea to ratio to pamoic acid used in preparing the therapeutic nanoparticle is about 1.8:1. In some embodiments, the weight ratio of 1-(4-{[4-(dimethylamino)piperidin-1-yl]carbonyl}phenyl)-3-[4-(4,6-dimorpholin-4-yl-1,3, 5-triazin-2-yl)phenyl]urea to oleic acid used in preparing the therapeutic nanoparticle is 6:1. In some embodiments, the weight ratio of 1-(4-{[4-(dimethylamino)piperidin-1-yl] carbonyl}phenyl)-3-[4-(4,6-dimorpholin-4-yl-1,3,5-triazin-2-yl)phenyl]urea to ratio to pamoic acid used in preparing the therapeutic nanoparticle is 1.8:1.

In certain embodiments, the first polymer used in preparing the therapeutic nanoparticle is poly(lactic) acid-poly (ethylene)glycol copolymer. In other embodiments, the first polymer is poly(lactic) acid-co-poly(glycolic) acid-poly (ethylene)glycol copolymer. In certain embodiments, the poly(lactic) acid-poly(ethylene)glycol copolymer has a poly (lactic) acid number average molecular weight fraction of about 0.6 to about 0.95. In certain other embodiments, the poly(lactic) acid-poly(ethylene)glycol copolymer has a poly (lactic) acid number average molecular weight fraction of about 0.6 to about 0.8. In still other embodiments, the poly(lactic) acid-poly(ethylene)glycol copolymer has a poly (lactic) acid number average molecular weight fraction of about 0.75 to about 0.85. In other embodiments, the poly (lactic) acid-poly(ethylene)glycol copolymer has a poly(lactic) acid number average molecular weight fraction of about 0.7 to about 0.9.

In certain embodiments, the therapeutic nanoparticle is prepared using about 10 to about 25 weight percent poly (ethylene)glycol. In certain other embodiments, about 10 to about 20 weight percent poly(ethylene)glycol is used. In still other embodiments, about 15 to about 25 weight percent poly(ethylene)glycol is used. In other embodiments, about 20 to about 30 weight percent poly(ethylene)glycol is used.

In certain embodiments, the poly(lactic) acid-poly(ethylene)glycol copolymer used in preparing the therapeutic nanoparticle has a number average molecular weight of about 15 kDa to about 20 kDa poly(lactic acid) and a number average molecular weight of about 4 kDa to about 6 kDa poly(ethylene)glycol.

In some embodiments, the therapeutic nanoparticle is prepared by further functionalizing about 0.2 to about 30 weight percent poly(lactic) acid-poly(ethylene)glycol copolymer with a targeting ligand. In other embodiments, the therapeutic nanoparticle is prepared by further functionalizing about 0.2 to about 30 weight percent poly(lactic) acid-co-poly(glycolic) acid-poly(ethylene)glycol copolymer with a targeting ligand. In certain embodiments, the targeting ligand is covalently bound to the poly(ethylene)glycol.

In certain embodiments, the hydrophobic acid used in preparing the therapeutic nanoparticle is a polyelectrolyte. For example, in some embodiments, the polyelectrolyte includes, but is not limited to, a poly(styrene sulfonic acid), polyacrylic acid, polymethacrylic acid, or combinations thereof.

In certain embodiments, the therapeutic nanoparticle is prepared using a mixture of two or more substantially hydrophobic acids. For example, in some embodiments, a mixture of two substantially hydrophobic acids, a mixture of three substantially hydrophobic acids, a mixture of four substantially hydrophobic acids, or a mixture of five substantially hydrophobic acids may be used to prepare a therapeutic nanoparticle. In some embodiments, the mixture of substantially hydrophobic acids comprises oleic acid and cholic acid. In other embodiments, the mixture of two substantially hydrophobic acids are oleic acid and cholic acid.

In certain embodiments, the therapeutic nanoparticle comprises the polymer PLA-PEG and the mole ratio of PLA-PEG is about 5:1.

In some embodiments, a therapeutic nanoparticle is prepared by the process combining a first organic phase with a first aqueous solution to form a second phase; emulsifying the second phase to form an emulsion phase, wherein the emulsion phase comprises a first polymer, therapeutic agent, and a substantially hydrophobic acid; quenching of the emulsion phase thereby forming a quenched phase; and filtering the quenched phase to recover the therapeutic nanoparticles, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea, the first organic phase comprises the therapeutic agent and pamoic acid in a weight ratio of therapeutic agent to pamoic acid of about 11:1 and PLA-PEG (in a 16:5 molar ratio) in a weight ratio of therapeutic agent to PLA-PEG of about 1:3 in an organic solvent comprising of benzyl alcohol and ethyl acetate in a weight ratio of benzyl alcohol to ethyl acetate of about 1.25 and the first aqueous solution comprises a polyoxyethylene (100) stearyl ether dissolved in benzyl alcohol in a weight ratio of 0.005:1 and combining the first organic phase and the first aqueous phase in a weight ratio of about 1:5 to form a second phase and emulsifying the second phase formed therefrom and quenching the emulsion phase with 0.1 M citric acid in water solution at pH 4.5 and concentrating the resulting product.

In other embodiments, the therapeutic nanoparticle comprises the aforementioned therapeutic agent or a pharmaceutically acceptable salt thereof and a polymer selected from diblock poly(lactic) acid-poly(ethylene)glycol copolymer or a diblock poly(lactic acid-co-glycolic acid)-poly(ethylene)glycol copolymer and combination thereof.

In certain embodiments, the therapeutic nanoparticle has a targeting ligand additionally present and the ligand is PLA-PEG-GL, wherein GL has the following structure:

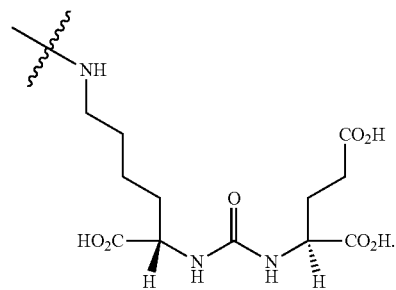 [SMILES: *NCCCC[C@H](NC(=O)N[C@@H](CCC(=O)O)C(=O)O)C(=O)O]

In some embodiments, the therapeutic nanoparticle further comprises a solubilizer. In certain embodiments, the solubilizer is polysorbate 80. In other embodiments, the solubilizer is polyoxyethylene (100) stearyl ether.

In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea, pamoic acid in a weight ratio of therapeutic agent to pamoic acid of about 1.8:1, PLA-PEG (in a 16:5 molar ratio) in a weight ratio of therapeutic agent to PLA-PEG of about 1:3, and PLA-PEG-GL in a weight ratio of PLA-PEG to PLA-PEG-GL of about 44:1. In other embodiments, the therapeutic nanoparticle additionally comprises a solubilizer. In certain such embodiments, the solubilizer is polyoxyethylene (100) stearyl ether.

In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea, oleic acid in a weight ratio of therapeutic agent to oleic acid of about 6:1, PLA-PEG (in a 16:5 molar ratio) in a weight ratio of therapeutic agent to PLA-PEG of about 1:7, and PLA-PEG-GL in a weight ratio of PLA-PEG to PLA-PEG-GL of about 46:1. In some embodiments, the therapeutic nanoparticle additionally comprises cholic acid. In other embodiments, the therapeutic nanoparticle additionally comprises a solubilizer. In certain such embodiments, the solubilizer is polysorbate 80.

In yet another aspect, a pharmaceutical composition comprising a therapeutic nanoparticle described herein and a pharmaceutically acceptable excipient is provided. The pharmaceutical composition may comprise a plurality of contemplated therapeutic nanoparticles.

In certain embodiments, the pharmaceutical composition further comprises a saccharide. For example, in some embodiments, the saccharide is a disaccharide selected from the group consisting of sucrose or trehalose, or a mixture thereof.

In certain embodiments, the pharmaceutical composition further comprises a cyclodextrin. For example, in some embodiments, the cyclodextrin includes, but is not limited to, α-cyclodextrin, β-cyclodextrin, γ-cyclodextrin, heptakis-(2,3,6-tri-O-benzyl)-β-cyclodextrin, heptakis-(2,3,6-tri-O-benzoyl)-β-cyclodextrin, or mixtures thereof.

In another aspect, a method of treating cancer in a subject in need thereof is provided. The method comprises administering to the subject a therapeutically effective amount of a pharmaceutical composition as described herein. In some embodiments, the cancer is chronic myelogenous leukemia. In certain embodiments, the cancer includes, but is not limited to chronic myelomonocytic leukemia, hypereosinophilic syndrome, renal cell carcinoma, hepatocellular carcinoma, Philadelphia chromosome positive acute lymphoblastic leukemia, non-small cell lung cancer, pancreatic cancer, breast cancer, a solid tumor, mantle cell lymphoma, gastrointestinal stromal tumor, or head and neck cancer. In some embodiments, the cancer is breast cancer.

In still another aspect, a method of treating a gastrointestinal stromal tumor in a subject in need thereof is provided by administering to the subject a therapeutically effective amount of a pharmaceutical composition described herein.

In yet another aspect, a process for preparing a therapeutic nanoparticle is provided. The process comprises combining a first organic phase with a first aqueous solution to form a second phase; emulsifying the second phase to form an emulsion phase, wherein the emulsion phase comprises a first polymer, the aforementioned therapeutic agent, and a substantially hydrophobic acid; followed by quenching of the emulsion phase, thereby forming a quenched phase, and finally filtering the quenched phase to recover the therapeutic nanoparticles.

In some embodiments, the process further comprises combining the aforementioned therapeutic agent and the substantially hydrophobic acid in the second phase prior to emulsifying the second phase. In certain embodiments, the aforementioned therapeutic agent and the substantially hydrophobic acid form a hydrophobic ion pair prior to emulsifying the second phase. In certain other embodiments, the aforementioned therapeutic agent and the substantially hydrophobic acid form a hydrophobic ion pair during emulsification of the second phase. In certain embodiments, the process further comprises combining the aforementioned therapeutic agent and the substantially hydrophobic acid in the second phase substantially concurrently with emulsifying the second phase. For example, in some embodiments, the first organic phase comprises the aforementioned therapeutic agent and the first aqueous solution comprises the substantially hydrophobic acid.

In some embodiments, the aforementioned therapeutic agent, when protonated, has a first $pK_a$, the substantially hydrophobic acid has a second $pK_a$, and the emulsion phase is quenched with an aqueous solution having a pH equal to a $pK_a$ unit between the first $pK_a$ and the second $pK_a$. For example, in certain embodiments, the quenched phase has a pH equal to a $pK_a$ unit between the first $pK_a$ and the second $pK_a$. In other embodiments, the aforementioned therapeutic agent, when protonated, has a first $pK_a$, the substantially hydrophobic acid has a second $pK_a$, and the first aqueous solution has a pH equal to a $pK_a$ unit between the first $pK_a$ and the second $pK_a$. In certain other embodiments, the pH is equal to a $pK_a$ unit that is about equidistant between the first $pK_a$ and the second $pK_a$.

In some embodiments, the aforementioned therapeutic agent, when protonated, has a first $pK_a$, the substantially hydrophobic acid has a second $pK_a$, and the emulsion phase is quenched with an aqueous solution having a pH equal to a $pK_a$ unit between the first $pK_a$ and the second $pK_a$. For example, in certain embodiments, the quenched phase has a pH equal to a $pK_a$ unit between the first $pK_a$ and the second $pK_a$. In other embodiments, the aforementioned therapeutic agent, when protonated, has a first $pK_a$, the substantially hydrophobic acid has a second $pK_a$, and the first aqueous solution has a pH equal to a $pK_a$ unit between the first $pK_a$ and the second $pK_a$. In certain other embodiments, the pH is equal to a $pK_a$ unit that is equidistant between the first $pK_a$ and the second $pK_a$.

In another aspect, there is provided a therapeutic nanoparticle as described herein for use as a medicament in a subject.

In yet another aspect, there is provided a therapeutic nanoparticle as described herein for use in the production of an anti-proliferative effect in a subject.

In still another aspect, there is provided a therapeutic nanoparticle as described herein for use in a subject as an anti-invasive agent in the containment and/or treatment of solid tumor disease.

In yet another aspect, there is provided the use of a therapeutic nanoparticle as described herein in the prevention or treatment of cancer in a subject.

In still another aspect, there is provided a therapeutic nanoparticle as described herein for use in the prevention or treatment of cancer in a subject.

In yet another aspect, there is provided the use of a therapeutic nanoparticle as described herein in the manufacture of a medicament for the prevention or treatment of cancer in a subject.

In still another aspect, there is provided the use of a therapeutic nanoparticle as described herein for the production of an anti-proliferative effect in a subject.

In yet another aspect, there is provided the use of a therapeutic nanoparticle as described herein in the manufacture of a medicament for use in the production of an anti-proliferative effect in a subject.

In still another aspect, there is provided the use of a therapeutic nanoparticle as described herein in the manufacture of a medicament for use in a subject as an anti-invasive agent in the containment and/or treatment of solid tumor disease.

In yet another aspect, there is provided a method for producing an anti-proliferative effect in a subject in need of such treatment which comprises administering to said subject an effective amount of a therapeutic nanoparticle as described herein.

In still another aspect, there is provided a method for producing an anti-invasive effect by the containment and/or treatment of solid tumor disease in a subject in need of such treatment which comprises administering to said subject an effective amount of a therapeutic nanoparticle as described herein.

In yet another aspect, there is provided a therapeutic nanoparticle as described herein for use in the prevention or treatment of solid tumor disease in a subject.

In still another aspect, there is provided the use of a therapeutic nanoparticle as described herein in the manufacture of a medicament for use in the prevention or treatment of solid tumor disease in a subject.

In yet another aspect, there is provided a method for the prevention or treatment of solid tumor disease in a subject in need of such treatment which comprises administering to said subject an effective amount of a therapeutic nanoparticle as described herein.

DETAILED DESCRIPTION

Definitions

Figure 1:
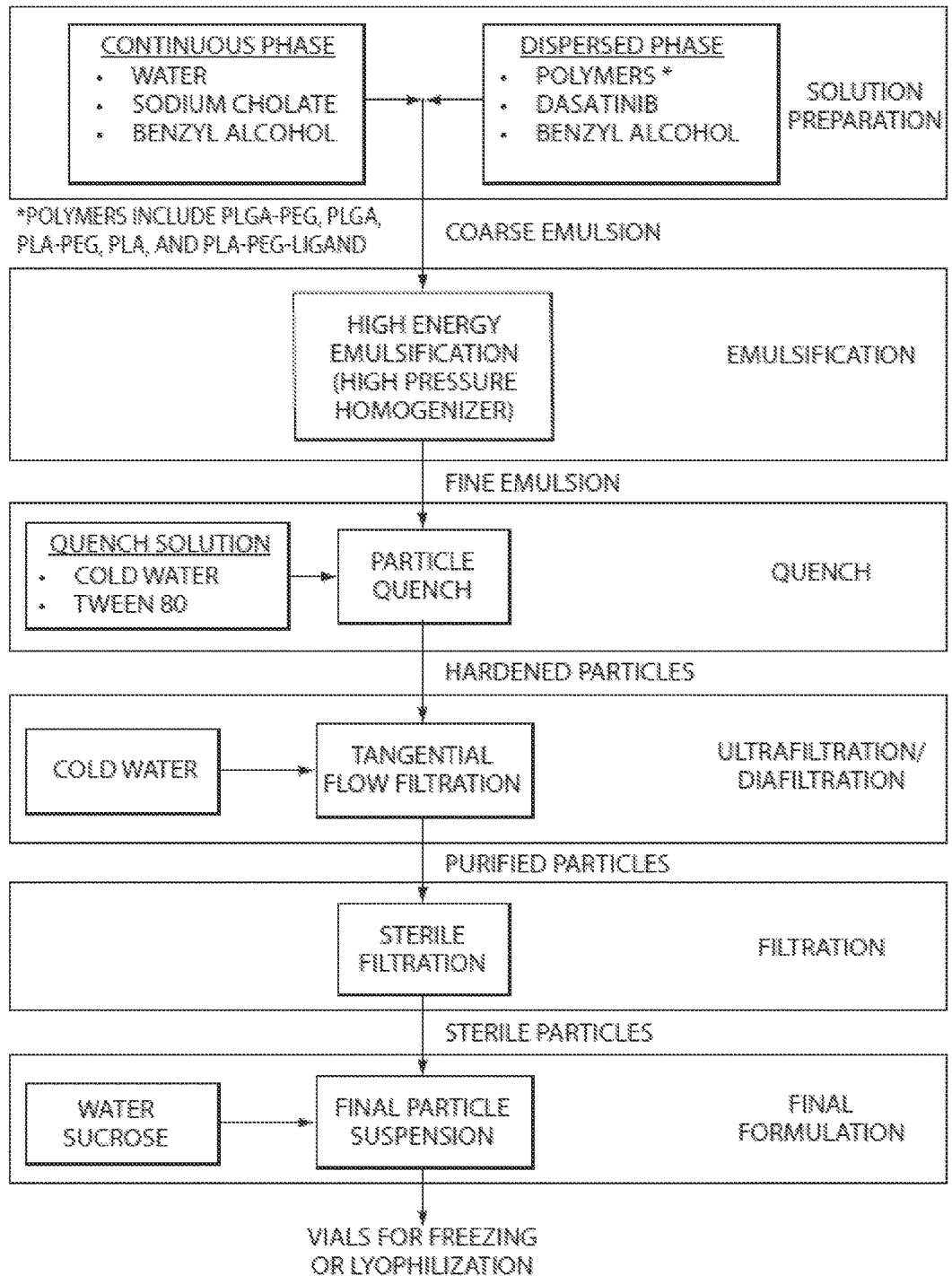
FIG. 1 is flow chart for an emulsion process for forming a disclosed nanoparticle.

The definitions set forth in this application are intended to clarify terms used throughout this application.

The term "herein" means the entire application.

Unless defined otherwise, all technical and scientific terms used herein have the same meaning as those commonly understood by one of ordinary skill in the art to which these inventions belong. Although methods and materials similar or equivalent to those described herein can be used in the practice or testing of the inventions, suitable methods and materials are described below. The materials, methods and examples are illustrative only, and are not intended to be limiting. All publications, patents and other documents mentioned herein are incorporated by reference in their entirety.

Each embodiment of the inventions described herein may be taken alone or in combination with any one or more other embodiments of the inventions.

Throughout this application, the word "a" or "an" will be understood to imply the inclusion of one or more of the integers modified by the article "a" or "an."

Throughout this application, the word "comprise" or variations such as "comprises" or "comprising" will be understood to imply the inclusion of a stated integer or groups of integers but not the exclusion of any other integer or group of integers.

Throughout the application, where compositions are described as having, including, or comprising, specific components, it is contemplated that compositions also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "or" as used herein should be understood to mean "and/or", unless the context clearly indicates otherwise.

The term "alkoxy" refers to an alkyl group, preferably a lower alkyl group, having an oxygen attached thereto. Representative alkoxy groups include methoxy, ethoxy, propoxy, tert-butoxy and the like.

Moreover, the term "alkyl" (or "lower alkyl") as used herein is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —$CF_3$, —CN and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. $C_0$ alkyl indicates a hydrogen where the group is in a terminal position, a bond if internal.

The term "amide", as used herein, refers to a group

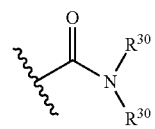

wherein each $R^{30}$ independently represent a hydrogen or hydrocarbyl group, or two $R^{30}$ are taken together with the N atom to which they are attached complete a heterocycle having from 4 to 12 atoms in the ring structure.

The term "aryl" as used herein includes substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons or heteroatoms are common to two adjoining rings wherein at least one of the rings is aromatic, e.g., the other cyclic rings can be cycloalkyls, cycloalkenyls, cycloalkynyls, aryls, heteroaryls, and/or heterocyclyls.

The terms "arylalkyl" or "aralkyl", as used herein, refers to an alkyl group substituted with an aryl group.

The term "azido" is art-recognized and refers to the group —N=N$^+$=N$^-$.

The term "carboxy", as used herein, refers to a group represented by the formula —CO$_2$H.

The terms "halo" and "halogen" as used herein means halogen and includes chloro, fluoro, bromo, and iodo.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, carbocycle, heterocyclyl, alkyl, alkenyl, alkynyl, and combinations thereof.

The term "hydroxy", as used herein, refers to an —OH group.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, but not limited to, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

"Optional" or "optionally" means that the subsequently described circumstance may or may not occur, so that the application includes instances where the circumstance occurs and instances where it does not. For example, the phrase "optionally substituted" means that a non-hydrogen substituent may or may not be present on a given atom, and, thus, the application includes structures wherein a non-hydrogen substituent is present and structures wherein a non-hydrogen substituent is not present.

The terms "healthy" and "normal" are used interchangeably herein to refer to a subject or particular cell or tissue that is devoid (at least to the limit of detection) of a disease condition.

Unless indicated to the contrary, the term "basic therapeutic agent" or "therapeutic agent" refers to the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof. It has the structure shown below:

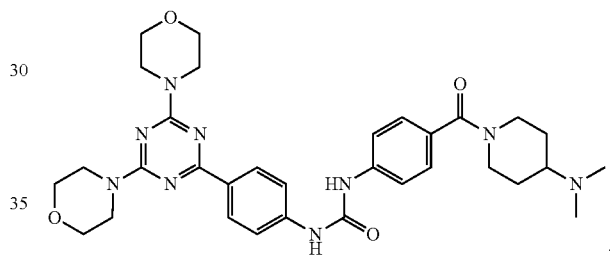

It is described in U.S. Pat. No. 8,039,469, the contents of which are incorporated by reference. The calculated log of the octanol:saline partition coefficient (c log P)=1.24 (calculated partition coefficient). The log D, the distribution constant, at pH 6.5=0.212, while log D at pH 7.4=1.08. As indicated above, it is a base. It is a protonatable nitrogen-containing therapeutic agent. As used herein, a "protonatable nitrogen-containing therapeutic agent" includes any pharmaceutically active agent that contains at least one nitrogen-containing functional group that is capable of being protonated. In other words, the therapeutic agent has a nitrogen atom thereon which has a lone pair of electrons that could potentially accept a proton. The pKa refers to the acid dissociation constant on a logarithmic scale of the corresponding protonated form of the therapeutic agent. In other words, if a proton (H+) were present at the nitrogen atoms where there is an arrow indicated, the therapeutic agent would have the pKa indicated below:

ACD- 5.85

-continued

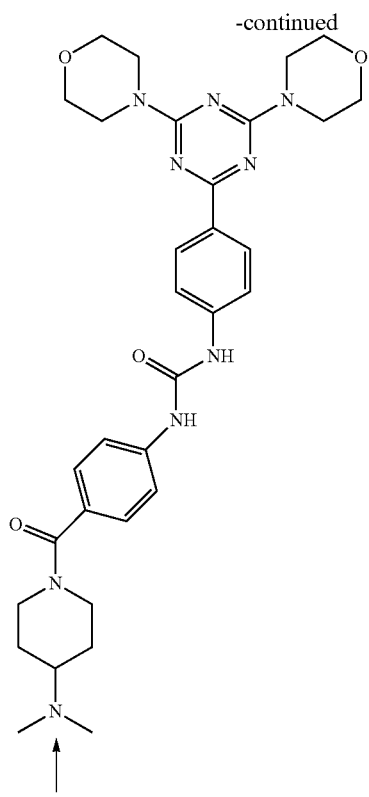

ACD- 9.06

The pKa information for the most basic nitrogen (bottom) and a less basic but still protonatable nitrogen (upper) are shown above. ACD is a calculated number using standard techniques known in the art, such as described in Liao C Z, Nicklaus M C. Comparison of nine programs predicting pK(a) values of pharmaceutical substances. *J. Chem. Inform. Model.* 49(12):2801-2812, 2009. It has to be understood that the pKa of the therapeutic agent refers to the protonated form thereof.

The therapeutic agent of the present invention possesses one or more chiral centers and the present invention includes each separate enantiomer of such compounds as well as mixtures of enantiomers. Where multiple chiral centers exist, the invention includes each combination as well as mixtures thereof. All chiral, diastereomeric, and racemic forms of a structure are intended, unless the specific stereochemistry or isomeric form is specifically indicated. It is well known in the art how to prepare optically active forms such as by resolution of racemic forms or by synthesis from optically active starting materials.

The term "substantially" when used in reference to a compound such as "hydrophobic acid" refers to the compound being present in at least 1% by weight or refers to a hydrophobic acid with a log P above 2. A hydrophobic acid with a log P above 2 has a greater tendency to partition into the organic phase.

The term "hydrophobic acid" refers to a lipophilic acid which has a log of a −7 or greater, i.e., −6, −5, −4, −3, −2, −1, 0, 1, 2, 3, 4, 5, 6, 7, 8, 9, 10, 11, 12, 13, 14, 15, 16.

The nanoparticles described herein may also contain pharmaceutically acceptable salts of the therapeutic agent. Representative "pharmaceutically acceptable salts" include but are not limited to, e.g., water-soluble and water-insoluble salts, such as the acetate, aluminum, amsonate (4,4-diaminostilbene-2,2-disulfonate), benzathine (N,N'-dibenzylethylenediamine), benzenesulfonate, benzoate, bicarbonate, bismuth, bisulfate, bitartrate, borate, bromide, butyrate, calcium, calcium edetate, camsylate (camphorsulfonate), carbonate, chloride, choline, citrate, clavulariate, diethanolamine, dihydrochloride, diphosphate, edetate, edisylate (camphorsulfonate), esylate (ethanesulfonate), ethylenediamine, fumarate, gluceptate (glucoheptonate), gluconate, glucuronate, glutamate, hexafluorophosphate, hexylresorcinate, hydrabamine(N,N'-bis(dehydroabietyl)ethylenediamine), hydrobromide, hydrochloride, hydroxynaphthoate, 1-hydroxy-2-naphthoate, 3-hydroxy-2-naphthoate, iodide, isothionate (2-hydroxyethanesulfonate), lactate, lactobionate, laurate, lauryl sulfate, lithium, magnesium, malate, maleate, mandelate, meglumine (1-deoxy-1-(methylamino)-D-glucitol), mesylate, methyl bromide, methylnitrate, methylsulfate, mucate, napsylate, nitrate, N-methylglucamine ammonium salt, oleate, oxalate, palmitate, pamoate (4,4'-methylenebis-3-hydroxy-2-naphthoate, or embonate), pantothenate, phosphate, picrate, polygalacturonate, potassium, propionate, p-toluenesulfonate, salicylate, sodium, stearate, subacetate, succinate, sulfate, sulfosaliculate, suramate, tannate, tartrate, teoclate (8-chloro-3,7-dihydro-1,3-dimethyl-1H-purine-2,6-dione), triethiodide, tromethamine(2-amino-2-(hydroxymethyl)-1,3-propanediol), valerate, and zinc salts.

When used herein below, unless indicated to the contrary, % is % by weight.

Described herein are polymeric nanoparticles that include the basic therapeutic agent and methods of making and using such therapeutic nanoparticles.

In some embodiments, inclusion (i.e., doping) of a substantially hydrophobic acid (e.g., a fatty acid and/or a bile acid) in a disclosed nanoparticle and/or included in a nanoparticle preparation process may result in nanoparticles that include improved drug loading. Furthermore, in certain embodiments, nanoparticles that include and/or are prepared in the presence of the hydrophobic acid may exhibit improved controlled release properties. For example, disclosed nanoparticles may more slowly release the therapeutic agent as compared to nanoparticles prepared in the absence of the hydrophobic acid.

Without wishing to be bound by any theory, it is believed that the disclosed nanoparticle formulations that include a hydrophobic acid (e.g., fatty acid and/or bile acid) have significantly improved formulation properties (e.g., drug loading and/or release profile) through formation of a hydrophobic ion-pair (HIP), between the therapeutic agent on the lone pair of electrons on one or more of the nitrogen atoms on the therapeutic agent indicated above, for example, on the amine moiety and an acid. As used herein, a HIP is a pair of oppositely charged ions held together by Coulombic attraction. Also without wishing to be bound by any theory, in some embodiments, HIP can be used to increase the hydrophobicity of the therapeutic agent containing ionizable groups (e.g., amines). When the therapeutic agent has increased hydrophobicity, it is beneficial for nanoparticle formulations, for it results in a HIP formation that may provide higher solubility of the therapeutic agent in organic solvents. HIP formation, as contemplated herein, can result in nanoparticles having for example, increased drug loading. Slower release of the therapeutic agent from the nanoparticles may also occur, for example in some embodiments, due to a decrease in the therapeutic agent's solubility in aqueous solution. Furthermore, complexing the therapeutic agent with large hydrophobic counter ions may slow diffusion of the therapeutic agent within the polymeric matrix. Advantageously, HIP formation occurs without the need for covalent conjugation of the hydrophobic group to the therapeutic agent.

Without wishing to be bound by any theory, it is believed that the strength of the HIP impacts the drug load and release rate of the contemplated nanoparticles. For example, the strength of the HIP may be increased by increasing the magnitude of the difference between the $pK_a$ of the protonated form of the therapeutic agent and the $pK_a$ of the hydrophobic acid, as discussed in more detail below. Also without wishing to be bound by any theory, it is believed that the conditions for ion pair formation impact the drug load and release rate of the contemplated nanoparticles.

Nanoparticles disclosed herein include one, two, three or more biocompatible and/or biodegradable polymers. For example, a contemplated nanoparticle may include about 35 to about 99.75 weight percent in some embodiments; about 50 to about 99.75 weight percent, in some other embodiments; about 50 to about 99.5 weight percent, in some embodiments; about 50 to about 99 weight percent in still other embodiments; about 50 to about 98 weight percent in further embodiments; about 50 to about 97 weight percent in still further embodiments; about 50 to about 96 weight percent in additional embodiments; about 50 to about 95 weight percent in other embodiments, about 50 to about 94 weight percent in still other embodiments; about 50 to about 93 weight percent in other embodiments; about 50 to about 92 weight percent in still other embodiments; about 50 to about 91 weight percent, in some embodiments about 50 to about 90 weight percent; in some embodiments, about 50 to about 85 weight percent; in some embodiments about 60 to about 85 weight percent; in some embodiments, about 65 to about 85 weight percent; and in some embodiments, about 50 to about 80 weight percent of one or more block copolymers that include a biodegradable polymer and poly(ethylene glycol) (PEG), and about 0 to about 50 weight percent of a biodegradable homopolymer.

In some embodiments, a contemplated nanoparticle may include 35 to 99.75 weight percent in some embodiments; 50 to 99.75 weight percent, in some other embodiments; 50 to 99.5 weight percent, in some embodiments; 50 to 99 weight percent in still other embodiments; 50 to 98 weight percent in further embodiments; 50 to 97 weight percent in still further embodiments; 50 to 96 weight percent in additional embodiments; 50 to 95 weight percent in other embodiments, 50 to 94 weight percent in still other embodiments; 50 to 93 weight percent in other embodiments; 50 to 92 weight percent in still other embodiments; 50 to 91 weight percent, in some embodiments 50 to 90 weight percent; in some embodiments, 50 to 85 weight percent; in some embodiments 60 to 85 weight percent; in some embodiments, 65 to 85 weight percent; and in some embodiments, 50 to 80 weight percent of one or more block copolymers that include a biodegradable polymer and poly(ethylene glycol) (PEG), and 0 to 50 weight percent of a biodegradable homopolymer.

In some embodiments, disclosed nanoparticles may include about 0.2 to about 35 weight percent, about 0.2 to about 25 weight percent, about 0.2 to about 20 weight percent, about 0.2 to about 10 weight percent, about 0.2 to about 5 weight percent, about 0.5 to about 5 weight percent, about 0.75 to about 5 weight percent, about 1 to about 5 weight percent, about 2 to about 5 weight percent, about 3 to about 5 weight percent, about 1 to about 20 weight percent, about 2 to about 20 weight percent, about 3 to about 20 weight percent, about 4 to about 20 weight percent, about 5 to about 20 weight percent, about 1 to about 15 weight percent, about 2 to about 15 weight percent, about 3 to about 15 weight percent, about 4 to about 15 weight percent, about 5 to about 15 weight percent, about 1 to about 10 weight percent, about 2 to about 10 weight percent, about 3 to about 10 weight percent, about 4 to about 10 weight percent, about 5 to about 10 weight percent, about 10 to about 30 weight percent, or about 15 to about 25 weight percent of the therapeutic agent. In some embodiments the disclosed nanoparticles include about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 weight percent of the therapeutic agent.

In certain embodiments, disclosed nanoparticles may include 0.2 to 35 weight percent, 0.2 to 25 weight percent, 0.2 to 20 weight percent, 0.2 to 10 weight percent, 0.2 to 5 weight percent, 0.5 to 5 weight percent, 0.75 to 5 weight percent, 1 to 5 weight percent, 2 to 5 weight percent, 3 to 5 weight percent, 1 to 20 weight percent, 2 to 20 weight percent, 3 to 20 weight percent, 4 to 20 weight percent, 5 to 20 weight percent, 1 to 15 weight percent, 2 to 15 weight percent, 3 to 15 weight percent, 4 to 15 weight percent, 5 to 15 weight percent, 1 to 10 weight percent, 2 to 10 weight percent, 3 to 10 weight percent, 4 to 10 weight percent, 5 to 10 weight percent, 10 to 30 weight percent, or 15 to 25 weight percent of the therapeutic agent. In some embodiments the disclosed nanoparticles include 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 weight percent of the therapeutic agent.

In certain embodiments, disclosed nanoparticles comprise a hydrophobic acid (e.g., a fatty acid and/or bile acid) and/or are prepared by a process that includes a hydrophobic acid. Such nanoparticles may have a higher drug loading than nanoparticles prepared by a process without a hydrophobic acid. For example, drug loading (e.g., by weight) of disclosed nanoparticles prepared by a process comprising the hydrophobic acid may be between about 2 times to about 10 times higher, or even more, than disclosed nanoparticles prepared by a process without the hydrophobic acid. In some embodiments, the drug loading (by weight) of disclosed nanoparticles prepared by a first process comprising the hydrophobic acid may be at least about 2 times higher, at least about 3 times higher, at least about 4 times higher, at least about 5 times higher, or at least about 10 times higher than disclosed nanoparticles prepared by a second process, where the second process is identical to the first process except that the second process does not include the hydrophobic acid.

In certain embodiments, drug loading (e.g., by weight) of disclosed nanoparticles prepared by a process comprising the hydrophobic acid may be between 2 times to 10 times higher, or even more, than disclosed nanoparticles prepared by a process without the hydrophobic acid. In some embodiments, the drug loading (by weight) of disclosed nanoparticles prepared by a first process comprising the hydrophobic acid may be at least 2 times higher, at least 3 times higher, at least 4 times higher, at least 5 times higher, or at least 10 times higher than disclosed nanoparticles prepared by a second process, where the second process is identical to the first process except that the second process does not include the hydrophobic acid.

Any suitable hydrophobic acid is contemplated. In some embodiments, the hydrophobic acid may be a carboxylic acid (e.g., a monocarboxylic acid, dicarboxylic acid, tricarboxylic acid, or the like), a sulfinic acid, a sulfenic acid, or a sulfonic acid. In some cases, a contemplated hydrophobic acid may include a mixture of two or more acids. For example, in certain embodiments, the hydrophobic acid may comprise a mixture of two substantially hydrophobic acids, in some embodiments a mixture of three substantially hydrophobic acids, in some embodiments a mixture of four substantially hydrophobic acids, or in some embodiments five substantially hydrophobic acids. In some embodiments, the mixture of substantially hydrophobic acids comprises oleic acid and cholic acid. In other embodiments, the mixture of two hydrophobic acids is oleic acid and cholic acid.

In some cases, a salt of a hydrophobic acid may be used in a formulation.

For example, a disclosed carboxylic acid may be an aliphatic carboxylic acid (e.g., a carboxylic acid having a cyclic or acyclic, branched or unbranched, hydrocarbon chain). Disclosed carboxylic acids may, in some embodiments, be substituted with one or more functional groups including, but not limited to, halogen (i.e., F, Cl, Br, and I), sulfonyl, nitro, and oxo. In certain embodiments, a disclosed carboxylic acid may be unsubstituted.

Exemplary carboxylic acids may include a substituted or unsubstituted fatty acid (e.g., $C_6$-$C_{50}$ fatty acid). In some instances, the fatty acid may be a $C_{10}$-$C_{20}$ fatty acid. In other instances, the fatty acid may be a $C_{15}$-$C_{20}$ fatty acid. The fatty acid may, in some cases, be saturated. In other embodiments, the fatty acid may be unsaturated. For instance, the fatty acid may be a monounsaturated fatty acid or a polyunsaturated fatty acid. In some embodiments, a double bond of an unsaturated fatty acid group can be in the cis conformation. In some embodiments, a double bond of an unsaturated fatty acid can be in the trans conformation. Unsaturated fatty acids include, but are not limited to, omega-3, omega-6, or omega-9 fatty acids.

Non-limiting examples of saturated fatty acids include caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, henatriacontanoic acid, lacceroic acid, psyllic acid, geddic acid, ceroplastic acid, hexatriacontanoic acid, or combinations thereof.

Non-limiting examples of unsaturated fatty acids include hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, oleic acid ($pK_a$=~4-5; log P=6.78), eicosenoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, palmitoleic acid, vaccenic acid, gadoleic acid, erucic acid, or combinations thereof.

Other non-limiting examples of hydrophobic acids include aromatic acids, such as 1-hydroxy-2-naphthoic acid (i.e., xinafoic acid) ($pK_a$=~2-3; log P=2.97), naphthalene-1,5-disulfonic acid ($pK_a$=~2; log P=1.3), naphthalene-2-sulfonic acid ($pK_a$=−1.8; log P=2.1), pamoic acid ($pK_a$=2.4; log P=6.17), cinnamic acid, phenylacetic acid, (±)-camphor-10-sulfonic acid, dodecylbenzenesulfonic acid ($pK_a$=−1.8; log P=6.6), or combinations thereof. Other non-limiting examples of hydrophobic acids include dodecylsulfuric acid ($pK_a$=−0.09; log P=4.5), dioctyl sulfosuccinic acid (i.e., docusate acid) ($pK_a$=−0.8; log P=5.2), dioleoyl phosphatidic acid ($pK_a$=~2), or Vitamin $D_3$-sulfate ($pK_a$=−1.5).

In some embodiments, the hydrophobic acid may be a bile acid. Non-limiting examples of bile acids include chenodeoxycholic acid, ursodeoxycholic acid, deoxycholic acid ($pK_a$=4.65; log P=3.79), hycholic acid, beta-muricholic acid, cholic acid ($pK_a$=~4.5; log P=2.48), taurocholic acid, cholesteryl sulfate ($pK_a$=−1.4), lithocholic acid, an amino acid-conjugated bile acid, or combinations thereof. An amino-acid conjugated bile acid may be conjugated to any suitable amino acid. In some embodiments, the amino acid-conjugated bile acid is a glycine-conjugated bile acid or a taurine-conjugated bile acid.

In certain instances, the hydrophobic acid may be a polyelectrolyte. For example, the polyelectrolyte may be a polysulfonic acid (e.g., poly(styrene sulfonic acid) or dextran sulfate) or a polycarboxylic acid (e.g., polyacrylic acid or polymethacrylic acid).

In some instances, a contemplated hydrophobic acid may have a molecular weight of less than about 1000 Da, in some embodiments less than about 500 Da, in some embodiments less than about 400 Da, in some embodiments less than about 300 Da, in some embodiments less than about 250 Da, in some embodiments less than about 200 Da, and in some embodiments less than about 150 Da. In some cases, the hydrophobic acid may have a molecular weight of between about 100 Da and about 1000 Da, in some embodiments between about 200 Da and about 800 Da, in some embodiments between about 200 Da and about 600 Da, in some embodiments between about 100 Da and about 300 Da, in some embodiments between about 200 Da and about 400 Da, in some embodiments between about 300 Da and about 500 Da, and in some embodiments between about 300 Da and about 1000 Da. In certain embodiments, a contemplated acid may have a molecular weight of greater than about 200 kDa, in some embodiments greater than about 300 Da, in some embodiments greater than about 400 Da, and in some embodiments greater than about 500 Da. In certain embodiments, the release rate of a therapeutic agent from a nanoparticle can be slowed by increasing the molecular weight of the hydrophobic acid used in the nanoparticle formulation.

In some instances, a contemplated hydrophobic acid may have a molecular weight of less than 1000 Da, in some embodiments less than 500 Da, in some embodiments less than 400 Da, in some embodiments less than 300 Da, in some embodiments less than 250 Da, in some embodiments less than 200 Da, and in some embodiments less than 150 Da. In some cases, the hydrophobic acid may have a molecular weight of between 100 Da and 1000 Da, in some embodiments between 200 Da and 800 Da, in some embodiments between 200 Da and 600 Da, in some embodiments between 100 Da and 300 Da, in some embodiments between 200 Da and 400 Da, in some embodiments between 300 Da and 500 Da, and in some embodiments between 300 Da and 1000 Da. In certain embodiments, a contemplated acid may have a molecular weight of greater than 200 kDa, in some embodiments greater than 300 Da, in some embodiments greater than 400 Da, and in some embodiments greater than 500 Da.

In some embodiments, a hydrophobic acid may be chosen, at least in part, on the basis of the strength of the acid. For example, the hydrophobic acid may have an acid dissociation constant in water ($pK_a$) of about −5 to about 7, in some embodiments about −3 to about 5, in some embodiments about −3 to about 4, in some embodiments about −3 to about 3.5, in some embodiments about −3 to about 3, in some embodiments about −3 to about 2, in some embodiments about −3 to about 1, in some embodiments about −3 to about 0.5, in some embodiments, about −1.0 to about 5.0, in some embodiments about −0.5 to about 0.5, in some embodiments about 1 to about 7, in some embodiments about 2 to about 7, in some embodiments about 2.0 to about 5.0, in some embodiments about 3 to about 7, in some embodiments about 4 to about 6, in some embodiments about 4 to about 5.5, in some embodiments about 4 to about 5, and in some embodiments about 4.5 to about 5, determined at 25° C. In some embodiments, the acid may have a $pK_a$ of less than about 7, less than about 5, less than about 3.5, less than about 3, less than about 2, less than about 1, or less than about 0, determined at 25° C.

In some embodiments, the hydrophobic acid may have an acid dissociation constant in water ($pK_a$) of −5 to 7, in some embodiments −3 to 5, in some embodiments −3 to 4, in some embodiments −3 to 3.5, in some embodiments −3 to 3, in some embodiments −3 to 2, in some embodiments −3 to 1, in some embodiments −3 to 0.5, in some embodiments, −1.0 to 5.0, in some embodiments −0.5 to 0.5, in some embodiments 1 to 7, in some embodiments 2 to 7, in some embodiments 2.0 to 5.0, in some embodiments 3 to 7, in some embodiments 4 to 6, in some embodiments 4 to 5.5, in some embodiments 4 to 5, and in some embodiments 4.5 to 5, determined at 25° C. In some embodiments, the acid may have a $pK_a$ of less than 7, less than 5, less than 3.5, less than 3, less than 2, less than 1, or less than 0, determined at 25° C.

In certain embodiments, the hydrophobic acid may be chosen, at least in part, on the basis of the difference between the $pK_a$ of the hydrophobic acid and the $pK_a$ of the protonated therapeutic agent. For example, in some instances, the difference between the $pK_a$ of the hydrophobic acid and the $pK_a$ of the protonated therapeutic agent may be between about 1 $pK_a$ unit and about 15 $pK_a$ units, in some embodiments between about 1 $pK_a$ unit and about 10 $pK_a$ units, in some embodiments between about 1 $pK_a$ unit and about 5 $pK_a$ units, in some embodiments between about 1 $pK_a$ unit and about 3 $pK_a$ units, in some embodiments between about 1 $pK_a$ unit and about 2 $pK_a$ units, in some embodiments between about 2 $pK_a$ units and about 15 $pK_a$ units, in some embodiments between about 2 $pK_a$ units and about 10 $pK_a$ units, in some embodiments between about 2 $pK_a$ units and about 5 $pK_a$ units, in some embodiments between about 2 $pK_a$ units and about 3 $pK_a$ units, in some embodiments between about 3 $pK_a$ units and about 15 $pK_a$ units, in some embodiments between about 3 $pK_a$ units and about 10 $pK_a$ units, in some embodiments between about 3 $pK_a$ units and about 5 $pK_a$ units, in some embodiments between about 4 $pK_a$ units and about 15 $pK_a$ units, in some embodiments between about 4 $pK_a$ units and about 10 $pK_a$ units, in some embodiments between about 4 $pK_a$ units and about 6 $pK_a$ units, in some embodiments between about 5 $pK_a$ units and about 15 $pK_a$ units, in some embodiments between about 5 $pK_a$ units and about 10 $pK_a$ units, in some embodiments between about 5 $pK_a$ units and about 7 $pK_a$ units, in some embodiments between about 7 $pK_a$ units and about 15 $pK_a$ units, in some embodiments between about 7 $pK_a$ units and about 9 $pK_a$ units, in some embodiments between about 7 $pK_a$ units and about 15 $pK_a$ units, in some embodiments between about 7 $pK_a$ units and about 9 $pK_a$ units, in some embodiments between about 9 $pK_a$ units and about 15 $pK_a$ units, in some embodiments between about 9 $pK_a$ units and about 11 $pK_a$ units, in some embodiments between about 11 $pK_a$ units and about 13 $pK_a$ units, in some embodiments between about 11 $pK_a$ units and 13 $pK_a$ units, and in some embodiments between 13 $pK_a$ units and 15 $pK_a$ units, determined at 25° C.

In some instances, the difference between the $pK_a$ of the hydrophobic acid and the $pK_a$ of the protonated therapeutic agent may be at least about 1 $pK_a$ unit, in some embodiments at least about 2 $pK_a$ units, in some embodiments at least about 3 $pK_a$ units, in some embodiments at least about 4 $pK_a$ units, in some embodiments at least about 5 $pK_a$ units, in some embodiments at least about 6 $pK_a$ units, in some embodiments at least about 7 $pK_a$ units, in some embodiments at least about 8 $pK_a$ units, in some embodiments at least about 9 $pK_a$ units, in some embodiments at least about 10 $pK_a$ units, and in some embodiments at least about 15 $pK_a$ units, determined at 25° C.

In some embodiments, the difference between the $pK_a$ of the hydrophobic acid and the $pK_a$ of the protonated therapeutic agent may be at least 1 $pK_a$ unit, in some embodiments at least 2 $pK_a$ units, in some embodiments at least 3 $pK_a$ units, in some embodiments at least 4 $pK_a$ units, in some embodiments at least 5 $pK_a$ units, in some embodiments at least 6 $pK_a$ units, in some embodiments at least 7 $pK_a$ units, in some embodiments at least 8 $pK_a$ units, in some embodiments at least 9 $pK_a$ units, in some embodiments at least 10 $pK_a$ units, and in some embodiments at least 15 $pK_a$ units, determined at 25° C.

In some embodiments, the hydrophobic acid may have a log P of between about 2 and about 15, in some embodiments between about 5 and about 15, in some embodiments between about 5 and about 10, in some embodiments between about 2 and about 8, in some embodiments between about 4 and about 8, in some embodiments between about 2 and about 7, or in some embodiments between about 4 and about 7. In some instances, the hydrophobic acid may have a log P greater than about 2, greater than about 4, greater than about 5, or greater than about 6.

In some embodiments, the hydrophobic acid may have a log P of between 2 and 15, in some embodiments between 5 and 15, in some embodiments between 5 and 10, in some embodiments between 2 and 8, in some embodiments between 4 and 8, in some embodiments between 2 and 7, or in some embodiments between 4 and 7. In some instances, the hydrophobic acid may have a log P greater than 2, greater than 4, greater than 5, or greater than 6.

In some embodiments, a contemplated hydrophobic acid may have a phase transition temperature that is advantageous, for example, for improving the properties of the therapeutic nanoparticles. For instance, the hydrophobic acid may have a melting point of less than about 350° C., in some cases less than about 300° C., in some cases less than about 100° C., and in some cases less than about 50° C. In certain embodiments, the hydrophobic acid may have a melting point of between about 5° C. and about 25° C., in some cases between about 15° C. and about 50° C., in some cases between about 30° C. and about 100° C., in some cases between about 75° C. and about 150° C., in some cases between about 125° C. and about 200° C., in some cases between about 150° C. and about 250° C., in some cases between about 200° C. and about 300° C., and in some cases between about 250° C. and about 350° C. In some cases, the hydrophobic acid may have a melting point of less than about 15° C., in some cases less than about 10° C., or in some cases less than about 0° C. In certain embodiments, the hydrophobic acid may have a melting point of between about −30° C. and about 0° C. or in some cases between about −20° C. and about −10° C.

In some embodiments, the hydrophobic acid may have a melting point of less than 350° C., in some cases less than 300° C., in some cases less than 100° C., and in some cases less than 50° C. In certain embodiments, the hydrophobic acid may have a melting point of between 5° C. and 25° C., in some cases between 15° C. and 50° C., in some cases between 30° C. and 100° C., in some cases between 75° C. and 150° C., in some cases between 125° C. and 200° C., in some cases between 150° C. and 250° C., in some cases between 200° C. and 300° C., and in some cases between 250° C. and 350° C. In some cases, the hydrophobic acid may have a melting point of less than 15° C., in some cases less than 10° C., or in some cases less than 0° C. In certain embodiments, the hydrophobic acid may have a melting point of between −30° C. and 0° C. or in some cases between −20° C. and −10° C.

For example, hydrophobic acid for use in methods and nanoparticles disclosed herein may be chosen, at least in part, on the basis of the solubility of the therapeutic agent in a solvent comprising the acid. For example, in some embodiments, depending on the solvent, the therapeutic agent dissolved in a solvent comprising the acid may have a solubility of between about 15 mg/mL to about 200 mg/mL, between about 20 mg/mL to about 200 mg/mL, between about 25 mg/mL to about 200 mg/mL, between about 50 mg/mL to about 200 mg/mL, between about 75 mg/mL to about 200 mg/mL, between about 100 mg/mL to about 200 mg/mL, between about 125 mg/mL to about 175 mg/mL, between about 15 mg/mL to about 50 mg/mL, between about 25 mg/mL to about 75 mg/mL. In some embodiments, the therapeutic agent dissolved in a solvent containing the hydrophobic acid may have a solubility greater than about 10 mg/mL, greater than about 50 mg/mL, or greater than about 100 mg/mL. In some embodiments, the therapeutic agent dissolved in a solvent containing the hydrophobic acid (e.g., a first solution consisting of the therapeutic agent, solvent, and hydrophobic acid) may have a solubility of at least about 2 times greater, in some embodiments at least about 5 times greater, in some embodiments at least about 10 times greater, in some embodiments at least about 20 times greater, in some embodiments about 2 times to about 20 times greater or in some embodiments about 10 times to about 20 times greater than when the therapeutic agent is dissolved in a solvent that does not contain the hydrophobic acid (e.g., a second solution consisting of the therapeutic agent and the solvent).

In some embodiments, depending on the solvent, the therapeutic agent dissolved in a solvent comprising the acid may have a solubility of between 15 mg/mL to 200 mg/mL, between 20 mg/mL to 200 mg/mL, between 25 mg/mL to 200 mg/mL, between 50 mg/mL to 200 mg/mL, between 75 mg/mL to 200 mg/mL, between 100 mg/mL to 200 mg/mL, between 125 mg/mL to 175 mg/mL, between 15 mg/mL to 50 mg/mL, between 25 mg/mL to 75 mg/mL. In some embodiments, the therapeutic agent dissolved in a solvent containing the hydrophobic acid may have a solubility greater than 10 mg/mL, greater than 50 mg/mL, or greater than 100 mg/mL. In some embodiments, the therapeutic agent dissolved in a solvent containing the hydrophobic acid (e.g., a first solution consisting of the therapeutic agent, solvent, and hydrophobic acid) may have a solubility of at least 2 times greater, in some embodiments at least 5 times greater, in some embodiments at least 10 times greater, in some embodiments at least 20 times greater, in some embodiments 2 times to 20 times greater or in some embodiments 10 times to 20 times greater than when the therapeutic agent is dissolved in a solvent that does not contain the hydrophobic acid (e.g., a second solution consisting of the therapeutic agent and the solvent).

In some instances, the concentration of hydrophobic acid in a drug solution (i.e., the therapeutic agent solution) may range from about 1 weight percent to about 30 weight percent, in some embodiments, from about 2 weight percent to about 30 weight percent, in some embodiments, from about 3 weight percent to about 30 weight percent, in some embodiments, from about 4 weight percent to about 30 weight percent, in some embodiments, from about 5 weight percent to about 30 weight percent, in some embodiments, from about 6 weight percent to about 30 weight percent, in some embodiments, from about 8 weight percent to about 30 weight percent, in some embodiments, from about 10 weight percent to about 30 weight percent, in some embodiments, from about 12 weight percent to about 30 weight percent, in some embodiments, from about 14 weight percent to about 30 weight percent, in some embodiments, from about 16 weight percent to about 30 weight percent, in some embodiments, from about 1 weight percent to about 5 weight percent, in some embodiments, from about 3 weight percent to about 9 weight percent, in some embodiments, from about 6 weight percent to about 12 weight percent, in some embodiments, from about 9 weight percent to about 15 weight percent, in some embodiments, from about 12 weight percent to about 18 weight percent, and in some embodiments, from about 15 weight percent to about 21 weight percent. In certain embodiments, the concentration of hydrophobic acid in a drug solution may be about 1 weight percent or greater, in some embodiments about 2 weight percent or greater, in some embodiments about 3 weight percent or greater, in some embodiments about 5 weight percent or greater, in some embodiments about 10 weight percent or greater, in some embodiments about 15 weight percent or greater, and in some embodiments about 20 weight percent or greater.

In some instances, the concentration of hydrophobic acid in a drug solution (i.e., the therapeutic agent solution) may range from 1 weight percent to 30 weight percent, in some embodiments, from 2 weight percent to 30 weight percent, in some embodiments, from 3 weight percent to 30 weight percent, in some embodiments, from 4 weight percent to 30 weight percent, in some embodiments, from 5 weight percent to 30 weight percent, in some embodiments, from 6 weight percent to 30 weight percent, in some embodiments, from 8 weight percent to 30 weight percent, in some embodiments, from 10 weight percent to 30 weight percent, in some embodiments, from 12 weight percent to 30 weight percent, in some embodiments, from 14 weight percent to 30 weight percent, in some embodiments, from 16 weight percent to 30 weight percent, in some embodiments, from 1 weight percent to 5 weight percent, in some embodiments, from 3 weight percent to 9 weight percent, in some embodiments, from 6 weight percent to 12 weight percent, in some embodiments, from 9 weight percent to 15 weight percent, in some embodiments, from 12 weight percent to 18 weight percent, and in some embodiments, from 15 weight percent to 21 weight percent. In certain embodiments, the concentration of hydrophobic acid in a drug solution may be 1 weight percent or greater, in some embodiments 2 weight percent or greater, in some embodiments 3 weight percent or greater, in some embodiments 5 weight percent or greater, in some embodiments 10 weight percent or greater, in some embodiments 15 weight percent or greater, and in some embodiments 20 weight percent or greater.

In certain embodiments, the molar ratio of hydrophobic acid to therapeutic agent (e.g., initially during formulation of the nanoparticles and/or in the nanoparticles) may range from about 0.25:1 to about 6:1, in some embodiments from about 0.25:1 to about 5:1, in some embodiments from about 0.25:1 to about 4:1, in some embodiments, from about 0.25:1 to about 3:1, in some embodiments from about 0.25:1 to about 2:1, in some embodiments, from about 0.25:1 to about 1.5:1, in some embodiments, from about 0.25:1 to about 1:1, in some embodiments, from about 0.25:1 to about 0.5:1, in some embodiments from about 0.5:1 to about 6:1, in some embodiments, from about 0.5:1 to about 5:1, in some embodiments, from about 0.5:1 to about 4:1, in some embodiments from about 0.5:1 to about 3:1, in some embodiments from about 0.5:1 to about 2:1, in some embodiments from about 0.5:1 to about 1.5:1, in some embodiments from about 0.5:1 to about 1:1, in some embodiments, from about 0.5:1 to about 0.75:1, in some embodiments, from about 0.75:1 to about 2:1, in some embodiments from about 0.75:1 to about 1.5:1, in some embodiments from about 0.75:1 to about 1.25:1, in some embodiments, from about 0.9:1 to about 1.1:1, in some embodiments, from about 0.95:1 to about 1.05:1, in some embodiments, about 1:1, in some embodiments from about 0.75:1 to about 1:1, in some embodiments from about 1:1 to about 6:1, in some embodiments, from about 1:1 to about 5:1, in some embodiments from about 1:1 to about 4:1, in some embodiments, from about 1:1 to about 3:1, in some embodiments, from about 1:1 to about 2:1, in some embodiments from about 1:1 to about 1.5:1, in some embodiments, from about 1.5:1 to about 6:1, in some embodiments from about 1.5:1 to about 5:1, in some embodiments from about 1.5:1 to about 4:1, in some embodiments from about 1.5:1 to about 3:1, in some embodiments from about 2:1 to about 6:1, in some embodiments from about 2:1 to about 4:1, in some embodiments, from about 3:1 to about 6:1, in some embodiments, from about 3:1 to about 5:1, and in some embodiments, from about 4:1 to about 6:1.

In certain embodiments, the molar ratio of hydrophobic acid to therapeutic agent (e.g., initially during formulation of the nanoparticles and/or in the nanoparticles) may range from 0.25:1 to 6:1, in some embodiments from 0.25:1 to 5:1, in some embodiments from 0.25:1 to 4:1, in some embodiments, from 0.25:1 to 3:1, in some embodiments from 0.25:1 to 2:1, in some embodiments, from 0.25:1 to 1.5:1, in some embodiments, from 0.25:1 to 1:1, in some embodiments, from 0.25:1 to 0.5:1, in some embodiments from 0.5:1 to 6:1, in some embodiments, from 0.5:1 to 5:1, in some embodiments, from 0.5:1 to 4:1, in some embodiments from 0.5:1 to 3:1, in some embodiments from 0.5:1 to 2:1, in some embodiments from 0.5:1 to 1.5:1, in some embodiments from 0.5:1 to 1:1, in some embodiments, from 0.5:1 to 0.75:1, in some embodiments, from 0.75:1 to 2:1, in some embodiments from 0.75:1 to 1.5:1, in some embodiments, from 0.75:1 to 1.25:1, in some embodiments, from 0.9:1 to 1.1:1, in some embodiments, from 0.95:1 to 1.05:1, in some embodiments, 1:1, in some embodiments from 0.75:1 to 1:1, in some embodiments from 1:1 to 6:1, in some embodiments, from 1:1 to 5:1, in some embodiments from 1:1 to 4:1, in some embodiments, from 1:1 to 3:1, in some embodiments, from 1:1 to 2:1, in some embodiments from 1:1 to 1.5:1, in some embodiments, from 1.5:1 to 6:1, in some embodiments, from 1.5:1 to 5:1, in some embodiments from 1.5:1 to 4:1, in some embodiments from 1.5:1 to 3:1, in some embodiments from 2:1 to 6:1, in some embodiments from 2:1 to 4:1, in some embodiments, from 3:1 to 6:1, in some embodiments, from 3:1 to 5:1, and in some embodiments, from 4:1 to 6:1.

In some instances, the initial molar ratio of hydrophobic acid to therapeutic agent (i.e., during formulation of the nanoparticles) may be different from the molar ratio of hydrophobic acid to therapeutic agent in the nanoparticles (i.e., after removal of unencapsulated hydrophobic acid and therapeutic agent). In other instances, the initial molar ratio of hydrophobic acid to therapeutic agent (i.e., during formulation of the nanoparticles) may be essentially the same as the molar ratio of hydrophobic acid to therapeutic agent in the nanoparticles (i.e., after removal of unencapsulated hydrophobic acid and therapeutic agent).

In an embodiment, when the nanoparticle contains the hydrophobic acid, the nanoparticle comprising the therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea may form a salt with the hydrophobic acid. In other words, the hydrophobic acid associated with the therapeutic agent is the pharmaceutically acceptable salt. Thus, in an embodiment, the present invention relates to a therapeutic nanoparticle comprising therapeutic agent or a pharmaceutically acceptable salt thereof and a polymer selected from diblock poly(lactic) acid-poly(ethylene)glycol copolymer or a diblock poly(lactic acid-co-glycolic acid)-poly(ethylene)glycol copolymer and combination thereof, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea.

In some cases, a solution containing the therapeutic agent may be prepared separately from a solution containing the polymer, and the two solutions may then be combined prior to nanoparticle formulation. For instance, in one embodiment, a first solution contains the therapeutic agent and the hydrophobic acid, and a second solution contains the polymer and optionally the hydrophobic acid. Formulations where the second solution does not contain the hydrophobic acid may be advantageous, for example, for minimizing the amount of hydrophobic acid used in a process or, in some cases, for minimizing contact time between the hydrophobic acid and, e.g., a polymer that can degrade in the presence of the hydrophobic acid. In other cases, a single solution may be prepared containing the therapeutic agent, polymer, and hydrophobic acid.

In some embodiments, the hydrophobic ion pair may be formed prior to formulation of the nanoparticles. For example, a solution containing the hydrophobic ion pair may be prepared prior to formulating the contemplated nanoparticles (e.g., by preparing a solution containing suitable amounts of the therapeutic agent and the hydrophobic acid). In other embodiments, the hydrophobic ion pair may be formed during formulation of the nanoparticles. For example, a first solution containing the therapeutic agent and a second solution containing the hydrophobic acid may be combined during a process step for preparing the nanoparticles (e.g., prior to emulsion formation and/or during emulation formation). In certain embodiments, the hydrophobic ion pair may form prior to encapsulation of the therapeutic agent and hydrophobic acid in a contemplated nanoparticle. In other embodiments, the hydrophobic ion pair may form in the nanoparticle, e.g., after encapsulation of the therapeutic agent and hydrophobic acid.

In certain embodiments, the hydrophobic acid may have a solubility of less than about 2 g per 100 mL of water or less, in some embodiments about 1 g per 100 mL of water or less; in some embodiments, about 100 mg per 100 mL of water or less, in some embodiments, about 10 mg per 100 mL of water or less, and in some embodiments about 1 mg per 100 mL of water or less, determined at 25° C. In other embodiments, the hydrophobic acid may have a solubility ranging from about 1 mg per 100 mL of water to about 2 g per 100 mL of water; in some embodiments from about 1 mg per 100 mL of water to about 1 g per 100 mL of water, in some embodiments, from about 1 mg per 100 mL of water to about 500 mg per 100 mL of water, and in some embodiments from about 1 mg per 100 mL of water to about 100 mg per 100 mL of water, determined at 25° C. In some embodiments, the hydrophobic acid may be essentially insoluble in water at 25° C.

In certain embodiments, the hydrophobic acid may have a solubility of less than 2 g per 100 mL of water or less, in some embodiments 1 g per 100 mL of water or less; in some embodiments, 100 mg per 100 mL of water or less, in some embodiments, 10 mg per 100 mL of water or less, and in some embodiments 1 mg per 100 mL of water or less, determined at 25° C. In other embodiments, the hydrophobic acid may have a solubility ranging from 1 mg per 100 mL of water to 2 g per 100 mL of water; in some embodiments from 1 mg per 100 mL of water to 1 g per 100 mL of water, in some embodiments, from 1 mg per 100 mL of water to 500 mg per 100 mL of water, and in some embodiments from 1 mg per 100 mL of water to 100 mg per 100 mL of water, determined at 25° C. In some embodiments, the hydrophobic acid may be essentially insoluble in water at 25° C.

In some embodiments, disclosed nanoparticles may be essentially free of the hydrophobic acid used during the preparation of the nanoparticles. In other embodiments, disclosed nanoparticles may comprise the hydrophobic acid. For instance, in some embodiments, the acid content in disclosed nanoparticles may range from about 0.05 weight percent to about 35 weight percent, in some embodiments from about 0.05 weight percent to about 30 weight percent, in some embodiments from about 0.05 weight percent to about 20 weight percent, in some embodiments, from about 0.5 weight percent to about 30 weight percent, in some embodiments from about 1 weight percent to about 30 weight percent, in some embodiments from about 2 weight percent to about 30 weight percent, in some embodiments from about 3 weight percent to about 30 weight percent, in some embodiments, from about 5 weight percent to about 30 weight percent, in some embodiments, from about 7 weight percent to about 30 weight percent, in some embodiments, from about 10 weight percent to about 30 weight percent, in some embodiments, from about 15 weight percent to about 25 weight percent, in some embodiments, from about 15 weight percent to about 30 weight percent, in some embodiments, from about 20 weight percent to about 30 weight percent, in some embodiments, from about 0.05 weight percent to about 0.5 weight percent, in some embodiments, from about 0.05 weight percent to about 5 weight percent, in some embodiments, from about 1 weight percent to about 5 weight percent, in some embodiments from about 3 weight percent to about 10 weight percent, in some embodiments, from about 1 weight percent to about 10 weight percent, in some embodiments, from about 5 weight percent to about 10 weight percent, in some embodiments, from about 5 weight percent to about 15 weight percent, and in some embodiments, from about 10 weight percent to about 20 weight percent.

In some embodiments, the acid content in disclosed nanoparticles may range from 0.05 weight percent to 35 weight percent, in some embodiments from 0.05 weight percent to 30 weight percent, in some embodiments from 0.05 weight percent to 20 weight percent, in some embodiments, from 0.5 weight percent to 30 weight percent, in some embodiments from 1 weight percent to 30 weight percent, in some embodiments from 2 weight percent to 30 weight percent, in some embodiments from 3 weight percent to 30 weight percent, in some embodiments, from 5 weight percent to 30 weight percent, in some embodiments, from 7 weight percent to 30 weight percent, in some embodiments, from 10 weight percent to 30 weight percent, in some embodiments, from 15 weight percent to 25 weight percent, in some embodiments, from 15 weight percent to 30 weight percent, in some embodiments, from 20 weight percent to 30 weight percent, in some embodiments, from 0.05 weight percent to 0.5 weight percent, in some embodiments, from 0.05 weight percent to 5 weight percent, in some embodiments, from 1 weight percent to 5 weight percent, in some embodiments from 3 weight percent to 10 weight percent, in some embodiments, from about 1 weight percent to about 10 weight percent, in some embodiments, from about 5 weight percent to about 10 weight percent, in some embodiments, from 5 weight percent to 15 weight percent, and in some embodiments, from 10 weight percent to 20 weight percent.

In some embodiments, disclosed nanoparticles substantially immediately release (e.g., from about 1 minute to about 30 minutes, about 1 minute to about 25 minutes, about 5 minutes to about 30 minutes, about 5 minutes to about 1 hour, about 1 hour, or about 24 hours). In other cases, the release profile is slower: about 2% or less; about 5% or less; about 10% or less; about 15% or less; about 20% or less; about 25% or, about 30% or less about 40% or less of the therapeutic agent, by weight is released for example, when placed in a phosphate buffer solution, e.g. a buffer comprising monobasic and dibasic phosphate buffer (such as 0.138 M sodium chloride, 0.0027 M potassium chloride, about 0.02 M monobasic sodium or potassium phosphate and about 0.01 M sodium or potassium dibasic phosphate buffer dissolved in 1 liter of water, e.g., RODI water), at room temperature (e.g., 25° C.) and/or at 37° C. In certain embodiments, nanoparticles comprising the therapeutic agent may release the therapeutic agent when placed in an aqueous solution (e.g., a phosphate buffer solution, such as described herein above) e.g., at 25° C. and/or at 37° C., at a rate substantially corresponding to about 0.01 to about 50%, in some embodiments about 0.01 to about 25%, in some embodiments about 0.01 to about 15%, in some embodiments about 0.01 to about 10%, in some embodiments about 1 to about 40%, in some embodiments about 5 to about 40%, and in some embodiments about 10 to about 40% of the therapeutic agent released by weight over about 1 hour. In some embodiments, nanoparticles comprising the therapeutic agent may release the therapeutic agent when placed in an aqueous solution (e.g., a phosphate buffer solution), e.g., at 25° C. and/or at 37° C., at a rate substantially corresponding to about 10 to about 70%, in some embodiments 10 to about 45%, in some embodiments about 10 to about 35%, or in some embodiments about 10 to about 25%, therapeutic agent, released by weight over about 4 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to about 0.01 to about 50%, in some embodiments about 0.01 to about 25%, in some embodiments about 0.01 to about 15%, in some embodiments about 0.01 to about 10%, in some embodiments about 0.01 to about 5%, and in some embodiments about 0.01 to about 3% of the therapeutic agent released by weight over about 4 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to about 0.01 to about 60%, in some embodiments about 0.01 to about 25%, in some embodiments about 0.01 to about 15%, in some embodiments about 0.01 to about 10%, in some embodiments about 0.01 to about 5%, and in some embodiments about 0.01 to about 3% of the therapeutic agent released by weight over about 10 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to about 0.01 to about 70%, in some embodiments about 0.01 to about 50%, in some embodiments about 0.01 to about 25%, in some embodiments about 0.01 to about 15%, in some embodiments about 0.01 to about 10%, in some embodiments about 0.01 to about 5%, and in some embodiments about 0.01 to about 3% of the therapeutic agent released by weight over about 20 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to about 1 to about 80%, in some embodiments about 1 to about 50%, in some embodiments about 1 to about 30%, in some embodiments about 1 to about 25%, in some embodiments about 1 to about 15%, in some embodiments about 1 to about 10%, and in some embodiments about 1 to about 5% of the therapeutic agent released by weight over about 40 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to about 10 to about 100%, in some embodiments about 10 to about 80%, in some embodiments about 10 to about 70%, in some embodiments about 10 to about 60%, in some embodiments about 10 to about 50%, in some embodiments about 10 to about 40%, in some embodiments about 10 to about 30%, in some embodiments about 10 to about 20% of the therapeutic agent released by weight over about 100 hours.

In some embodiments, disclosed nanoparticles substantially immediately release (e.g., from 1 minute to 30 minutes, 1 minute to 25 minutes, 5 minutes to 30 minutes, 5 minutes to 1 hour, 1 hour, or 24 hours). In other cases, the release profile is slower: 2% or less; 5% or less; 10% or less; 15% or less; 20% or less; 25% or, 30% or less 40% or less of the therapeutic agent, by weight is released for example, when placed in a phosphate buffer solution, e.g. a buffer comprising monobasic and dibasic phosphate buffer (such as 0.138 M sodium chloride, 0.0027 M potassium chloride, about 0.02 M monobasic sodium or potassium phosphate and about 0.01 M sodium or potassium dibasic phosphate buffer dissolved in 1 liter of water, e.g., RODI water), at room temperature (e.g., 25° C.) and/or at 37° C. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to 0.01 to 50%, in some embodiments 0.01 to 25%, in some embodiments 0.01 to 15%, in some embodiments 0.01 to 10%, in some embodiments 1 to 40%, in some embodiments 5 to 40%, and in some embodiments 10 to 40% of the therapeutic agent released by weight over 1 hour. In some embodiments, nanoparticles comprising the therapeutic agent may release the therapeutic agent when placed in an aqueous solution (e.g., a phosphate buffer solution), e.g., at 25° C. and/or at 37° C., at a rate substantially corresponding to 10 to 70%, in some embodiments 10 to 45%, in some embodiments 10 to 35%, or in some embodiments 10 to 25%, therapeutic agent, released by weight over 4 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to 0.01 to 50%, in some embodiments 0.01 to 25%, in some embodiments 0.01 to 15%, in some embodiments 0.01 to 10%, in some embodiments 0.01 to 5%, and in some embodiments 0.01 to 3% of the therapeutic agent released by weight over 4 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to 0.01 to 60%, in some embodiments 0.01 to 25%, in some embodiments 0.01 to 15%, in some embodiments 0.01 to 10%, in some embodiments 0.01 to 5%, and in some embodiments 0.01 to 3% of the therapeutic agent released by weight over 10 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to 0.01 to 70%, in some embodiments 0.01 to 50%, in some embodiments 0.01 to 25%, in some embodiments 0.01 to 15%, in some embodiments 0.01 to 10%, in some embodiments 0.01 to 5%, and in some embodiments 0.01 to 3% of the therapeutic agent released by weight over 20 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding 1 to 80%, in some embodiments 1 to 50%, in some embodiments 1 to 30%, in some embodiments 1 to 25%, in some embodiments 1 to 15%, in some embodiments 1 to 10%, and in some embodiments 1 to 5% of the therapeutic agent released by weight over 40 hours. In certain embodiments, nanoparticles comprising the therapeutic agent may release the therapeutic agent when placed in an aqueous solution (e.g., a phosphate buffer solution, such as described hereinabove) e.g., at 25° C. and/or at 37° C., at a rate substantially corresponding to 10 to 100%, in some embodiments 10 to 80%, in some embodiments 10 to 70%, in some embodiments 10 to 60%, in some embodiments 10 to 50%, in some embodiments 10 to 40%, in some embodiments 10 to 30%, in some embodiments 10 to 20% of the therapeutic agent released by weight over 100 hours.

In some embodiments, disclosed nanoparticles may substantially retain the therapeutic agent, e.g., for at least about 1 minute, at least about 1 hour, or more, when placed in a phosphate buffer solution at 37° C.

In some embodiments, disclosed nanoparticles may substantially retain the therapeutic agent, e.g., for at least 1 minute, at least 1 hour, or more, when placed in a phosphate buffer solution at 37° C.

In one embodiment, disclosed therapeutic nanoparticles may include a targeting ligand, e.g., a low-molecular weight ligand. In certain embodiments, the low-molecular weight ligand is conjugated to a polymer, and the nanoparticle comprises a certain ratio of ligand-conjugated polymer (e.g., PLA-PEG-Ligand) to non-functionalized polymer (e.g., PLA-PEG or PLGA-PEG). The nanoparticle can have an effective ratio of these two polymers such that an effective amount of ligand is associated with the nanoparticle for treatment of a disease or disorder, such as cancer. For example, an increased ligand density may increase target binding (cell binding/target uptake), making the nanoparticle "target specific." Alternatively, a certain concentration of non-functionalized polymer (e.g., non-functionalized PLGA-PEG copolymer) in the nanoparticle can control inflammation and/or immunogenicity (i.e., the ability to provoke an immune response), and allow the nanoparticle to have a circulation half-life that is adequate for the treatment of a disease or disorder. For instance, in an embodiment, the molar ratio of non-functionalized polymer to the ligand conjugated polymer ranges from about 0.01 to about 0.1 and in another embodiment, from about 0.01 to about 0.05, such as, e.g. about 0.025. Furthermore, the non-functionalized polymer may, in some embodiments, lower the rate of clearance from the circulatory system via the reticuloendothelial system (RES). Thus, the non-functionalized polymer may provide the nanoparticle with characteristics that may allow the particle to travel through the body upon administration. In some embodiments, a non-functionalized polymer may balance an otherwise high concentration of ligands, which can otherwise accelerate clearance by the subject, resulting in less delivery to the target cells.

In another embodiment, the molar ratio of non-functionalized polymer to the ligand conjugated polymer ranges from 0.01 to 0.1 and in another embodiment, from 0.01 to 0.05, such as, e.g. 0.025.

In some embodiments, nanoparticles disclosed herein may include functionalized polymers conjugated to a ligand that constitute a range from approximately 0.1 to about 50, e.g., about 0.1 to about 30, e.g., about 0.1 to about 20, e.g., about 0.1 to about 10 mole percent of the entire polymer composition of the nanoparticle (i.e., functionalized+non-functionalized polymer). Also disclosed herein, in another embodiment, are nanoparticles that include a polymer conjugated (e.g., covalently with (i.e., through a linker (e.g., an alkylene linker)) or a bond) with one or more low-molecular weight ligands, wherein the weight percent low-molecular weight ligand with respect to total polymer is ranges from about 0.001 to about 5, e.g., from about 0.001 to about 2, e.g., from and about 0.001 to about 1.

In some embodiments, nanoparticles disclosed herein may include functionalized polymers conjugated to a ligand that constitute a range from 0.1-50, e.g., 0.1-30, e.g., 0.1-20, e.g., 0.1-10 mole percent of the entire polymer composition of the nanoparticle (i.e., functionalized+non-functionalized polymer). Also disclosed herein are nanoparticles that include a polymer conjugated with one or more low-molecular weight ligands, wherein the weight percent low-molecular weight ligand with respect to total polymer is ranges from 0.001 to 5, e.g., from 0.001 to 2, e.g., from and 0.001 to 1.

In general, a "nanoparticle" refers to any particle having a diameter of less than 1000 nm, e.g., about 10 nm to about 200 nm. Disclosed therapeutic nanoparticles may include nanoparticles having a diameter ranging from about 60 to about 120 nm, or from about 70 to about 120 nm, or from about 80 to about 120 nm, or from about 90 to about 120 nm, or from about 100 to about 120 nm, or from about 60 to about 130 nm, or from about 70 to about 130 nm, or from about 80 to about 130 nm, or from about 90 to about 130 nm, or from about 100 to about 130 nm, or from about 110 to about 130 nm, or from about 60 to about 140 nm, or from about 70 to about 140 nm, or from about 80 to about 140 nm, or from about 90 to about 140 nm, or from about 100 to about 140 nm, or from about 110 to about 140 nm, or from about 60 to about 150 nm, or from about 70 to about 150 nm, or from about 80 to about 150 nm, or from about 90 to about 150 nm, or from about 100 to about 150 nm, or from about 110 to about 150 nm, or from about 120 to about 150 nm.

Disclosed therapeutic nanoparticles may include nanoparticles having a diameter ranging from 60 to 120 nm, or from 70 to 120 nm, or from 80 to 120 nm, or from 90 to 120 nm, or from 100 to 120 nm, or from 60 to 130 nm, or from 70 to 130 nm, or from 80 to 130 nm, or from 90 to 130 nm, or from 100 to 130 nm, or from 110 to 130 nm, or from 60 to 140 nm, or from 70 to 140 nm, or from 80 to 140 nm, or from 90 to 140 nm, or from 100 to 140 nm, or from 110 to 140 nm, or from 60 to 150 nm, or from 70 to 150 nm, or from 80 to 150 nm, or from 90 to 150 nm, or from 100 to 150 nm, or from 110 to 150 nm, or from 120 to 150 nm.

Polymers

In some embodiments, the nanoparticles may comprise a matrix of polymers and the therapeutic agent. In some embodiments, the therapeutic agent and/or targeting moiety (i.e., a low-molecular weight ligand) can be associated with at least part of the polymeric matrix. For example, in some embodiments, a targeting moiety (e.g., ligand) can be covalently associated with the surface of a polymeric matrix. In some embodiments, covalent association is mediated by a linker. The therapeutic agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g., targeting moiety); and the second macromolecule comprising a second polymer that is not bound to a targeting moiety. The nanoparticle can optionally include one or more additional, non-non-functionalized, polymers.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example, biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describe two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a non-biocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise taken up by such cells. Non-limiting examples of biocompatible polymers that may be useful in various embodiments include polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid) (PLA), poly(lactic) acid-co-poly(glycolic) acid (PLGA), polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., $R^{100}$—C(O)—O—$R^1$ bonds) and ether bonds (e.g., $R^1$—O—$R^1$ bonds wherein $R^{100}$ and $R^1$ are independently hydrocarbyl moieties which may optionally be substituted and which may be the same or different). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

For instance, a contemplated polymer may be one that hydrolyzes spontaneously upon exposure to water (e.g., within a subject), or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid molar ratio of approximately 85:15, approximately 75:25, approximately 60:40, approximately 50:50, approximately 40:60, approximately 25:75, or approximately 15:85. In some embodiments, the molar ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight (or e.g., the ratio of molecular weights of, e.g., different blocks of a copolymer) of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer (or e.g., the ratio of molecular weights of, e.g., different blocks of a copolymer) can be adjusted such that the particle biodegrades in the subject being treated within a reasonable period of time (ranging from a few hours to 1-2 weeks, 3-4 weeks, 5-6 weeks, 7-8 weeks, etc.).

A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes from about 10 to about 99 weight percent poly(lactic) acid-poly(ethylene)glycol copolymer or poly(lactic)-co-poly (glycolic) acid-poly(ethylene)glycol copolymer, or from about 50 to about 99.75 weight percent, from about 20 to about 80 weight percent, from about 40 to about 80 weight percent, or from about 30 to about 50 weight percent, or from about 70 to about 90 weight percent, from about 70 to about 99.75 weight percent, from about 80 to about 99.75 weight percent, from about 70 to about 80 weight percent, or from about 85 to about 95 weight percent poly(lactic) acid-poly(ethylene)glycol copolymer or poly (lactic)-co-poly (glycolic) acid-poly(ethylene)glycol copolymer. In some embodiments, a therapeutic nanoparticle comprises about 50 weight percent, about 55 weight percent, about 60 weight percent, about 65 weight percent, about 70 weight percent, about 75 weight percent, about 80 weight percent, about 85 weight percent, about 90 weight percent or about 95 weight percent poly(lactic) acid-poly(ethylene) glycol copolymer or poly(lactic)-co-poly (glycolic) acid-poly(ethylene)glycol copolymer. Exemplary poly(lactic) acid-poly(ethylene)glycol copolymers can include a number average molecular weight ranging from about 15 to about 20 kDa, or from about 10 to about 25 kDa of poly(lactic) acid and a number average molecular weight from about 4 kDa to about 6 kDa, from about 4 kDa to about 10 kD, from about 6 kDa to about 10 kDa, or from about 2 kDa to about 10 kDa of poly(ethylene)glycol.

In another example, disclosed here is an exemplary therapeutic nanoparticle that includes from 10 to 99 weight percent poly(lactic) acid-poly(ethylene)glycol copolymer or poly(lactic)-co-poly (glycolic) acid-poly(ethylene)glycol copolymer, or from 50 to 99.75 weight percent, from 20 to 80 weight percent, from 40 to 80 weight percent, or from 30 to 50 weight percent, or from 70 to 90 weight percent, from 70 to 99.75 weight percent, from 80 to 99.75 weight percent, from 70 to 80 weight percent, or from 85 to 95 weight percent poly(lactic) acid-poly(ethylene)glycol copolymer or poly(lactic)-co-poly (glycolic) acid-poly(ethylene)glycol copolymer. In some embodiments, a therapeutic nanoparticle comprises 50 weight percent, 55 weight percent, 60 weight percent, 65 weight percent, 70 weight percent, 75 weight percent, 80 weight percent, 85 weight percent, 90 weight percent or 95 weight percent poly(lactic) acid-poly (ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight ranging from 15 to 20 kDa, or from 10 to 25 kDa of poly(lactic) acid and a number average molecular weight from 4 kDa to 6 kDa, from 4 kDa to 10 kD, from 6 kDa to 10 kDa, or from 2 kDa to 10 kDa of poly(ethylene)glycol.

In some embodiments, the poly(lactic) acid-poly(ethylene)glycol copolymer may have a poly(lactic) acid number average molecular weight fraction of from about 0.6 to about 0.95, in some embodiments, from about 0.7 to about 0.9, in some embodiments, from about 0.6 to about 0.8, in some embodiments, from about 0.7 to about 0.8, in some embodiments, from about 0.75 to about 0.85, in some embodiments from about 0.8 to about 0.9, and in some embodiments, from about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly(ethylene)glycol component.

In some embodiments, the poly(lactic) acid-poly(ethylene)glycol copolymer may have a poly(lactic) acid number average molecular weight fraction of from 0.6 to 0.95, in some embodiments, from 0.7 to 0.9, in some embodiments, from 0.6 to 0.8, in some embodiments, from 0.7 to 0.8, in some embodiments, from 0.75 to 0.85, in some embodiments from 0.8 to 0.9, and in some embodiments, from 0.85 to 0.95.

In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of about 1:7. In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of about 1:4. In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of about 1:14. In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of about 1:3.

In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of 1:7. In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of 1:4. In certain embodiments, the therapeutic nanoparticle comprises 1-(4-{[4-(dimethylamino)piperidin-1-yl]carbonyl}phenyl)-3-[4-(4,6-dimorpholin-4-yl-1,3,5-triazin-2-yl)phenyl]urea and PLA-PEG (in a 16:5 molar ratio) in a weight ratio of 1:14. In certain embodiments, the therapeutic nanoparticle comprises 1-(4-{[4-(dimethylamino)piperidin-1-yl]carbonyl}phenyl)-3-[4-(4,6-dimorpholin-4-yl-1,3, 5-triazin-2-yl)phenyl]urea and PLA-PEG (in a 16:5 molar ratio) in a weight ratio of 1:3.

Disclosed nanoparticles may optionally include about 1 to about 50 weight percent poly(lactic) acid or poly(lactic) acid-co-poly (glycolic) acid (which does not include PEG), or may optionally include from about 1 to about 50 weight percent, or from about 10 to about 50 weight percent or from about 30 to about 50 weight percent poly(lactic) acid or poly(lactic) acid-co-poly (glycolic) acid. For example, poly (lactic) or poly(lactic)-co-poly(glycolic) acid may have a number average molecule weight ranging from about 5 to about 15 kDa, or from about 5 to about 12 kDa. Exemplary PLA may have a number average molecular weight ranging from about 5 to about 10 kDa. Exemplary PLGA may have a number average molecular weight ranging from about 8 to about 12 kDa.

Disclosed nanoparticles may optionally include 1 to 50 weight percent poly(lactic) acid or poly(lactic) acid-co-poly (glycolic) acid (which does not include PEG), or may optionally include from 1 to 50 weight percent, or from 10 to 50 weight percent or from 30 to 50 weight percent poly(lactic) acid or poly(lactic) acid-co-poly (glycolic) acid. For example, poly(lactic) or poly(lactic)-co-poly(glycolic) acid may have a number average molecule weight ranging from 5 to 15 kDa, or from 5 to 12 kDa. Exemplary PLA may have a number average molecular weight ranging from 5 to 10 kDa. Exemplary PLGA may have a number average molecular weight ranging from 8 to 12 kDa.

A therapeutic nanoparticle may, in some embodiments, contain from about 10 to about 30 weight percent, from about 10 to about 25 weight percent, from about 10 to about 20 weight percent, from about 10 to about 15 weight percent, from about 15 to about 20 weight percent, from about 15 to about 25 weight percent, from about 20 to about 25 weight percent, from about 20 to about 30 weight percent, or from about 25 to about 30 weight percent of poly(ethylene)glycol, where the poly(ethylene)glycol may be present as a poly (lactic) acid-poly(ethylene)glycol copolymer, poly(lactic)-co-poly (glycolic) acid-poly(ethylene)glycol copolymer, or poly(ethylene)glycol homopolymer. In certain embodiments, the polymers of the nanoparticles can be conjugated to a lipid. The polymer can be, for example, a lipid-terminated PEG.

A therapeutic nanoparticle may, in some embodiments, contain from 10 to 30 weight percent, from 10 to 25 weight percent, from 10 to 20 weight percent, from 10 to 15 weight percent, from 15 to 20 weight percent, from 15 to 25 weight percent, from 20 to 25 weight percent, from 20 to 30 weight percent, or from 25 to 30 weight percent of poly(ethylene) glycol, where the poly(ethylene)glycol may be present as a poly(lactic) acid-poly(ethylene)glycol copolymer, poly(lactic)-co-poly (glycolic) acid-poly(ethylene)glycol copolymer, or poly(ethylene)glycol homopolymer.

In certain embodiments, the therapeutic nanoparticle comprises the polymer PLA-PEG and the mole ratio of PLA-PEG is about 5:1. In other embodiments, the therapeutic nanoparticle comprises the polymer PLA-PEG and the mole ratio of PLA-PEG is 5:1.

Targeting Moieties

Provided herein, in some embodiments, are nanoparticles that may include an optional targeting moiety, i.e., a moiety able to bind to or otherwise associate with a biological entity, for example, a membrane component, a cell surface receptor, an antigen, or the like. A targeting moiety present on the surface of the particle may allow the particle to become localized at a particular targeting site, for instance, a tumor, a disease site, a tissue, an organ, a type of cell, etc. As such, the nanoparticle may then be "target specific." The drug or other payload may then, in some cases, be released from the particle and allowed to interact locally with the particular targeting site.

In one embodiment, a disclosed nanoparticle includes a targeting moiety that is a low-molecular weight ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

In some embodiments, the targeting moiety has an affinity (as measured via a disassociation constant) of less than 1 micromolar, at least 10 micromolar, or at least 100 micromolar.

For example, a targeting portion may cause the particles to become localized to a tumor (e.g., a solid tumor), a disease site, a tissue, an organ, a type of cell, etc. within the body of a subject, depending on the targeting moiety used. For example, a low-molecular weight ligand may become localized to a solid tumor, e.g., breast or prostate tumors or cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

Contemplated targeting moieties may include small molecules. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are about 2000 g/mol or less in size. In some embodiments, small molecules are about 1500 g/mol or less, or about 1000 g/mol or less. In some embodiments, small molecules are about 800 g/mol or less, 500 g/mol or less, for example from about 100 g/mol to about 600 g/mol, or from about 200 g/mol to about 500 g/mol.

In certain embodiments, small molecules are 2000 g/mol or less in size. In some embodiments, small molecules are 1500 g/mol or less, or 1000 g/mol or less. In some embodiments, small molecules are 800 g/mol or less, 500 g/mol or less, for example from 100 g/mol to 600 g/mol, or from 200 g/mol to 500 g/mol.

In some embodiments, the low-molecular weight ligand is of the Formulae I, II, III or IV:

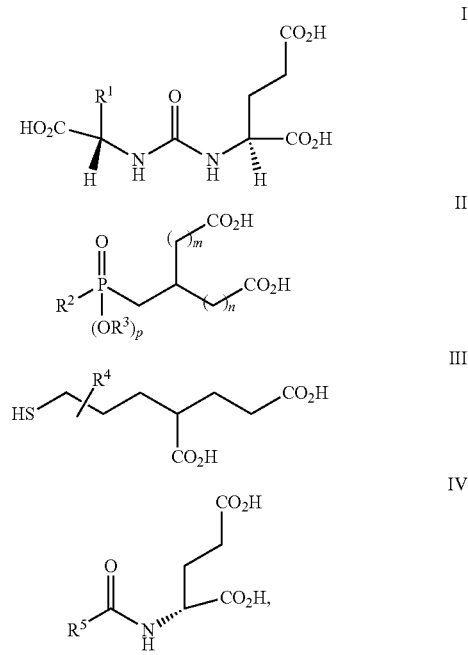

and enantiomers, stereoisomers, rotamers, tautomers, diastereomers, or racemates thereof;

wherein m and n are each, independently, 0, 1, 2 or 3; p is 0 or 1;

$R^1$, $R^2$, $R^4$, and $R^5$ are each, independently, selected from the group consisting of substituted or unsubstituted alkyl (e.g., $C_{1-10}$-alkyl, $C_{1-6}$-alkyl, or $C_{1-4}$-alkyl), substituted or unsubstituted aryl (e.g., phenyl or pyridinyl), and any combination thereof; and $R^3$ is H or $C_{1-6}$-alkyl (e.g., $CH_3$).

For compounds of Formulae I, II, III and IV, $R^1$, $R^2$, $R^4$ or $R^5$ comprise points of attachment to the nanoparticle, e.g., a point of attachment to a polymer that forms part of a disclosed nanoparticle, e.g., PEG. The point of attachment may be formed by a covalent bond, ionic bond, hydrogen bond, a bond formed by adsorption including chemical adsorption and physical adsorption, a bond formed from van der Waals bonds, or dispersion forces. For example, if $R^1$, $R^2$, $R^4$, or $R^5$ are defined as an aniline or $C_{1-6}$-alkyl-$NH_2$ group, any hydrogen (e.g., an amino hydrogen) of these functional groups could be removed such that the low-molecular weight ligand is covalently bound to the polymeric matrix (e.g., the PEG-block of the polymeric matrix) of the nanoparticle. As used herein, the term "covalent bond" refers to a bond between two atoms formed by sharing at least one pair of electrons.

In particular embodiments of the Formulae I, II, III or IV, $R^1$, $R^2$, $R^4$, and $R^5$ are each, independently, $C_{1-6}$-alkyl or phenyl, or any combination of $C_{1-6}$-alkyl or phenyl, which are independently substituted one or more times with OH, SH, $NH_2$, or $CO_2H$, and wherein the alkyl group may be interrupted by N(H), S, or O. In another embodiment, $R^1$, $R^2$, $R^4$, and $R^5$ are each, independently, $CH_2$-Ph, $(CH_2)_2$—SH, $CH_2$—SH, $(CH_2)_2C(H)(NH_2)CO_2H$, $CH_2C(H)(NH_2)CO_2H$, $CH(NH_2)CH_2CO_2H$, $(CH_2)_2C(H)(SH)CO_2H$, $CH_2$—N(H)-Ph, O—$CH_2$-Ph, or O—$(CH_2)_2$-Ph, wherein Ph is phenyl, and wherein each Ph may be independently substituted one or more times with OH, $NH_2$, $CO_2H$, or SH. For these formulae, the $NH_2$, OH or SH groups serve as the point of covalent attachment to the nanoparticle (e.g., —N(H)—PEG, —O-PEG, or —S-PEG).

Exemplary ligands include:

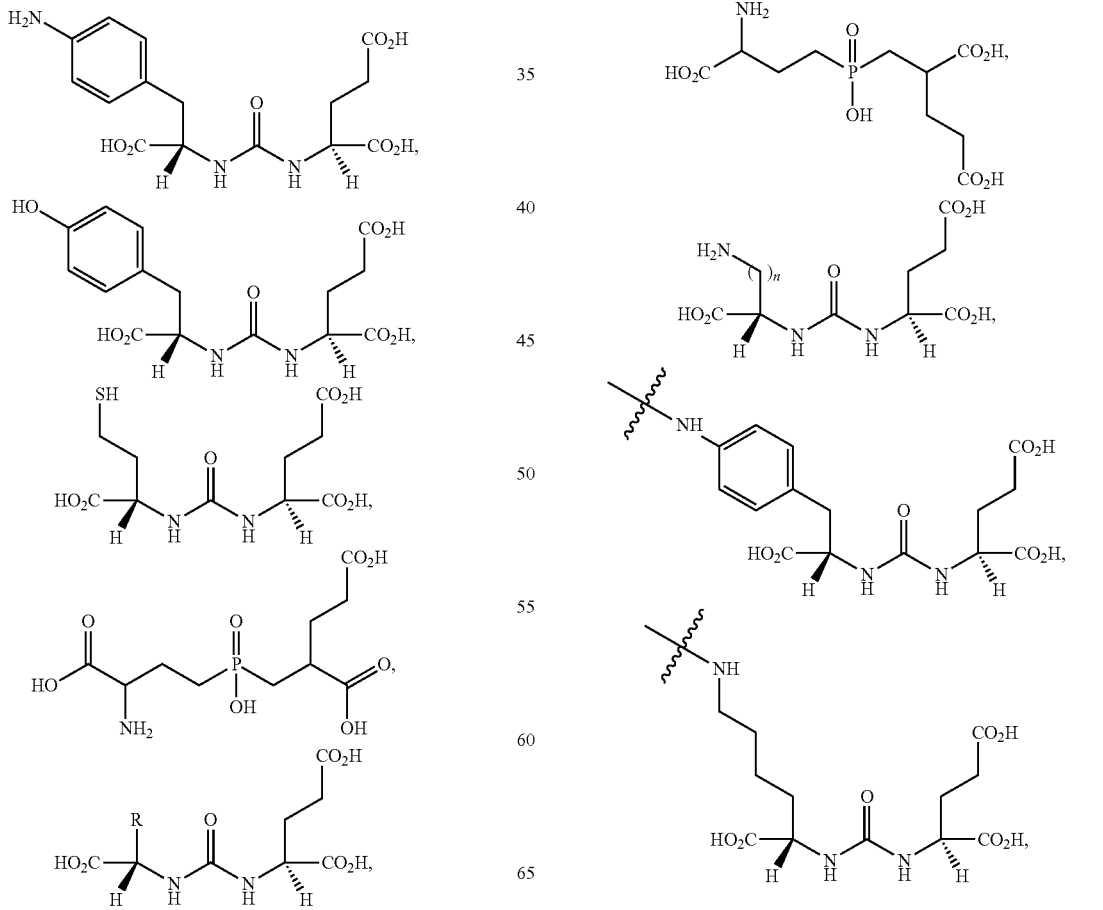

and enantiomers, stereoisomers, rotamers, tautomers, diastereomers, or racemates thereof, wherein the NH$_2$, OH, or SH groups serve as the point of covalent attachment to the nanoparticle (e.g., —N(H)—PEG, —O-PEG, or —S-PEG) or

indicates the point of attachment to the nanoparticle, wherein n is 1, 2, 3, 4, 5, or 6, and wherein R is independently selected from the group consisting of NH$_2$, SH, OH, CO$_2$H, C$_{1-6}$-alkyl that is substituted with NH$_2$, SH, OH, or CO$_2$H, and phenyl that is substituted with NH$_2$, SH, OH, or CO$_2$H, and wherein R serves as the point of covalent attachment to the nanoparticle (e.g., —N(H)—PEG, —S-PEG, —O-PEG, or CO$_2$-PEG). These compounds may be further substituted with NH$_2$, SH, OH, CO$_2$H, C$_{1-6}$-alkyl that is substituted with NH$_2$, SH, OH, or CO$_2$H, or phenyl that is substituted with NH$_2$, SH, OH or CO$_2$H, wherein these functional groups can also serve as the point of covalent attachment to the nanoparticle.

In some embodiments, small molecule targeting moieties that may be used to target cells associated with solid tumors such as prostate or breast cancer tumors include PSMA peptidase inhibitors such as 2-PMPA, GPI5232, VA-033, phenylalkylphosphonamidates and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives. In some embodiments, small molecule targeting moieties that may be used to target cells associated with prostate cancer tumors include hydroxamate derivatives. In some embodiments, small molecule targeting moieties that may be used to target cells associated with prostate cancer tumors include PBDA- and urea-based inhibitors, such as ZJ 43, ZJ 11, ZJ 17, ZJ 38 and/or and analogs and derivatives thereof, androgen receptor targeting agents (ARTAs), polyamines, such as putrescine, spermine, and spermidine, inhibitors of the enzyme glutamate carboxylase II (GCPII), also known as NAAG Peptidase or NAALADase.

In another embodiment, the targeting moiety can be a ligand that targets Her2, EGFR, folate receptor or toll receptors. In another embodiment, the targeting moiety is folate, folic acid, or an EGFR binding molecule.

For example, contemplated the targeting moieties may include a nucleic acid, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments. Characteristic portions of antibodies, single chain targeting moieties can be identified, e.g., using procedures such as phage display.

Targeting moieties disclosed herein can be, in some embodiments, conjugated to a disclosed polymer or copolymer (e.g., PLA-PEG), and such a polymer conjugate may form part of a disclosed nanoparticle.

In certain embodiments, the therapeutic nanoparticle has a targeting ligand additionally present and the ligand is PLA-PEG-GL, wherein GL has the following structure:

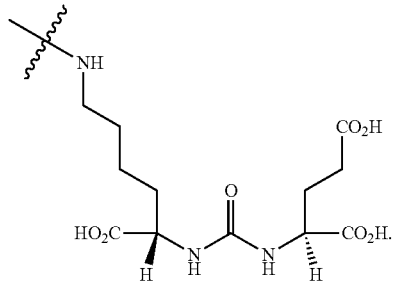 [SMILES: *NCCCC[C@H](NC(=O)N[C@@H](CCC(=O)O)C(=O)O)C(=O)O]

In some embodiments, a therapeutic nanoparticle may include a polymer-drug conjugate. For example, a drug may be conjugated to a disclosed polymer or copolymer (e.g., PLA-PEG), and such a polymer-drug conjugate may form part of a disclosed nanoparticle. For example, a disclosed therapeutic nanoparticle may optionally include from about 0.2 to about 30 weight percent of a PLA-PEG or PLGA-PEG, wherein the PEG is functionalized with a drug (e.g., PLA-PEG-Drug).

In another example, a disclosed therapeutic nanoparticle may optionally include from 0.2 to 30 weight percent of a PLA-PEG or PLGA-PEG, wherein the PEG is functionalized with a drug (e.g., PLA-PEG-Drug).

A disclosed polymeric conjugate (e.g., a polymer-ligand conjugate) may be formed using any suitable conjugation technique. For instance, two compounds such as a targeting moiety or drug and a biocompatible polymer (e.g., a biocompatible polymer and a poly(ethylene glycol)) may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of a targeting moiety or drug and a polymer to form a polymer-targeting moiety conjugate or a polymer-drug conjugate can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety or therapeutic drug) having an amine functionality thereon. For instance, a targeting moiety, such as a low-molecular weight ligand, or the therapeutic agent as may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. In some embodiments, the therapeutic agent may be reacted with an amine-containing linker to form an amine-containing drug, which can then be conjugated to the carboxylic acid of the polymer as described above. The conjugation reaction between the amine-containing moiety and the carboxylic acid-terminated polymer (such as a poly (ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethylsulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol. In certain embodiments, a conjugate may be formed between an alcohol-containing moiety and carboxylic acid functional group of a polymer, which can be achieved similarly as described above for conjugates of amines and carboxylic acids.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, one polymer (e.g., copolymer, e.g., block copolymer) may include a low-molecular weight ligand, while another polymer (e.g., copolymer, e.g., block copolymer) may be chosen for its biocompatibility and/or its ability to control immunogenicity of the resultant particle.

In some embodiments, a solvent used in a nanoparticle preparation process (e.g., a nanoprecipitation process or a nanoemulsion process as discussed below) may include a hydrophobic acid, which may confer advantageous properties to the nanoparticles prepared using the process. As discussed above, in some cases, the hydrophobic acid may improve drug loading of disclosed nanoparticles. Furthermore, in some instances, the controlled release properties of disclosed nanoparticles may be improved by the use of the hydrophobic acid. In some cases, the hydrophobic acid may be included in, for example, an organic solution or an aqueous solution used in the process. In one embodiment, the therapeutic agent is combined with an organic solution and the hydrophobic acid and optionally one or more polymers. The hydrophobic acid concentration in a solution used to dissolve the therapeutic agent is discussed above and may, for example, range from about 1 weight percent and about 30 weight percent or from 1 weight percent and 30 weight percent, etc.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Properties such as surface functionality, surface charge, size, zeta ($\zeta$) potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties (e.g., low-molecular weight ligands) present on the surface of the particle. This allows particles having one or more specific properties to be prepared, for example, a specific size and a specific surface density of moieties, without an undue degree of effort. Accordingly, certain embodiments are directed to screening techniques using such libraries, as well as any particles identified using such libraries. In addition, identification may occur by any suitable method. For instance, the identification may be direct or indirect, or proceed quantitatively or qualitatively.

In some embodiments, already-formed nanoparticles are functionalized with a targeting moiety using procedures analogous to those described for producing ligand-functionalized polymeric conjugates. For example, a first copolymer (PLGA-PEG, poly(lactide-co-glycolide) and poly(ethylene glycol)) is mixed with the protonatable nitrogen-containing therapeutic agent to form particles. The particles are then associated with a low-molecular weight ligand to form nanoparticles that can be used for the treatment of cancer. The particles can be associated with varying amounts of low-molecular weight ligands in order to control the ligand surface density of the nanoparticle, thereby altering the therapeutic characteristics of the nanoparticle. Furthermore, for example, by controlling parameters such as molecular weight, the molecular weight of PEG, and the nanoparticle surface charge, very precisely controlled particles may be obtained.

Figure 2A:
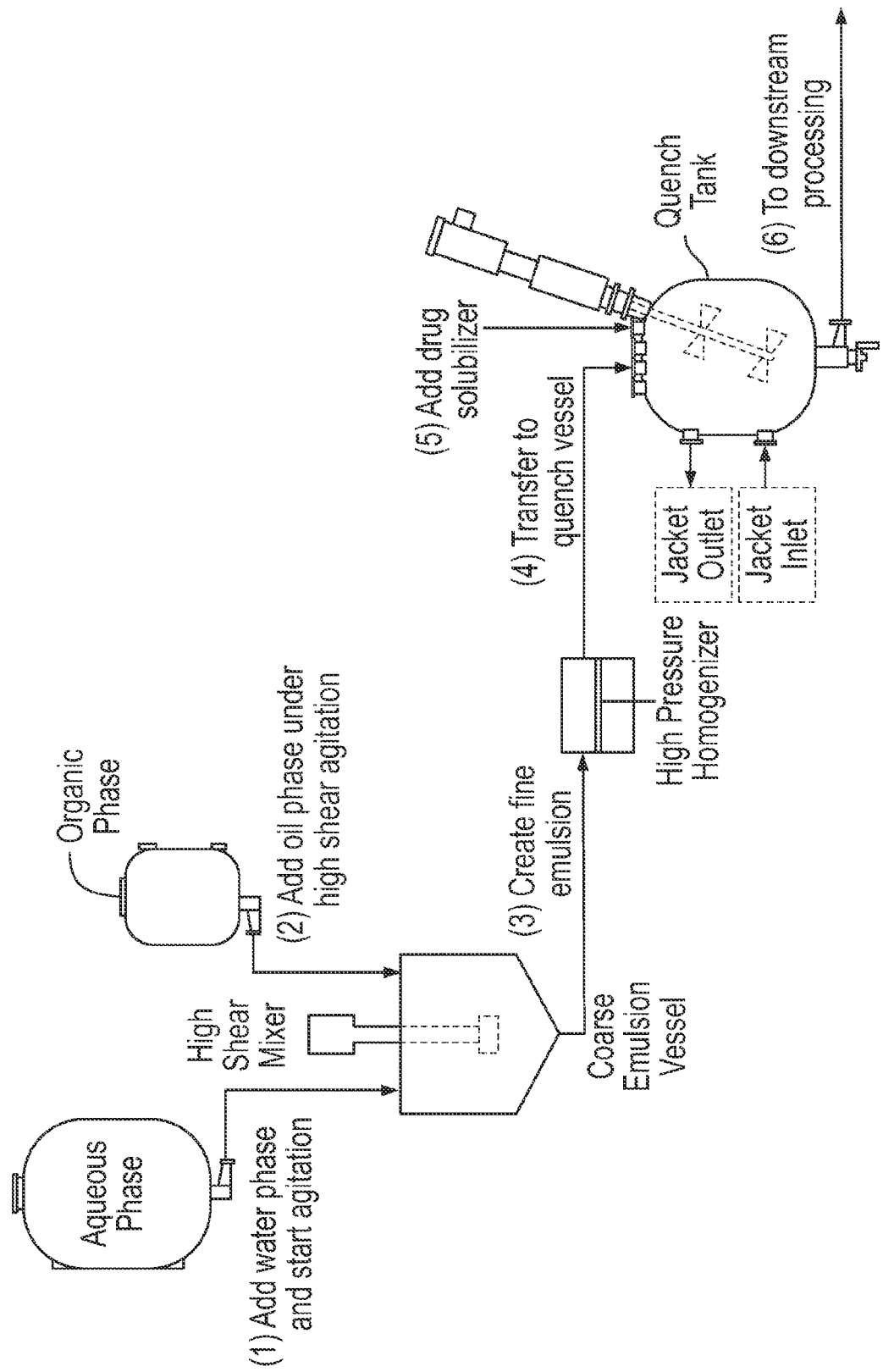
FIGS. 2A and 2B show flow diagrams for a disclosed emulsion process.
Figure 2B:
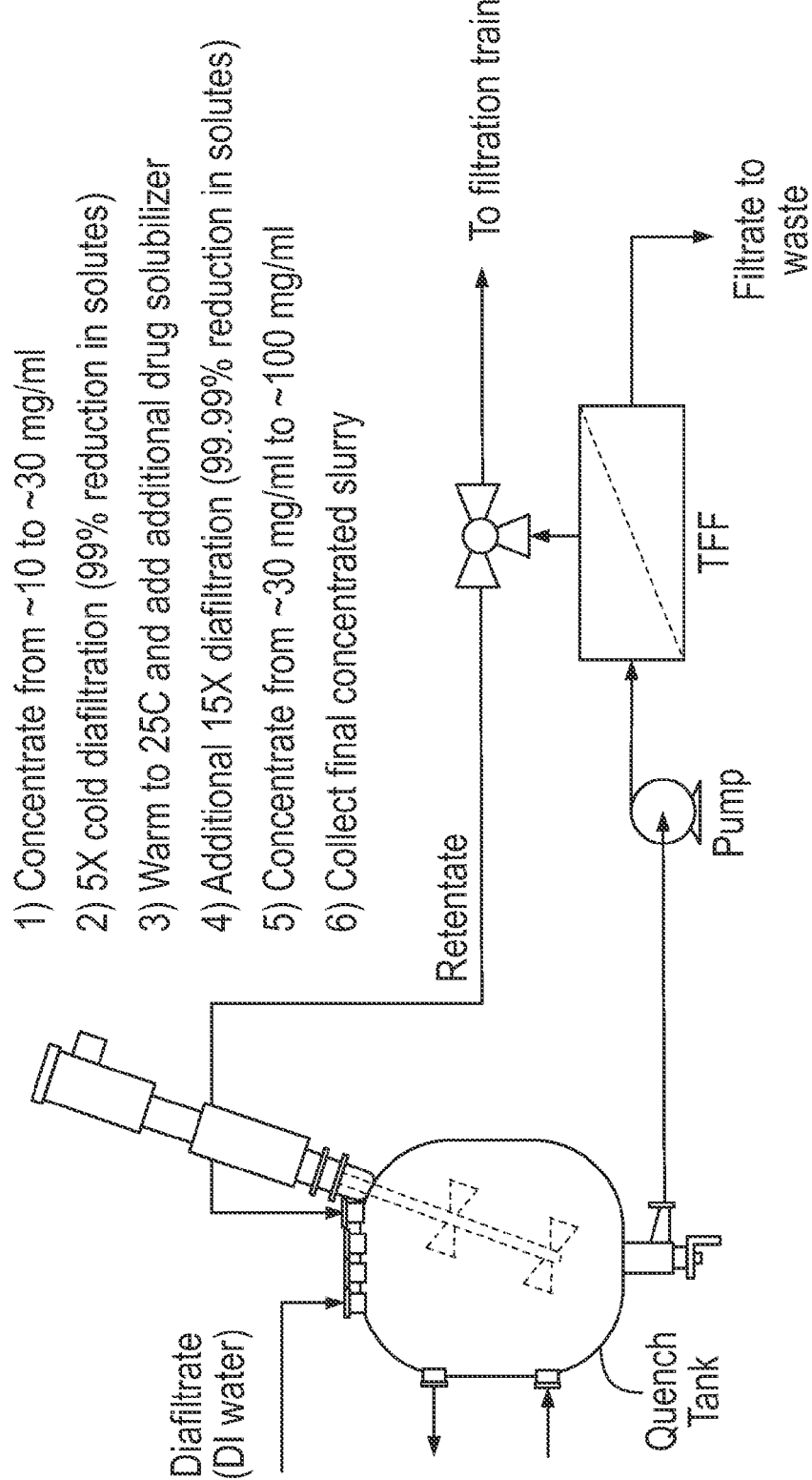

In another embodiment, a nanoemulsion process is provided, such as the process represented in FIGS. 1, 2A, and 2B. For example, a the therapeutic agent, a hydrophobic acid, a first polymer (for example, a diblock co-polymer such as PLA-PEG or PLGA-PEG, either of which may be optionally bound to a ligand) and an optional second polymer (e.g., (PL(G)A-PEG or PLA), may be combined with an organic solution to form a first organic phase. Such first phase may include about 1 to about 50% weight solids, about 5 to about 50% weight solids, about 5 to about 40% weight solids, about 1 to about 15% weight solids, or about 10 to about 30% weight solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween™ 80, Span 80, or the like, and combinations thereof. In an embodiment, the organic phase may include benzyl alcohol, ethyl acetate, and combinations thereof. The second phase can range from about 0.1 and 50 weight %, or from about 1 and 50 weight %, or from about 5 and 40 weight %, or from about 1 and 15 weight %, solids. The aqueous solution can be water, optionally in combination with one or more of sodium cholate, ethyl acetate, polyvinyl acetate and benzyl alcohol. In some embodiments, the pH of the aqueous phase may be selected based on the $pK_a$ of the protonoated basic therapeutic agent and/or the $pK_a$ of the hydrophobic acid. For example, in certain embodiments, the therapeutic agent, when protonated, may have a first $pK_a$, the hydrophobic acid may have a second $pK_a$, and the aqueous phase may have a pH equal to a $pK_a$ unit between the first $pK_a$ and the second $pK_a$. In a particular embodiment, the pH of the aqueous phase may be equal to a $pK_a$ unit that is about equidistant between the first $pK_a$ and the second $pK_a$.

In another embodiment, the first phase may include 1 to 50% weight solids, 5 to 50% weight solids, 5 to 40% weight solids, 1 to 15% weight solids, or 10 to 30% weight solids. In an embodiment, the second phase can range from 0.1 and 50 weight %, or from 1 and 50 weight %, or from 5 and 40 weight %, or from 1 and 15 weight %, solids. In a particular embodiment, the pH of the aqueous phase may be equal to a $pK_a$ unit that is equidistant between the first $pK_a$ and the second $pK_a$.

For example, the oil or organic phase may use a solvent that is only partially miscible with the nonsolvent (water). Therefore, when mixed at a low enough ratio and/or when using water pre-saturated with the organic solvents, the oil phase remains liquid. The oil phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate and pre-saturated with ethyl acetate and benzyl alcohol. In some instances, the organic phase (e.g., first organic phase) may include the basic therapeutic agent. Additionally, in certain embodiments, the aqueous solution (e.g., first aqueous solution) may include the substantially hydrophobic acid. In other embodiments, both the basic therapeutic agent and the substantially hydrophobic acid may be dissolved in the organic phase.

Emulsifying the second phase to form an emulsion phase may be performed, for example, in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3, or more passes through a homogenizer. For example, when a high pressure homogenizer is used, the pressure used may be about 30 to about 60 psi, about 40 to about 50 psi, about 1000 to about 8000 psi, about 2000 to about 4000 psi, about 4000 to about 8000 psi, or about 4000 to about 5000 psi, e.g., about 2000, 2500, 4000 or 5000 psi.

In another example, when a high pressure homogenizer is used, the pressure used may be 30 to 60 psi, 40 to 50 psi, 1000 to 8000 psi, 2000 to 4000 psi, 4000 to 8000 psi, or 4000 to 5000 psi, e.g., 2000, 2500, 4000 or 5000 psi.

In some cases, fine emulsion conditions, which can be characterized by a very high surface to volume ratio of the droplets in the emulsion, can be chosen to maximize the solubility of the therapeutic agent and hydrophobic acid and form the desired HIP. In certain embodiments, under fine emulsion conditions, equilibration of dissolved components can occur very quickly, i.e., faster than solidification of the nanoparticles. Thus, selecting a HIP based on, e.g., the $pK_a$ difference between the protonated form of the therapeutic agent and the hydrophobic acid, or adjusting other parameters such as the pH of the fine emulsion and/or the pH of the quench solution, can have a significant impact on the drug loading and release properties of the nanoparticles by dictating, for example, the formation of a HIP in the nanoparticle as opposed to diffusion of the therapeutic agent and/or hydrophobic acid out of the nanoparticle.

In some embodiments, the therapeutic agent and the substantially hydrophobic acid may be combined in the second phase prior to emulsifying the second phase. In some instances, the therapeutic agent and the substantially hydrophobic acid may form a hydrophobic ion pair prior to emulsifying the second phase. In other embodiments, the therapeutic agent and the substantially hydrophobic acid may form a hydrophobic ion pair during emulsification of the second phase. For example, the therapeutic agent and the substantially hydrophobic acid may be combined in the second phase substantially concurrently with emulsifying the second phase, e.g., the therapeutic agent and the substantially hydrophobic acid may be dissolved in separate solutions (e.g., two substantially immiscible solutions), which are then combined during emulsification. In another example, the therapeutic agent and the substantially hydrophobic acid may be dissolved in separate miscible solutions that are then fed into second phase during emulsification.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. In some embodiments, quenching may be performed at least partially at a temperature of about 5° C. or less. For example, water used in the quenching may be at a temperature that is less that room temperature (e.g., about 0 to about 10° C., or about 0 to about 5° C.). In certain embodiments, the quench may be chosen having a pH that is advantageous for quenching the emulsion phase, e.g., by improving the properties of the nanoparticles, such as the release profile, or improving a nanoparticle parameter, such as the drug loading. The pH of the quench may be adjusted by acid or base titration, for example, or by appropriate selection of a buffer. In some embodiments, the pH of the quench may be selected based on the $pK_a$ of the protonoated basic therapeutic agent and/or the $pK_a$ of the hydrophobic acid. For example, in certain embodiments, the basic therapeutic agent, when protonated, may have a first $pK_a$, the hydrophobic acid may have a second $pK_a$, and the emulsion phase may be quenched with an aqueous solution having a pH equal to a $pK_a$ unit between the first $pK_a$ and the second $pK_a$. In some embodiments, the resultant quenched phase may also have a pH equal to a $pK_a$ unit between the first $pK_a$ and the second $pK_a$. In a particular embodiment, the pH may be equal to a $pK_a$ unit that is about equidistant between the first $pK_a$ and the second $pK_a$.

In certain embodiments, HIP formation can occur during or after emulsification, e.g., as a result of equilibrium conditions in the fine emulsion. Without wishing to be bound by any theory, it is believed that organic-soluble counter ions (i.e., the hydrophobic acid) can facilitate diffusion of the therapeutic agent into a nanoparticle of an emulsion as a result of HIP formation.

Without wishing to be bound by any theory, the HIP may remain in the nanoparticle before solidification of the nanoparticle since the solubility of the HIP in the nanoparticle is higher than the solubility of the HIP in the aqueous phase of the emulsion and/or in the quench. For example, by selecting a pH for the quench that is between the $pK_a$ of the basic therapeutic agent and the $pK_a$ of the hydrophobic acid, formation of ionized therapeutic agent and hydrophobic acid can be optimized. However, selecting a pH that is too high may tend to cause the hydrophobic acid to diffuse out of the nanoparticle, whereas selecting a pH that is too low may tend to cause the therapeutic agent to diffuse out of the nanoparticle.

In some embodiments, the pH of an aqueous solution used in a nanoparticle formulation process (e.g., including, but not limited to, the aqueous phase, the emulsion phase, the quench, and the quenched phase) may be independently selected and may be range from about 1 to about 3, in some embodiments from about 2 to about 4, in some embodiments, from about 3 to about 5, in some embodiments, from about 4 to about 6, in some embodiments, from about 5 to about 7, in some embodiments, from about 6 to about 8, in some embodiments, from about 7 to about 9, and in some embodiments, from about 8 to about 10. In certain embodiments, the pH of an aqueous solution used in a nanoparticle formulation process may range from about 3 to about 4, in some embodiments from about 4 to about 5, in some embodiments, from about 5 to about 6, in some embodiments from about 6 to about 7, in some embodiments from about 7 to about 8, and in some embodiments from about 8 to about 9.

In some embodiments, the pH of an aqueous solution used in a nanoparticle formulation process (e.g., including, but not limited to, the aqueous phase, the emulsion phase, the quench, and the quenched phase) may be independently selected and may be range from 1 to 3, in some embodiments from 2 to 4, in some embodiments, from 3 to 5, in some embodiments, from 4 to 6, in some embodiments, from 5 to 7, in some embodiments, from 6 to 8, in some embodiments, from 7 to 9, and in some embodiments, from 8 to 10. In certain embodiments, the pH of an aqueous solution used in a nanoparticle formulation process may range from 3 to 4, in some embodiments from 4 to 5, in some embodiments, from 5 to 6, in some embodiments from 6 to 7, in some embodiments from 7 to 8, and in some embodiments from 8 to 9.

In some embodiments, not all of the therapeutic agent is encapsulated in the particles at this stage, and a drug solubilizer is added to the quenched phase to form a solubilized phase. The drug solubilizer may be for example, polysorbate 80 (Tween™ 80), Tween™ 20, polyvinyl pyrrolidone, cyclodextran, sodium dodecyl sulfate, sodium cholate, diethylnitrosamine, sodium acetate, urea, glycerin, propylene glycol, glycofurol, poly(ethylene)glycol, bris(polyoxyethyleneglycol)dodecyl ether, sodium benzoate, sodium salicylate, polyoxyethylene (100) stearyl ether, or combinations thereof. For example, Tween™ 80 may be added to the quenched nanoparticle suspension to solubilize the free drug and prevent the formation of drug crystals. In some embodiments, a ratio of drug solubilizer to the protonatable nitrogen-containing therapeutic agent is about 200:1 to about 10:1, or in some embodiments about 100:1 to about 10:1.

In some embodiments, a ratio of drug solubilizer to the protonatable nitrogen-containing therapeutic agent is 200:1 to 10:1, or in some embodiments 100:1 to 10:1.

The solubilized phase may be filtered to recover the nanoparticles. For example, ultrafiltration membranes may be used to concentrate the nanoparticle suspension and substantially eliminate organic solvent, free drug (i.e., unencapsulated therapeutic agent), drug solubilizer, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of ranging about 300 to about 500 kDa (~from about 5 to about 25 nm) may be used. Exemplary membranes with molecular weight cut-offs of ranging 300 to 500 kDa (~from 5 to 25 nm) may be used.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. In some embodiments, filtering may include processing about 1 to about 30, in some cases about 1 to about 15, or in some cases 1 to about 6 diavolumes. For example, filtering may include processing about 1 to about 30, or in some cases about 1 to about 6 diavolumes, at about 0 to about 5° C., and processing at least one diavolume (e.g., about 1 to about 15, about 1 to about 3, or about 1 to about 2 diavolumes) at about 20 to about 30° C. In some embodiments, filtering comprises processing different diavolumes at different distinct temperatures.

In some embodiments, filtering may include a first filtering using a first temperature of 0 to 5° C., or 0 to 10° C., and a second temperature of 20 to 30° C., or 15 to 35° C. In some embodiments, filtering may include processing 1 to 30, in some cases 1 to 15, or in some cases 1 to 6 diavolumes. For example, filtering may include processing 1 to 30, or in some cases 1 to 6 diavolumes, at 0 to 5° C., and processing at least one diavolume (e.g., 1 to 15, 1 to 3, or 1 to 2 diavolumes) at 20 to 30° C.

After purifying and concentrating the nanoparticle suspension, the particles may be passed through one, two or more sterilizing and/or depth filters, for example, using ~0.2 μm depth pre-filter. For example, a sterile filtration step may involve filtering the therapeutic nanoparticles using a filtration train at a controlled rate. In some embodiments, the filtration train may include a depth filter and a sterile filter.

In another embodiment of preparing nanoparticles, an organic phase is formed composed of a mixture of the therapeutic agent, and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. In some embodiments, the quench:emulsion ratio may be about 2:1 to about 40:1, or in some about 5:1 to about 15:1. In some embodiments, the quench:emulsion ratio is approximately 8.5:1. In some embodiments, the quench:emulsion ratio may be 2:1 to 40:1, or in some embodiments 5:1 to 15:1. In some embodiments, the quench:emulsion ratio is 8.5:1. Then a solution of Tween™ (e.g., Tween™ 80) is added to the quench to achieve approximately 2% Tween™ overall. This serves to dissolve free, unencapsulated therapeutic agent. The nanoparticles are then isolated through either centrifugation or ultrafiltration/diafiltration.

It will be appreciated that the amounts of polymer, therapeutic agent, and hydrophobic acid that are used in the preparation of the formulation may differ from a final formulation. For example, some of the therapeutic agent may not become completely incorporated in a nanoparticle and such free therapeutic agent may be e.g., filtered away. For example, in an embodiment, a first organic solution containing about 11 weight percent theoretical loading of therapeutic agent in a first organic solution containing about 9% of a first hydrophobic acid (e.g., a fatty acid), a second organic solution containing about 89 weight percent polymer (e.g., the polymer may include about 2.5 mol percent of a targeting moiety conjugated to a polymer and about 97.5 mol percent PLA-PEG), and an aqueous solution containing about 0.12% of a second hydrophobic acid (e.g., a bile acid) may be used in the preparation of a formulation that results in, e.g., a final nanoparticle comprising about 2 weight percent therapeutic agent, about 97.5 weight percent polymer (where the polymer may include about 1.25 mol percent of a targeting moiety conjugated to a polymer and about 98.75 mol percent PLA-PEG), and about 0.5% total hydrophobic acid. Such processes may provide final nanoparticles suitable for administration to a subject that includes about 1 to about 20 percent by weight therapeutic agent, e.g., about 1, about 2, about 3, about 4, about 5, about 8, about 10, or about 15 percent therapeutic agent by weight.

In another embodiment, a first organic solution containing 11 weight percent theoretical loading of therapeutic agent in a first organic solution containing 9% of a first hydrophobic acid (e.g., a fatty acid), a second organic solution containing 89 weight percent polymer (e.g., the polymer may include 2.5 mol percent of a targeting moiety conjugated to a polymer and 97.5 mol percent PLA-PEG), and an aqueous solution containing 0.12% of a second hydrophobic acid (e.g., a bile acid) may be used in the preparation of a formulation that results in, e.g., a final nanoparticle comprising 2 weight percent therapeutic agent, 97.5 weight percent polymer (where the polymer may include 1.25 mol percent of a targeting moiety conjugated to a polymer and 98.75 mol percent PLA-PEG), and 0.5% total hydrophobic acid. Such processes may provide final nanoparticles suitable for administration to a subject that includes 1 to 20 percent by weight therapeutic agent, e.g., 1, 2, 3, 4, 5, 8, 10, or 15 percent therapeutic agent by weight.

In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea and pamoic acid in a weight ratio of therapeutic agent to pamoic acid of about 0.1:1, about 0.5:1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, or about 10:1. In some embodiments, the therapeutic nanoparticle comprises PLA-PEG (in a 16:5 molar ratio) in a weight ratio of therapeutic agent to PLA-PEG of about 0.5:1, about 1:1, about 1:2, about 1:3, about 1:4, about 1:5, about 1:6, about 1:7, about 1:8, about 1:9, about 1:10, about 1:15, or about 1:20. In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea, pamoic acid in a weight ratio of therapeutic agent to pamoic acid of about 1.8:1, PLA-PEG (in a 16:5 molar ratio) in a weight ratio of therapeutic agent to PLA-PEG of about 1:3, and PLA-PEG-GL in a weight ratio of PLA-PEG to PLA-PEG-GL of about 44:1. In other embodiments, the therapeutic nanoparticle additionally comprises a solubilizer. In certain such embodiments, the solubilizer is polyoxyethylene (100) stearyl ether. In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea and pamoic acid in a weight ratio of therapeutic agent to pamoic acid of 0.1:1, 0.5:1, 1:1, 1.1:1, 1.2:1, 1.3:1, 1.4:1, 1.5:1, 1.6:1, 1.7:1, 1.8:1, 1.9:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1. In some embodiments, the therapeutic nanoparticle comprises PLA-PEG (in a 16:5 molar ratio) in a weight ratio of therapeutic agent to PLA-PEG of 0.5:1, 1:1, 1:2, 1:3, 1:4, 1:5, 1:6, 1:7, 1:8, 1:9, 1:10, 1:15, or 1:20. In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea, pamoic acid in a weight ratio of therapeutic agent to pamoic acid of 1.8:1, PLA-PEG (in a 16:5 molar ratio) in a weight ratio of therapeutic agent to PLA-PEG of 1:3, and PLA-PEG-GL in a weight ratio of PLA-PEG to PLA-PEG-GL of 44:1. In other embodiments, the therapeutic nanoparticle additionally comprises a solubilizer. In certain such embodiments, the solubilizer is polyoxyethylene (100) stearyl ether.

In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea and oleic acid in a weight ratio of therapeutic agent to oleic acid of about 0.1:1, about 0.5:1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, or about 10:1. In some embodiments, the therapeutic nanoparticle comprises PLA-PEG (in a 16:5 molar ratio) in a weight ratio of therapeutic agent to PLA-PEG of about 0.5:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:20, about 1:25, or about 1:30. In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea, oleic acid in a weight ratio of therapeutic agent to oleic acid of about 6:1, PLA-PEG (in a 16:5 molar ratio) in a weight ratio of therapeutic agent to PLA-PEG of about 1:7, and PLA-PEG-GL in a weight ratio of PLA-PEG to PLA-PEG-GL of about 46:1. In some embodiments, the therapeutic nanoparticle further comprises cholic acid. In other embodiments, the therapeutic nanoparticle additionally comprises a solubilizer. In certain such embodiments, the solubilizer is polysorbate 80. In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea and oleic acid in a weight ratio of therapeutic agent to oleic acid of 0.1:1, 0.5:1, 1:1, 1.1:1, 1.2:1, 1.3:1, 1.4:1, 1.5:1, 1.6:1, 1.7:1, 1.8:1, 1.9:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1. In some embodiments, the therapeutic nanoparticle comprises PLA-PEG (in a 16:5 molar ratio) in a weight ratio of therapeutic agent to PLA-PEG of 0.5:1, 1:1, 1:2, 1:3, 1:4, 1:5, 1:6, 1:7, 1:8, 1:9, 1:10, 1:11, 1:12, 1:13, 1:14, 1:15, 1:20, 1:25, or 1:30. In certain embodiments, the therapeutic nanoparticle comprises the therapeutic agent 1-(4-{[4-(dimethylamino)piperidin-1-yl]carbonyl}phenyl)-3-[4-(4,6-dimorpholin-4-yl-1,3,5-triazin-2-yl)phenyl]urea, oleic acid in a weight ratio of therapeutic agent to oleic acid of 6:1, PLA-PEG (in a 16:5 molar ratio) in a weight ratio of therapeutic agent to PLA-PEG of 1:7, and PLA-PEG-GL in a weight ratio of PLA-PEG to PLA-PEG-GL of 46:1. In some embodiments, the therapeutic nanoparticle further comprises cholic acid. In other embodiments, the therapeutic nanoparticle additionally comprises a solubilizer. In certain such embodiments, the solubilizer is polysorbate 80.

In some embodiments, the therapeutic nanoparticle is a nanoparticle prepared by emulsification of a first organic phase comprising a first polymer, a therapeutic agent, and a substantially hydrophobic acid, thereby forming an emulsion phase; quenching of the emulsion phase thereby forming a quenched phase; and filtration of the quenched phase to recover the therapeutic nanoparticles, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.

In other embodiments, the therapeutic nanoparticle is a nanoparticle prepared by the process combining a first organic phase with a first aqueous solution to form a second phase; emulsifying the second phase to form an emulsion phase, wherein the emulsion phase comprises a first polymer, therapeutic agent, and a substantially hydrophobic acid; quenching of the emulsion phase thereby forming a quenched phase; and filtering the quenched phase to recover the therapeutic nanoparticles, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea, the first organic phase comprises the therapeutic agent and pamoic acid in a weight ratio of therapeutic agent to pamoic acid of about 11:1 and PLA-PEG (in a 16:5 molar ratio) in a weight ratio of therapeutic agent to PLA-PEG of about 1:3 in an organic solvent comprising of benzyl alcohol and ethyl acetate in a weight ratio of benzyl alcohol to ethyl acetate of about 1.25 and the first aqueous solution comprises a polyoxyethylene (100) stearyl ether dissolved in benzyl alcohol in a weight ratio of 0.005:1 and combining the first organic phase and the first aqueous phase in a weight ratio of about 1:5 to form a second phase and emulsifying the second phase formed therefrom and quenching the emulsion phase with 0.1 M citric acid in water solution at pH 4.5 and concentrating the resulting product.

The therapeutic agent may include alternative forms such as pharmaceutically acceptable salt forms, free base forms, hydrates, isomers, and prodrugs thereof.

An "effective amount" when used in connection with a compound of this invention is an amount effective for inhibiting mTOR or PI3K in a subject.

The therapeutic agent of the present invention exhibits an mTOR inhibitory activity and therefore, the therapeutic nanoparticle prepared from the therapeutic agent can be utilized to inhibit abnormal cell growth in which mTOR plays a role. Thus, the therapeutic nanoparticle of the present invention is effective in the treatment of disorders with which abnormal cell growth actions of mTOR are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, advanced renal cell carcinoma, acute lymphoblastic leukemia, malignant melanoma, soft-tissue or bone sarcoma, etc.

The therapeutic agent of the present invention exhibits a PI3 kinase inhibitory activity and, therefore, the therapeutic nanoparticle prepared from the therapeutic agent can be utilized to inhibit abnormal cell growth in which PI3 kinases play a role. Thus, the therapeutic agent of the present invention are effective in the treatment of disorders with which abnormal cell growth actions of PI3 kinases are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the therapeutic nanoparticle of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, head and neck cancer e.g., cancer of the following regions: Oral cavity, Pharynx, Larynx, Paranasal sinuses and nasal cavity, or Salivary glands), advanced renal cell carcinoma, acute lymphoblastic leukemia, malignant melanoma, soft-tissue or bone sarcoma, etc.

The therapeutic agent is also useful in treating a cancer associated with PTEN deficiency. Phosphatase and tensin homolog deleted on chromosome 10 (PTEN) is a lipid and protein phosphatase and functions as a protein phosphatase by dephosphorylating protein substrates on serine, threonine, and tyrosine residues. PTEN also functions as a lipid phosphatase by dephosphorylating phophoinosital 3,4,5-triphosphate (PIP3), a key signaling component of the phosphoinositol-3-kinase (PI3-kinase). PTEN is a known tumor suppressor that has been implicated in cellular processes including mediation of the MAP kinase signaling pathway, centromeric maintenance, and is implicated in DNA repair pathways through mediation of Rad51 gene expression. Tumor suppressors play roles in maintaining genome stability, and loss of function of these tumor suppressors is known to result in genomic instability. Genetic instability represents an inevitable consequence of the loss of tumor suppressors. Indeed, the frequent occurrence of PTEN mutation and genetic instability is found in a large range of PTEN-deficient cancers. Likewise, it is known that several tumor cell lines are PTEN deficient. Likewise, it is known that several tumor cell lines are PTEN deficient. PTEN-null embryonic stem cells were shown to exhibit DNA repair checkpoint defects in response to ionizing radiation, which results in the accumulation of unrepaired chromosomes with DNA double-strand gaps and breaks. Further mechanistic study revealed that the observed G2 checkpoint defects may result from functional impairment of the checkpoint protein, CHK1, due to lack of PTEN. PTEN deficiency directly elevates AKT kinase activity, which triggers CHK1 phosphorylation. Phosphorylated CHK1 undergoes ubiquitination, which prevents its entry into the nucleus. Sequestering CHK1 in the cytoplasm impairs its normal function in initiating a DNA repair checkpoint. In addition, CHK1 inactivation in PTEN-deficient cells leads to the accumulation of DNA double-strand breaks. Examination of CHK1 localization in a large panel of primary human breast carcinomas indicates an increased cytoplasmic level of CHK1 in tumor cells with lower expression of PTEN and elevated AKT phosphorylation. Furthermore, aneuploidy was frequently observed in both human breast carcinomas with low expression of PTEN and prostatic intraepithelial neoplasia from Pten.sup.+/− mice. Such in vitro and in vivo observations indicate that PTEN deficiencies are involved in initiation of an oncogenic signaling process by causing dysfunction of important checkpoint proteins. The cytoplasm has been considered as the primary site for PTEN to elicit its tumor-suppressive function, and the ability of PTEN to block the PI3-kinase pathway through its phosphatase activity has been regarded as the key mechanism by which PTEN suppresses carcinogenesis. Although the cellular distribution of PTEN varies in different tissues, endogenous PTEN in neurons, gliomas and cells of the thyroid, pancreas and skin is found mostly in the nuclear compartment. Growing evidence indicate that malignancies may be accompanied by translocation of PTEN from the nucleus to the cytoplasm. Inactivation of PTEN, either by mutations, deletions, or promoter hypermethylation, has been identified in a wide variety of tumors. The therapeutic agent of the present invention a method of treating a cancer associated with a PTEN deficiency such as endometrial carcinoma, glioblastoma (glioblastoma multiforme/anaplastic astrocytoma), prostate cancer, renal cancer, small cell lung carcinoma, meningioma, head and neck cancer, thyroid cancer, bladder cancer, colorectal cancer, breast cancer, melanoma.

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

The pharmaceutical compositions can be administered to a patient or subject by any means known in the art including oral and parenteral routes. The term "patient" or "subject" as used herein are interchangeable and refer to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) Tween™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing the therapeutic agent is chosen by the individual physician in view of the patient to be treated, in general, dosage and administration are adjusted to provide an effective amount of the therapeutic agent nanoparticle to the patient being treated. As used herein, the "effective amount" of a nanoparticle containing a protonatable nitrogen-containing therapeutic agent refers to the amount necessary to elicit the desired biological response. As will be appreciated by those of ordinary skill in this art, the effective amount of a nanoparticle containing the therapeutic agent may vary depending on such factors as the desired biological endpoint, the drug to be delivered, the target tissue, the route of administration, etc. For example, the effective amount of a nanoparticle containing the therapeutic agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an embodiment, compositions disclosed herein may include about 10 ppm of palladium or less, about 8 ppm of palladium or less, or about 6 ppm of palladium or less. For example, provided here is a composition that includes nanoparticles having a polymeric conjugate wherein the composition has less than about 10 ppm of palladium or less.

In an embodiment, compositions disclosed herein may include 10 ppm of palladium or less, 8 ppm of palladium or less, or 6 ppm of palladium or less. For example, provided here is a composition that includes nanoparticles having a polymeric conjugate wherein the composition has less than 10 ppm of palladium or less.

In some embodiments, a composition suitable for freezing is contemplated, including nanoparticles disclosed herein and a solution suitable for freezing, e.g., a sugar such as a mono, di, or poly saccharide, e.g., sucrose and/or a trehalose, and/or a salt and/or a cyclodextrin solution is added to the nanoparticle suspension. The sugar (e.g., sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

In another example, provided herein is a nanoparticle formulation comprising a plurality of disclosed nanoparticles, sucrose, an ionic halide, and water; wherein the nanoparticles/sucrose/water/ionic halide is 3-40%/10-40%/20-95%/0.1-10% (w/w/w/w) or 5-10%/10-15%/80-90%/1-10% (w/w/w/w). For example, such solution may include nanoparticles as disclosed herein, 5% to 20% by weight sucrose and an ionic halide such as sodium chloride, in a concentration of 10-100 mM. In another example, provided herein is a nanoparticle formulation comprising a plurality of disclosed nanoparticles, trehalose, cyclodextrin, and water; wherein the nanoparticles/trehalose/water/cyclodextrin is 3-40%/1-25%/20-95%/1-25% (w/w/w/w) or 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g., about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4% to about 6 wt %, e.g. about 5 wt %) sucrose and about 5 wt % to about 20% (e.g. about 7% wt percent to about 12 wt %, e.g. about 10 wt %) of a cyclodextrin, e.g., HPbCD).

In another example, a contemplated solution may include nanoparticles as disclosed herein, 1% to 25% by weight of a disaccharide such as trehalose or sucrose (e.g., 5% to 25% trehalose or sucrose, e.g. 10% trehalose or sucrose, or 15% trehalose or sucrose, e.g. 5% sucrose) by weight) and a cyclodextrin such as β-cyclodextrin, in a concentration of 1% to 25% by weight (e.g. 5% to 20%, e.g. 10% or 20% by weight, or 15% to 20% by weight cyclodextrin). Contemplated formulations may include a plurality of disclosed nanoparticles (e.g. nanoparticles having PLA-PEG and an active agent), and 2% to 15 wt % (or 4% to 6 wt %, e.g. 5 wt %) sucrose and 5 wt % to 20% (e.g. 7% wt percent to 12 wt %, e.g. 10 wt %) of a cyclodextrin, e.g., HPbCD).

The present disclosure relates in part to lyophilized pharmaceutical compositions that, when reconstituted, have a minimal amount of large aggregates. Such large aggregates may have a size of about 0.5 m or greater, about 1 m or greater, about 10 m or greater, and can be undesirable in a reconstituted solution. Aggregate sizes can be measured using a variety of techniques including those indicated in the U.S. Pharmacopeia ("USP") at <788>, hereby incorporated by reference. The tests outlined in USP <788> include a light obscuration particle count test, microscopic particle count test, laser diffraction, and single particle optical sensing. In one embodiment, the particle size in a given sample is measured using laser diffraction and/or single particle optical sensing.

The USP <788> by light obscuration particle count test sets forth guidelines for sampling particle sizes in a suspension. For solutions with less than or equal to 100 mL, the preparation complies with the test if the average number of particles present does not exceed 6000 per container that are >10 μm and 600 per container that are >25 am.

As outlined in USP <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 jam and 25 jam when viewed at 100× magnification. A linear scale is provided below the graticule. The number of particles with reference to 10 jam and 25 jam are visually tallied. For solutions with less than or equal to 100 mL, the preparation complies with the test if the average number of particles present does not exceed 3000 per container that are >10 jam and 300 per container that are >25 am.

In some embodiments, a 10 mL aqueous sample of a disclosed composition upon reconstitution comprises less than 600 particles per mL having a size greater than or equal to 10 microns; and/or less than 60 particles per mL having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 am. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β, β-trehalose, α, β-trehalose, sophorose, laminaribiose, gentiobiose, turanose, maltulose, palatinose, gentiobiulose, mannobiase, melibiose, melibiulose, rutinose, rutinulose, and xylobiose. Reconstitution shows equivalent DLS size distributions when compared to the starting suspension. However, laser diffraction can detect particles of >10 μm in size in some reconstituted solutions. Further, SPOS also may detect >10 μm sized particles at a concentration above that of the FDA guidelines ($10^4$-$10^5$ particles/mL for >10 μm particles).

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, 1 to 15 weight percent sucrose may be used with an ionic halide salt. In one embodiment, the lyophilized pharmaceutical composition may comprise about 10 to about 100 mM sodium chloride. In one embodiment, the lyophilized pharmaceutical composition may comprise 10 to 100 mM sodium chloride. In another embodiment, the lyophilized pharmaceutical composition may comprise about 100 to about 500 mM of divalent ionic chloride salt, such as calcium chloride or zinc chloride. In another embodiment, the lyophilized pharmaceutical composition may comprise 100 to 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used. In yet another embodiment, the suspension to be lyophilized may further comprise a cyclodextrin, for example, 1 to 25 weight percent of cyclodextrin may be used.

A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active/therapeutic agent, about 4% to about 6% (e.g. about 5% wt percent) sucrose, and about 8 to about 12 weight percent (e.g. about 10 wt percent) HPbCD. In one embodiment, 1 to 25 weight percent trehalose (e.g. 10% to 15%, e.g. 5 to 20% by weight) may be used with cyclodextrin. In one embodiment, the lyophilized pharmaceutical composition may comprise 1 to 25 weight percent β-cyclodextrin. An exemplary composition may comprise nanoparticles comprising PLA-PEG, an active/therapeutic agent, 4% to 6% (e.g. 5% wt percent) sucrose, and 8 to 12 weight percent (e.g. 10 wt percent) HPbCD.

In one aspect, a lyophilized pharmaceutical composition is provided comprising disclosed nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means known to one of ordinary skill in the art, such as described in USP<788>; by light obscuration particle count test, such as described in USP <788>; by microscopic particle count test, laser diffraction, and single particle optical sensing.

In an aspect, a pharmaceutical composition suitable for parenteral use upon reconstitution is provided comprising a plurality of therapeutic particles each comprising a copolymer having a hydrophobic polymer segment and a hydrophilic polymer segment; an active agent; a sugar; and a cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and an ionic halide salt may comprise adding 5 to 15 weight percent sucrose or 5 to 20 weight percent trehalose (e.g., 10 to 20 weight percent trehalose), and 10 to 500 mM ionic halide salt. In an embodiment, 1 to 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

In another embodiment, the step of adding a disaccharide and a cyclodextrin may comprise adding 5 to 15 weight percent sucrose or 5 to 20 weight percent trehalose (e.g., 10 to 20 weight percent trehalose), and 1 to 25 weight percent cyclodextrin. In an embodiment, 10 to 15 weight percent cyclodextrin is added.

In another aspect, a method of preventing substantial aggregation of particles in a pharmaceutical nanoparticle composition is provided comprising adding a sugar and a salt to the lyophilized formulation to prevent aggregation of the nanoparticles upon reconstitution. In an embodiment, a cyclodextrin is also added to the lyophilized formulation. In yet another aspect, a method of preventing substantial aggregation of particles in a pharmaceutical nanoparticle composition is provided comprising adding a sugar and a cyclodextrin to the lyophilized formulation to prevent aggregation of the nanoparticles upon reconstitution.

A contemplated lyophilized composition may have a therapeutic particle concentration of greater than about 40 mg/mL. The formulation suitable for parenteral administration may have less than about 600 particles having a size greater than 10 microns in a 10 mL dose. Lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

A contemplated lyophilized composition may have a therapeutic particle concentration of greater than 40 mg/mL. The formulation suitable for parenteral administration may have less than 600 particles having a size greater than 10 microns in a 10 mL dose. Lyophilizing may comprise freezing the composition at a temperature of greater than −40° C., or e.g. less than −30° C., forming a frozen composition; and drying the frozen composition to form the lyophilized composition. The step of drying may occur at 50 mTorr at a temperature of −25 to −34° C., or −30 to −34° C.

Methods of Treatment

In some embodiments, targeted nanoparticles may be used for the purpose of treatment. As used herein the terms "treat", "treatment", or "treating" mean to alleviate, ameliorate, relieve, delay onset of, inhibit progression of, reduce severity of, and/or reduce incidence of one or more symptoms or features of a disease, disorder, and/or condition. In some embodiments, targeted nanoparticles may be used to treat solid tumors, e.g., cancer and/or cancer cells. In certain embodiments, targeted nanoparticles or pharmaceutical compositions comprising the nanoparticles may be used to treat any cancer wherein prostate-specific membrane antigen (PSMA) is expressed on the surface of cancer cells or in the tumor neovasculature in a subject in need thereof, including the neovasculature of prostate or non-prostate solid tumors. Examples of the PSMA-related indication include, but are not limited to, prostate cancer, breast cancer, non-small cell lung cancer, colorectal carcinoma, and glioblastoma.

In some embodiments, targeted nanoparticles or pharmaceutical compositions comprising the nanoparticles may be used for the preparation of a medicament to alleviate, ameliorate, relieve, delay onset of, inhibit progression of, reduce severity of, and/or reduce incidence of one or more symptoms or features of a disease, disorder, and/or condition. In some embodiments, targeted nanoparticles or pharmaceutical compositions comprising the nanoparticles may be used for the preparation of a medicament to treat any cancer wherein prostate-specific membrane antigen (PSMA) is expressed on the surface of cancer cells or in the tumor neovasculature in a subject in need thereof, including the neovasculature of prostate or non-prostate solid tumors.

The term "cancer" includes pre-malignant as well as malignant cancers. Cancers include, but are not limited to, blood (e.g., chronic myelogenous leukemia, chronic myelomonocytic leukemia, Philadelphia chromosome positive acute lymphoblastic leukemia, mantle cell lymphoma), prostate, gastric cancer, colorectal cancer, skin cancer, e.g., melanomas or basal cell carcinomas, lung cancer (e.g., non-small cell lung cancer), breast cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer (e.g., hepatocellular carcinoma), kidney cancer (e.g., renal cell carcinoma), testicular cancer, biliary tract cancer, small bowel or appendix cancer, gastrointestinal stromal tumor, salivary gland cancer, thyroid gland cancer, adrenal gland cancer, osteosarcoma, chondrosarcoma, cancer of hematological tissues head or neck cancer, and the like. "Cancer cells" can be in the form of a tumor (i.e., a solid tumor), exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect, a method for the treatment of cancer (e.g., leukemia) is provided. In some embodiments, the treatment of cancer comprises administering a therapeutically effective amount of inventive targeted particles to a subject in need thereof, in such amounts and for such time as is necessary to achieve the desired result. In certain embodiments, a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect, a method for administering inventive compositions to a subject suffering from cancer (e.g., leukemia) is provided. In some embodiments, particles may be administered to a subject in such amounts and for such time as is necessary to achieve the desired result (i.e., treatment of cancer). In certain embodiments, a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, disclosed nanoparticles can be used to inhibit the growth of cancer cells, e.g., myelogenous leukemia cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e., not as a disclosed nanoparticle).

In some embodiments, the therapeutic nanoparticle is administered with a compound selected from the group consisting of a topoisomerase I inhibitor, a MEK 1/2 inhibitor, a HSP90 inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, docetaxel, paclitaxel, leucovorin, levamisole, irinotecan, estramustine, etoposide, nitrogen mustards, BCNU, carmustine, lomustine, vinblastine, vincristine, vinorelbine, oxaliplatin, imatinib mesylate, bevacizumab, hexamethylmelamine, topotecan, tyrosine kinase inhibitors, tyrphostins, herbimycin A, genistein, erbstatin, hydroxyzine, glatiramer acetate, interferon beta-1a, interferon beta-1b, natalizumab and lavendustin A; and a pharmaceutically acceptable carrier.

In another aspect, there is provided a therapeutic nanoparticle as described herein for use as a medicament in a subject.

In yet another aspect, there is provided a therapeutic nanoparticle as described herein for use in the production of an anti-proliferative effect in a subject.

In still another aspect, there is provided a therapeutic nanoparticle as described herein for use in a subject as an anti-invasive agent in the containment and/or treatment of solid tumor disease.

In yet another aspect, there is provided the use of a therapeutic nanoparticle as described herein in the prevention or treatment of cancer in a subject.

In still another aspect, there is provided a therapeutic nanoparticle as described herein for use in the prevention or treatment of cancer in a subject.

In yet another aspect, there is provided the use of a therapeutic nanoparticle as described herein in the manufacture of a medicament for the prevention or treatment of cancer in a subject.

In still another aspect, there is provided the use of a therapeutic nanoparticle as described herein for the production of an anti-proliferative effect in a subject.

In yet another aspect, there is provided the use of a therapeutic nanoparticle as described herein in the manufacture of a medicament for use in the production of an anti-proliferative effect in a subject.

In still another aspect, there is provided the use of a therapeutic nanoparticle as described herein in the manufacture of a medicament for use in a subject as an anti-invasive agent in the containment and/or treatment of solid tumor disease.

In yet another aspect, there is provided a method for producing an anti-proliferative effect in a subject in need of such treatment which comprises administering to said subject an effective amount of a therapeutic nanoparticle as described herein.

In still another aspect, there is provided a method for producing an anti-invasive effect by the containment and/or treatment of solid tumor disease in a subject in need of such treatment which comprises administering to said subject an effective amount of a therapeutic nanoparticle as described herein.

In yet another aspect, there is provided a therapeutic nanoparticle as described herein for use in the prevention or treatment of solid tumor disease in a subject.

In still another aspect, there is provided the use of a therapeutic nanoparticle as described herein in the manufacture of a medicament for use in the prevention or treatment of solid tumor disease in a subject.

In yet another aspect, there is provided a method for the prevention or treatment of solid tumor disease in a subject in need of such treatment which comprises administering to said subject an effective amount of a therapeutic nanoparticle as described herein.

U.S. Pat. No. 8,206,747, issued Jun. 26, 2012, entitled "Drug Loaded Polymeric Nanoparticles and Methods of Making and Using Same" is hereby incorporated by reference in its entirety.

EMBODIMENTS

Some embodiments of this invention are as follows:
1. A therapeutic nanoparticle comprising:
   about 0.05 to about 30 weight percent of a substantially hydrophobic acid;
   about 0.2 to about 25 weight percent of a therapeutic agent; wherein the $pK_a$ of the protonated therapeutic agent is at least about 1.0 $pK_a$ units greater than the $pK_a$ of the hydrophobic acid; and
   about 50 to about 99.75 weight percent of a polymer selected from diblock poly(lactic) acid-poly(ethylene)glycol copolymer or a diblock poly(lactic acid-co-glycolic acid)-poly(ethylene)glycol copolymer and combination, wherein the therapeutic nanoparticle comprises about 10 to about 30 weight percent poly(ethylene)glycol, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.
2. The therapeutic nanoparticle of embodiment 1 wherein the amount of the therapeutic agent is about 0.2 to about 20 weight percent.
3. The therapeutic nanoparticle according to embodiment 1 or 2 comprising:
   1-(4-{[4-(dimethylamino)piperidin-1-yl]carbonyl}phenyl)-3-[4-(4,6-dimorpholin-4-yl-1,3,5-triazin-2-yl)phenyl]urea;
   and PLA-PEG (in a 16:5 molar ratio) in a weight ratio of about 1:7 1-(4-{[4-(dimethylamino)piperidin-1-yl]carbonyl}phenyl)-3-[4-(4,6-dimorpholin-4-yl-1,3,5-triazin-2-yl)phenyl]urea:PLA-PEG.
4. The therapeutic nanoparticle according to embodiment 1 or 2 comprising:
   1-(4-{[4-(dimethylamino)piperidin-1-yl]carbonyl}phenyl)-3-[4-(4,6-dimorpholin-4-yl-1,3,5-triazin-2-yl)phenyl]urea;
   and PLA-PEG (in a 16:5 molar ratio) in a weight ratio of about 1:14 1-(4-{[4-(dimethylamino)piperidin-1-yl]carbonyl}phenyl)-3-[4-(4,6-dimorpholin-4-yl-1,3,5-triazin-2-yl)phenyl]urea:PLA-PEG.
5. The therapeutic nanoparticle according to embodiment 1 or 2 comprising:
   1-(4-{[4-(dimethylamino)piperidin-1-yl]carbonyl}phenyl)-3-[4-(4,6-dimorpholin-4-yl-1,3,5-triazin-2-yl)phenyl]urea;
   and PLA-PEG (in a 16:5 molar ratio) in a weight ratio of about 1:5 1-(4-{[4-(dimethylamino)piperidin-1-yl]carbonyl}phenyl)-3-[4-(4,6-dimorpholin-4-yl-1,3,5-triazin-2-yl)phenyl]urea:PLA-PEG.
6. A therapeutic nanoparticle comprising:
   about 0.2 to about 25 weight percent of a therapeutic agent;
   a substantially hydrophobic acid, wherein the molar ratio of the substantially hydrophobic acid to the therapeutic agent ranges from about 0.25:1 to about 2:1 and wherein the pKa of the protonated therapeutic agent is at least about 1.0 $pK_a$ units greater than the $pK_a$ of the hydrophobic acid; and
   about 50 to about 99.75 weight percent of a polymer selected from diblock poly(lactic) acid-poly(ethylene)glycol copolymer or a diblock poly(lactic acid-co-glycolic acid)-poly(ethylene)glycol copolymer and combination, wherein the therapeutic nanoparticle comprises about 10 to about 30 weight percent poly(ethylene)glycol, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.
7. The therapeutic nanoparticle of embodiment 6, wherein the amount of the therapeutic agent is about 0.2 to about 20 weight percent.
8. A therapeutic nanoparticle comprising:
   a substantially hydrophobic acid;
   a therapeutic agent; wherein the $pK_a$ of the protonated therapeutic agent is at least about 1.0 $pK_a$ units greater than the $pK_a$ of the hydrophobic acid; and
   a polymer selected from diblock poly(lactic) acid-poly(ethylene)glycol copolymer or a diblock poly(lactic acid-co-glycolic acid)-poly(ethylene)glycol copolymer and combination thereof, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.
9. A therapeutic nanoparticle comprising:
   a therapeutic agent;
   a substantially hydrophobic acid, wherein the molar ratio of the substantially hydrophobic acid to the therapeutic agent ranges from about 0.25:1 to about 2:1 and wherein the pKa of the protonated therapeutic agent is at least about 1.0 $pK_a$ units greater than the $pK_a$ of the hydrophobic acid; and
   a polymer selected from diblock poly(lactic) acid-poly(ethylene)glycol copolymer or a diblock poly(lactic acid-co-glycolic acid)-poly(ethylene)glycol copolymer and combination thereof, and, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.
10. The therapeutic nanoparticle of embodiment 6 or 9, wherein the molar ratio of the substantially hydrophobic acid to the therapeutic agent is about 0.5:1 to about 1.5:1.
11. The therapeutic nanoparticle of embodiment 6 or 9, wherein the molar ratio of the substantially hydrophobic acid to the therapeutic agent is about 0.25:1 to about 1:1.
12. The therapeutic nanoparticle of embodiment 6 or 9, wherein the molar ratio of the substantially hydrophobic acid to the therapeutic agent is about 0.75:1 to about 1.25:1.
13. The therapeutic nanoparticle of any one of embodiments 1-12, wherein the $pK_a$ of the protonated therapeutic agent is at least about 2.0 $pK_a$ units greater than the $pK_a$ of the hydrophobic acid.
14. The therapeutic nanoparticle of any one of embodiments 1-12, wherein the $pK_a$ of the protonated therapeutic agent is at least about 4.0 $pK_a$ units greater than the $pK_a$ of the hydrophobic acid.
15. A therapeutic nanoparticle comprising:
   a hydrophobic ion-pair comprising a hydrophobic acid and therapeutic agent; wherein the difference between the pKa of the protonated therapeutic agent and the hydrophobic acid is at least about 1.0 pKa units or greater; and
   about 50 to about 99.75 weight percent of a diblock poly(lactic) acid-poly(ethylene)glycol copolymer, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol, wherein the therapeutic agent is 1-(4-{[4-(dimethylamino) piperidin-1-yl]carbonyl}phenyl)-3-[4-(4,6-dimorpholin-4-yl-1,3,5-triazin-2-yl)phenyl]urea or a pharmaceutically acceptable salt thereof.

16. The therapeutic nanoparticle of embodiment 15, wherein the difference between the pKa of the protonated therapeutic agent and the hydrophobic acid is at least about 2.0 pKa units.

17. The therapeutic nanoparticle of embodiment 15, wherein the difference between the pKa of the protonated therapeutic agent and the hydrophobic acid is at least about 4.0 pKa units.

18. The therapeutic nanoparticle of any one of embodiments 1-5, 8 or 13-17, comprising about 0.05 to about 20 weight percent of the hydrophobic acid.

19. The therapeutic nanoparticle of any one of embodiments 1-18, wherein the substantially hydrophobic acid has a log P ranging from about 2 to about 7.

20. The therapeutic nanoparticle of any one of embodiments 1-18, wherein the substantially hydrophobic acid has a log P ranging from about 4 to about 8.

21. The therapeutic nanoparticle of any one of embodiments 1-20, wherein the substantially hydrophobic acid has a $pK_a$ in water from about −1.0 to about 5.0.

22. The therapeutic nanoparticle of any one of embodiments 1-20, wherein the substantially hydrophobic acid has a $pK_a$ in water from about 2.0 to about 5.0.

23. The therapeutic nanoparticle of any one of embodiments 1-22, wherein the substantially hydrophobic acid and the therapeutic agent form a hydrophobic ion pair in the therapeutic nanoparticle.

24. The therapeutic nanoparticle of any one of embodiments 1-23, wherein the hydrophobic acid is a fatty acid.

25. The therapeutic nanoparticle of embodiment 24, wherein the fatty acid is a saturated fatty acid selected from the group consisting of: caproic acid, enanthic acid, caprylic acid, pelargonic acid, capric acid, undecanoic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, and combinations thereof.

26. The therapeutic nanoparticle of embodiment 24, wherein the fatty acid is an omega-3 fatty acid selected from the group consisting of: hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, and combinations thereof.

27. The therapeutic nanoparticle of embodiment 24, wherein the fatty acid is an omega-6 fatty acid selected from the group consisting of: linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, and combinations thereof.

28. The therapeutic nanoparticle of embodiment 24, wherein the fatty acid is an omega-9 fatty acid selected from the group consisting of: oleic acid, eicosenoic acid, mead acid, erucic acid, nervonic acid, and combinations thereof.

29. The therapeutic nanoparticle of embodiment 28, wherein the fatty acid is oleic acid.

30. The therapeutic nanoparticle of embodiment 29 wherein the weight ratio of 1-(4-{[4-(dimethylamino)piperidin-1-yl]carbonyl}phenyl)-3-[4-(4,6-dimorpholin-4-yl-1,3,5-triazin-2-yl)phenyl]urea to oleic acid is about 6:1.

31. The therapeutic nanoparticle of embodiment 24, wherein the fatty acid is a polyunsaturated fatty acid selected from the group consisting of: rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, and combinations thereof.

32. The therapeutic nanoparticle of any one of embodiments 1-24, wherein the hydrophobic acid is a bile acid.

33. The therapeutic nanoparticle of embodiment 32, wherein the bile acid is selected from the group consisting of chenodeoxycholic acid, ursodeoxycholic acid, deoxycholic acid, hycholic acid, beta-muricholic acid, cholic acid, lithocholic acid, an amino acid-conjugated bile acid, and combinations thereof.

34. The therapeutic nanoparticle of embodiment 33, wherein the bile acid is cholic acid.

35. The therapeutic nanoparticle of embodiment 33, wherein the amino acid-conjugated bile acid is a glycine-conjugated bile acid or a taurine-conjugated bile acid.

36. The therapeutic nanoparticle of any one of embodiments 1-23, wherein the hydrophobic acid is selected from the group consisting of dioctyl sulfosuccinic acid, 1-hydroxy-2-naphthoic acid, dodecylsulfuric acid, naphthalene-1,5-disulfonic acid, naphthalene-2-sulfonic acid, pamoic acid, undecanoic acid, and combinations thereof.

37. The therapeutic nanoparticle of embodiment 36, wherein the hydrophobic acid is pamoic acid.

38. The therapeutic nanoparticle of embodiment 37 wherein the weight ratio of 1-(4-{[4-(dimethylamino)piperidin-1-yl]carbonyl}phenyl)-3-[4-(4,6-dimorpholin-4-yl-1,3,5-triazin-2-yl)phenyl]urea to pamoic acid is about 1.8:1.

39. The therapeutic nanoparticle of any one of embodiments 1-38, comprising about 1 to about 20 weight percent of the therapeutic agent.

40. The therapeutic nanoparticle of any one of embodiments 1-38, comprising about 2 to about 20 weight percent of the therapeutic agent.

41. The therapeutic nanoparticle of any one of embodiments 1-38, comprising about 4 to about 20 weight percent of the therapeutic agent.

42. The therapeutic nanoparticle of any one of embodiments 1-38, comprising about 5 to about 20 weight percent of the therapeutic agent.

43. The therapeutic nanoparticle of any one of embodiments 1-38, wherein the hydrophobic acid has a molecular weight of between about 200 Da and about 800 Da.

44. The therapeutic nanoparticle of any one of embodiments 1-43, wherein the therapeutic nanoparticle substantially retains the therapeutic agent for at least 1 minute when placed in a phosphate buffer solution at 37° C.

45. The therapeutic nanoparticle of any one of embodiments 1-43, wherein the therapeutic nanoparticle substantially immediately releases less than about 30% of the therapeutic agent when placed in a phosphate buffer solution at 37° C.

46. The therapeutic nanoparticle of any one of embodiments 1-43, wherein the therapeutic nanoparticle releases about 10 to about 45% of the therapeutic agent over about 1 hour when placed in a phosphate buffer solution at 37° C.
47. The therapeutic nanoparticle of any one of embodiments 1-43, wherein the therapeutic nanoparticle releases about 0.01 to about 15% of the therapeutic agent over about 4 hours when placed in a phosphate buffer solution at 37° C.
48. The therapeutic nanoparticle of any one of embodiments 1-43, wherein the therapeutic nanoparticle releases about 0.01 to about 15% of the therapeutic agent over about 10 hours when placed in a phosphate buffer solution at 37° C.
49. The therapeutic nanoparticle of any one of embodiments 1-43, wherein the therapeutic nanoparticle releases about 0.01 to about 25% of the therapeutic agent over about 20 hours when placed in a phosphate buffer solution at 37° C.
50. The therapeutic nanoparticle of any one of embodiments 1-43, wherein the therapeutic nanoparticle releases about 1 to about 40% of the therapeutic agent over about 40 hours when placed in a phosphate buffer solution at 37° C.
51. The therapeutic nanoparticle of any one of embodiments 1-43, wherein the therapeutic nanoparticle has a release profile that is substantially the same as a release profile for a control nanoparticle that is substantially the same as the therapeutic nanoparticle except that it does not contain a fatty acid or bile acid.
52. The therapeutic nanoparticle of any one of embodiments 1-51, wherein the poly(lactic) acid-poly(ethylene)glycol copolymer has a poly(lactic) acid number average molecular weight fraction of about 0.6 to about 0.95.
53. The therapeutic nanoparticle of any one of embodiments 1-51, wherein the poly(lactic) acid-poly(ethylene)glycol copolymer has a poly(lactic) acid number average molecular weight fraction of about 0.6 to about 0.8.
54. The therapeutic nanoparticle of any one of embodiments 1-51, wherein the poly(lactic) acid-poly(ethylene)glycol copolymer has a poly(lactic) acid number average molecular weight fraction of about 0.75 to about 0.85.
55. The therapeutic nanoparticle of any one of embodiments 1-51, wherein the poly(lactic) acid-poly(ethylene)glycol copolymer has a poly(lactic) acid number average molecular weight fraction of about 0.7 to about 0.9.
56. The therapeutic nanoparticle of any one of embodiments 1-55, wherein the therapeutic nanoparticle comprises about 10 to about 25 weight percent poly(ethylene)glycol.
57. The therapeutic nanoparticle of any one of embodiments 1-55, wherein the therapeutic nanoparticle comprises about 10 to about 20 weight percent poly(ethylene)glycol.
58. The therapeutic nanoparticle of any one of embodiments 1-55, wherein the therapeutic nanoparticle comprises about 15 to about 25 weight percent poly(ethylene)glycol.
59. The therapeutic nanoparticle of any one of embodiments 1-55, wherein the therapeutic nanoparticle comprises about 20 to about 30 weight percent poly(ethylene)glycol.
60. The therapeutic nanoparticle of any one of embodiments 1-59, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.
61. The therapeutic nanoparticle of any one of embodiments 1-60, further comprising about 0.2 to about 30 weight percent poly(lactic) acid-poly(ethylene)glycol copolymer functionalized with a targeting ligand.
62. The therapeutic nanoparticle of any one of embodiments 1-60, further comprising about 0.2 to about 30 weight percent poly(lactic) acid-co-poly(glycolic) acid-poly(ethylene)glycol copolymer functionalized with a targeting ligand.
63. The therapeutic nanoparticle of embodiment 61 or 62, wherein the targeting ligand is covalently bound to the poly(ethylene)glycol.
64. The therapeutic nanoparticle of any one of embodiments 1-63, wherein the hydrophobic acid is a polyelectrolyte.
65. The therapeutic nanoparticle of embodiment 64, wherein the polyelectrolyte is selected from the group consisting of a poly(styrene sulfonic acid), polypolyacrylic acid, and polymethacrylic acid.
66. The therapeutic nanoparticle of any one of embodiments 1-65, wherein the substantially hydrophobic acid is a mixture of two or more substantially hydrophobic acids.
67. The therapeutic nanoparticle of embodiment 66, comprising a mixture of two substantially hydrophobic acids.
68. The therapeutic nanoparticle of embodiment 67, wherein the two substantially hydrophobic acids are oleic acid and cholic acid.
69. The therapeutic nanoparticle of embodiment 66, comprising a mixture of three substantially hydrophobic acids.
70. The therapeutic nanoparticle of embodiment 66, comprising a mixture of four substantially hydrophobic acids.
71. The therapeutic nanoparticle of embodiment 66, comprising a mixture of five substantially hydrophobic acids.
72. A therapeutic nanoparticle prepared by a process comprising the steps of:
emulsification of a first organic phase comprising a first polymer, a therapeutic agent, and a substantially hydrophobic acid, thereby forming an emulsion phase;
quenching of the emulsion phase thereby forming a quenched phase; and
filtration of the quenched phase to recover the therapeutic nanoparticles, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.
73. The therapeutic nanoparticle of embodiment 72, wherein the hydrophobic acid is a fatty acid.
74. The therapeutic nanoparticle of embodiment 73, wherein the fatty acid is a saturated fatty acid selected from the group consisting of: caproic acid, enanthic acid, caprylic acid, pelargonic acid, capric acid, undecanoic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, and combinations thereof.
75. The therapeutic nanoparticle of embodiment 73, wherein the fatty acid is an omega-3 fatty acid selected from the group consisting of: hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, and combinations thereof.
76. The therapeutic nanoparticle of embodiment 73, wherein the fatty acid is an omega-6 fatty acid selected from the group consisting of: linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, and combinations thereof.
77. The therapeutic nanoparticle of embodiment 73, wherein the fatty acid is an omega-9 fatty acid selected from the group consisting of: oleic acid, eicosenoic acid, mead acid, erucic acid, nervonic acid, and combinations thereof.
78. The therapeutic nanoparticle of embodiment 77, wherein the fatty acid is oleic acid.
79. The therapeutic nanoparticle of embodiment 73, wherein the fatty acid is a polyunsaturated fatty acid selected from the group consisting of: rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, and combinations thereof.
80. The therapeutic nanoparticle of any one of embodiments 72, wherein the hydrophobic acid is a bile acid.
81. The therapeutic nanoparticle of embodiment 80, wherein the bile acid is selected from the group consisting of chenodeoxycholic acid, ursodeoxycholic acid, deoxycholic acid, hycholic acid, beta-muricholic acid, cholic acid, lithocholic acid, an amino acid-conjugated bile acid, and combinations thereof.
82. The therapeutic nanoparticle of embodiment 81, wherein the bile acid is cholic acid.
83. The therapeutic nanoparticle of embodiment 81, wherein the amino acid-conjugated bile acid is a glycine-conjugated bile acid or a taurine-conjugated bile acid.
84. The therapeutic nanoparticle of any one of embodiments 72, wherein the hydrophobic acid is selected from the group consisting of dioctyl sulfosuccinic acid, 1-hydroxy-2-naphthoic acid, dodecylsulfuric acid, naphthalene-1,5-disulfonic acid, naphthalene-2-sulfonic acid, pamoic acid, undecanoic acid, and combinations thereof.
85. The therapeutic nanoparticle of embodiment 84, wherein the hydrophobic acid is pamoic acid.
86. The therapeutic nanoparticle of any one of embodiments 72-85, wherein the hydrophobic acid has a molecular weight of between about 200 Da and about 800 Da.
87. The therapeutic nanoparticle of any one of embodiments 72-86, wherein the therapeutic nanoparticle substantially retains the therapeutic agent for at least 1 minute when placed in a phosphate buffer solution at 37° C.
88. The therapeutic nanoparticle of any one of embodiments 72-86, wherein the therapeutic nanoparticle substantially immediately releases less than about 30% of the therapeutic agent when placed in a phosphate buffer solution at 37° C.
89. The therapeutic nanoparticle of any one of embodiments 72-86, wherein the therapeutic nanoparticle releases about 10 to about 45% of the therapeutic agent over about 1 hour when placed in a phosphate buffer solution at 37° C.
90. The therapeutic nanoparticle of any one of embodiments 72-86, wherein the therapeutic nanoparticle releases about 0.01 to about 15% of the therapeutic agent over about 4 hours when placed in a phosphate buffer solution at 37° C.
91. The therapeutic nanoparticle of any one of embodiments 72-86, wherein the therapeutic nanoparticle releases about 0.01 to about 15% of the therapeutic agent over about 10 hours when placed in a phosphate buffer solution at 37° C.
92. The therapeutic nanoparticle of any one of embodiments 72-86, wherein the therapeutic nanoparticle releases about 0.01 to about 25% of the therapeutic agent over about 20 hours when placed in a phosphate buffer solution at 37° C.
93. The therapeutic nanoparticle of any one of embodiments 72-86, wherein the therapeutic nanoparticle releases about 1 to about 40% of the therapeutic agent over about 40 hours when placed in a phosphate buffer solution at 37° C.
94. The therapeutic nanoparticle of any one of embodiments 72-86, wherein the therapeutic nanoparticle has a release profile that is substantially the same as a release profile for a control nanoparticle that is substantially the same as the therapeutic nanoparticle except that it does not contain a fatty acid or bile acid.
95. The therapeutic nanoparticle of any one of embodiments 72-94, wherein the first polymer is poly(lactic) acid-poly(ethylene)glycol copolymer.
96. The therapeutic nanoparticle of any one of embodiments 72-94, wherein the first polymer is poly(lactic) acid-co-poly(glycolic) acid-poly(ethylene)glycol copolymer.
97. The therapeutic nanoparticle of any one of embodiments 72-96, wherein the substantially hydrophobic acid is a mixture of two or more substantially hydrophobic acids.
98. The therapeutic nanoparticle of embodiment 97, comprising a mixture of two substantially hydrophobic acids.
99. The therapeutic nanoparticle of embodiment 97, comprising a mixture of three substantially hydrophobic acids.
100. The therapeutic nanoparticle of embodiment 97, comprising a mixture of four substantially hydrophobic acids.
101. The therapeutic nanoparticle of embodiment 97, comprising a mixture of five substantially hydrophobic acids.
102. The therapeutic nanoparticle of any of embodiments 1, 5-95, or 97-101 wherein the polymer is PLA-PEG and the mole ratio of PLA-PEG is 5:1.
103. A therapeutic nanoparticle prepared by the process comprising the steps of:
combining a first organic phase with a first aqueous solution to form a second phase;
emulsifying the second phase to form an emulsion phase, wherein the emulsion phase comprises a first polymer, therapeutic agent, and a substantially hydrophobic acid;
quenching of the emulsion phase thereby forming a quenched phase; and
filtering the quenched phase to recover the therapeutic nanoparticles, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea, the first organic phase comprises the therapeutic agent and pamoic acid in a weight ratio of therapeutic agent to pamoic acid of about 11:1 and PLA-PEG (in a 16:5 molar ratio) in a weight ratio of therapeutic agent to PLA-PEG of about 1:3 in an organic solvent comprising of benzyl alcohol and ethyl acetate in a weight ratio of benzyl alcohol to ethyl acetate of about 1.25 and the first aqueous solution comprises a polyoxyethylene (100) stearyl ether dissolved in benzyl alcohol in a weight ratio of 0.005:1 and combining the first organic phase and the first aqueous phase in a weight ratio of about 1:5 to form a second phase and emulsifying the second phase formed therefrom and quenching the emulsion phase with 0.1 M citric acid in water solution at pH 4.5 and concentrating the resulting product.
104. A therapeutic nanoparticle of 1-(4-{[4-(dimethylamino)piperidin-1-yl]carbonyl}phenyl)-3-[4-(4,6-dimorpholin-4-yl-1,3,5-triazin-2-yl)phenyl]urea or pharmaceutically acceptable salt thereof.
105. A therapeutic nanoparticle comprising of a therapeutic agent or a pharmaceutically acceptable salt thereof and a polymer selected from diblock poly(lactic) acid-poly(ethylene)glycol copolymer or a diblock poly(lactic acid-co-glycolic acid)-poly(ethylene)glycol copolymer and combination thereof, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.

106. The therapeutic nanoparticle of any of embodiments 1-71, 104, or 105, wherein a targeting ligand is additionally present and is PLA-PEG-GL, wherein GL has the following structure:

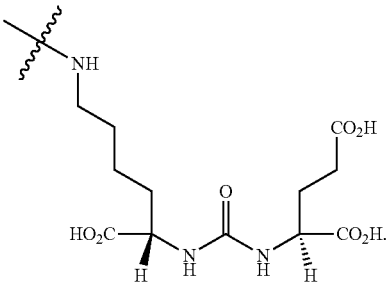 [SMILES: *NCCCC[C@H](NC(=O)N[C@@H](CCC(=O)O)C(=O)O)C(=O)O]

107. The therapeutic nanoparticle according to any one of embodiments 1-71 or 104-106, further comprising a solubilizer.
108. The therapeutic nanoparticle according to embodiment 107, wherein the solubilizer is polysorbate 80.
109. The therapeutic nanoparticle of embodiment 107, wherein the solubilizer is polyoxyethylene (100) stearyl ether.
110. The therapeutic nanoparticle of any one of embodiments 1-109, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea.
111. A pharmaceutical composition comprising a therapeutic nanoparticle of any of embodiments 1-110 and a pharmaceutically acceptable excipient.
112. The pharmaceutical composition of embodiment 111 comprising a plurality of therapeutic nanoparticles.
113. The pharmaceutical composition of embodiment 111 or 112, further comprising a saccharide.
114. The pharmaceutical composition of any one of embodiments 111-113, further comprising a cyclodextrin.
115. The pharmaceutical composition of embodiments 113 or 114, wherein the saccharide is a disaccharide selected from the group consisting of sucrose, trehalose, and a mixture thereof.
116. A method of treating cancer in a subject in need thereof, comprising administering to the subject a therapeutically effective amount of a therapeutic nanoparticle of any one of embodiments 1-110 or a pharmaceutical composition of any one of embodiments 111-115.
117. The method of embodiment 116, wherein the cancer is chronic myelogenous leukemia.
118. The method of embodiment 116, wherein the cancer is gastrointestinal stromal tumor.
119. The method of embodiment 116, wherein the cancer is selected from the group consisting of chronic myelomonocytic leukemia, hypereosinophilic syndrome, renal cell carcinoma, hepatocellular carcinoma, Philadelphia chromosome positive acute lymphoblastic leukemia, non-small cell lung cancer, pancreatic cancer, breast cancer, a solid tumor, head and neck cancer and mantle cell lymphoma.
120. The method of embodiment 119, wherein the cancer is breast cancer.
121. A process for preparing a therapeutic nanoparticle, comprising the steps of:
combining a first organic phase with a first aqueous solution to form a second phase;
emulsifying the second phase to form an emulsion phase, wherein the emulsion phase comprises a first polymer, therapeutic agent, and a substantially hydrophobic acid;
quenching of the emulsion phase thereby forming a quenched phase; and
filtering the quenched phase to recover the therapeutic nanoparticles, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea or a pharmaceutically acceptable salt thereof.
122. The process of embodiment 121, further comprising combining the therapeutic agent and the substantially hydrophobic acid in the second phase prior to emulsifying the second phase.
123. The process of embodiment 122, wherein the therapeutic agent and the substantially hydrophobic acid form a hydrophobic ion pair prior to emulsifying the second phase.
124. The process of embodiment 122, wherein the therapeutic agent and the substantially hydrophobic acid form a hydrophobic ion pair prior during emulsification of the second phase.
125. The process of embodiment 121, further comprising combining the therapeutic agent and the substantially hydrophobic acid in the second phase substantially concurrently with emulsifying the second phase.
126. The process of embodiment 125, wherein the first organic phase comprises the therapeutic agent and the first aqueous solution comprises the substantially hydrophobic acid.
127. The process of any one of embodiments 121-126, wherein the therapeutic agent, when protonated, has a first $pK_a$, the substantially hydrophobic acid has a second $pK_a$, and the emulsion phase is quenched with an aqueous solution having a pH equal to a $pK_a$ unit between the first $pK_a$ and the second $pK_a$.
128. The process of embodiment 127, wherein the quenched phase has a pH equal to a $pK_a$ unit between the first $pK_a$ and the second $pK_a$.
129. The process of any one of embodiments 121-128, wherein the therapeutic agent, when protonated, has a first $pK_a$, the substantially hydrophobic acid has a second $pK_a$, and the first aqueous solution has a pH equal to a $pK_a$ unit between the first $pK_a$ and the second $pK_a$.
130. The process of any one of embodiments 127-129, wherein the pH is equal to a $pK_a$ unit that is about equidistant between the first $pK_a$ and the second $pK_a$.
131. The process of any one of embodiments 121-130, wherein the therapeutic agent is 1-(4-{[4-(dimethylamino)piperidin-1-yl]carbonyl}phenyl)-3-[4-(4,6-dimorpholin-4-yl-1,3,5-triazin-2-yl)phenyl]urea.

EXAMPLES

The invention now being generally described, it will be more readily understood by reference to the following examples which are included merely for purposes of illustration of certain aspects and embodiments, and are not intended to limit the invention in any way.

Example 1

Preparation of Formulation a with Therapeutic Agent (a) Preparation of organic phase stock: Benzyl alcohol (8932.5 mg) was dissolved in 67.5 mg of RODI (reverse osmosis deionized) water with mixing. The therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea, (150 mg) was added to the solution, and then it was sonicated until the drug dissolved. PLA-PEG-GL (19.2 mg) and PLA-PEG in a ratio of 16 mol/5 mol (830.8 mg) was added thereto and vortexed until dissolved.

(b) Preparation of aqueous phase stock: Sodium Cholate (2.75 g) was dissolved in RODI water (955.5 g) on a stir plate. Benzyl alcohol (40 g) was added to the sodium cholate/water solution and the mixture was stirred on a stir plate until dissolved.

(c) Formation of emulsion: The weight ratio of aqueous phase to organic phase was 5:1. The organic phase, which weighed 10 g, was poured into 50 g of the aqueous phase that was cooled in ice water bath, and the mixture homogenized using a hand homogenizer for 15 seconds. The coarse emulsion was fed through a high pressure homogenizer with pressure set at 10485 psi on gauge for 1 pass to form a nanoemulsion (fine emulsion).

(d) Formation of nanoparticles: The nanoemulsion was poured into 600 g of cold RODI water (less than 2° C.) while stirring on a stir plate to form a quenched phase. (The weight ratio of quench to emulsion is 10:1). To the quenched phase was added 64.3 grams of a solution of polysorbate 80 (350 grams dissolved in 650 g RODI water) with mixing.

(e) Concentration of nanoparticles through tangential flow filtration (TFF): The quenched phase was concentrated using TFF with 300 kDa Pall cassette (2 membranes) to form a nanoparticle concentrate of approximately 200 mL. The nanoparticle concentrate was diafiltered with approximately 20 diavolumes of cold RODI water at less than 2° C. The volume of the diafiltered nanoparticle concentrate was reduced to minimal volume.

Thus, this formulation contained 1-(4-{[4-(dimethylamino)piperidin-1-yl]carbonyl}phenyl)-3-[4-(4,6-dimorpholin-4-yl-1,3,5-triazin-2-yl)phenyl]urea, and the polymers PLA-PEG (in a 16:5 molar ratio) and PLA-PEG-GL in a weight ratio of PLA-PEG to PLA-PEG-GL of about 43:1 and a weight ratio of the therapeutic agent, 1-(4-{[4-(dimethylamino)piperidin-1-yl]carbonyl}phenyl)-3-[4-(4,6-dimorpholin-4-yl-1,3, 5-triazin-2-yl)phenyl]urea, to polymers of 15:85. No counterion or hydrophobic acid was present in this formulation. The particle size of a nanoparticle so formed as described herein above was about 116 nm.

Example 2

Preparation of Formulation B with Therapeutic Agent (a) Preparation of organic phase stock: Oleic acid (900 mg), trifluoroacetic acid (TFA) (273 mg) was dissolved in benzyl alcohol (8827 mg). The therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea (120 mg) was mixed with the oleic acid/TFA/benzyl alcohol solution and heated to 80° C. for 10 minutes to dissolve the therapeutic agent therein. Once the 1-(4-{[4-(dimethylamino)piperidin-1-yl]carbonyl}phenyl)-3-[4-(4,6-dimorpholin-4-yl-1,3, 5-triazin-2-yl)phenyl]urea was dissolved, the solution was allowed to cool to room temperature. This solution was thoroughly mixed with a polymer solution of PLA-PEG in a ratio of 16 moles/5 moles (860 mg), PLA-PEG-GL (18.9 mg) and ethyl acetate (4549 mg) to form a solution.

(b) Preparation of aqueous phase stock: Sodium Cholate (4.5 g) was dissolved in RODI water (955.5 g) on a stir plate. Benzyl alcohol (40 g) was added to the sodium cholate/water solution and the mixture was stirred on a stir plate until dissolved.

(c) Formation of emulsion: The weight ratio of aqueous phase to organic phase was 5:1. The organic phase was poured into 33.4 g of the aqueous phase that was cooled in ice water bath, and the mixture homogenized using a hand homogenizer for 15 seconds. The coarse emulsion was fed through a high pressure homogenizer with pressure set at 10485 psi on gauge for 1 pass to form a nanoemulsion (fine emulsion).

(d) Formation of nanoparticles: The nanoemulsion was poured into 401.2 g of cold RODI water (less than 2° C.) while stirring on a stir plate to form a quenched phase. To the quenched phase was added 51.4 grams of a solution of polysorbate 80 (350 g dissolved in 650 g RODI water) with mixing.

(e) Concentration of nanoparticles through tangential flow filtration (TFF): The quenched phase was concentrated using TFF with 300 kDa Pall cassette (2 membranes) to form a nanoparticle concentrate of approximately 200 mL. The nanoparticle concentrate was diafiltered with approximately 20 diavolumes of cold RODI water at less than 2° C. The volume of the diafiltered nanoparticle concentrate was reduced to minimal volume.

Thus, this formulation contained 1-(4-{[4-(dimethylamino)piperidin-1-yl]carbonyl}phenyl)-3-[4-(4,6-dimorpholin-4-yl-1,3,5-triazin-2-yl)phenyl]urea and the polymers PLA-PEG (in a 16:5 molar ratio) and PLA-PEG-GL in a weight ratio of PLA-PEG to PLA-PEG-GL of about 46:1 and a weight ratio of the therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea, to polymers of 12:88. It contained about 5.7% by weight 1-(4-{[4-(dimethylamino)piperidin-1-yl]carbonyl}phenyl)-3-[4-(4,6-dimorpholin-4-yl-1,3,5-triazin-2-yl)phenyl]urea and about 9% by weight oleic acid in a 3% trifluoroacetic acid. The particle size of a nanoparticle so formed as described herein above was about 74 nm.

Example 3

Preparation of Formulation C with Therapeutic Agent (a) Preparation of organic phase stock: Trifluoroacetic acid (1600 mg), benzyl alcohol (8827 mg), and RODI water (1500 mg) were mixed together and, if necessary, heated to form a solution. To this solution was added the therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea (1468.8 mg), and the resulting mixture was sonicated to form a solution. Once the therapeutic agent was dissolved, the solution was allowed to cool to room temperature. This solution was added to a solution of pamoic acid (136.5 mg) and DMSO (331.2 mg). This solution was thoroughly mixed with a polymer solution of PLA-PEG in a ratio of 16 mol/5 mol (643.5 mg), PLA-PEG-GL (14.5 mg) and ethyl acetate (7200 mg).

(b) Preparation of aqueous phase stock: A surfactant, Brij S 100 (polyoxyethylene (100) stearyl ether) (200 mg), was dissolved in benzyl alcohol (40.0 g) with stirring, and cold RODI water (959.8 g) was added thereto and mixed on ice until the solution clears. The aqueous phase stock was cooled to less than 2° C. with stirring.

(c) Formation of emulsion: The weight ratio of aqueous phase to organic phase was 5:1. The organic phase was poured into 50.07 g of the aqueous phase that was cooled in ice water bath, and the mixture homogenized using a hand homogenizer for 15 seconds. The coarse emulsion was fed through a high pressure homogenizer with pressure set at 10485 psi on gauge for 1 pass to form a nanoemulsion (fine emulsion).

(d) Formation of nanoparticles: The nanoemulsion was poured into a quench solution of cold RODI water (1000 g) that was chilled to less than 2° C. and was stirred on a stir plate. To the quenched solution was added to a chilled solution (less than 2° C.) of polysorbate 80 (350 g) dissolved in RODI water (650 g) with mixing.

(e) Concentration of nanoparticles through tangential flow filtration (TFF): The quenched phase was concentrated using TFF with 300 kDa Pall cassette (2 membranes) to form a nanoparticle concentrate of approximately 200 mL. The nanoparticle concentrate was diafiltered with approximately 20 diavolumes of cold RODI water at less than 2° C. The volume of the diafiltered nanoparticle concentrate was reduced to minimal volume.

Thus, this formulation contained 1-(4-{[4-(dimethylamino)piperidin-1-yl]carbonyl}phenyl)-3-[4-(4,6-dimorpholin-4-yl-1,3,5-triazin-2-yl)phenyl]urea, and the polymers PLA-PEG (in a 16:5 molar ratio) and PLA-PEG-GL in a weight ratio of PLA-PEG to PLA-PEG-GL of about 44:1 and a weight ratio of the therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea, to polymers of 22:64. It contained about 60% by weight of pamoic acid to 1-(4-{[4-(dimethylamino)piperidin-1-yl]carbonyl}phenyl)-3-[4-(4,6-dimorpholin-4-yl-1,3,5-triazin-2-yl)phenyl]urea. Thus, the formulation contained about 5% by weight 1-(4-{[4-(dimethylamino)piperidin-1-yl]carbonyl}phenyl)-3-[4-(4,6-dimorpholin-4-yl-1,3, 5-triazin-2-yl)phenyl]urea and a 3.2% by weight pamoic acid. The particle size of a nanoparticle so formed as described herein above was about 92 nm.

Example 4

Formulation D with Therapeutic Agent (a) Preparation of organic stock solution: A 7 heated wt % xinafoic acid solution in benzyl alcohol was combined with PLA-PEG in a mole ratio of 16:5 with ethyl acetate was vortexed until dissolved. The therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea, was added thereto to make a final concentration of 15% by weight.

(b) Preparation of aqueous phase stock: Sodium cholate (2.75 g) was dissolved in RODI water (955.5 g) with stirring. Benzyl alcohol (40 g) was added to the aqueous sodium cholate solution and the mixture was stirred until dissolved.

(c) Formation of emulsion: The weight ratio of aqueous phase to organic phase was 5:1. The organic phase was poured into the aqueous phase which was cooled in ice water bath, and the mixture was homogenized using a hand homogenizer for 15 seconds. The coarse emulsion was fed through a high pressure homogenizer with pressure set at 10485 psi on gauge for 1 pass to form a nanoemulsion (fine emulsion).

(d) Formation of nanoparticles: The nanoemulsion was poured into a quench buffer solution consisting of anhydrous citric acid (19.2 g) in cold RODI water (1000 g) that was chilled to less than 2° C., and brought to pH 4.5 with 10 N sodium hydroxide, and the resulting solution stirred on a stir plate. To the quenched solution was added a chilled solution (less than 2° C.) of polysorbate 80 (350 g) dissolved in RODI water (650 g) with mixing.

(e) The nanoparticles were concentrated through tangential flow filtration on accordance with the procedure of Example 1.

Thus, this formulation contained the counterion xinafoic acid. It contained 1-(4-{[4-(dimethylamino)piperidin-1-yl]carbonyl}phenyl)-3-[4-(4,6-dimorpholin-4-yl-1,3,5-triazin-2-yl)phenyl]urea. The particle size of a nanoparticle so formed as described herein above was about 109 nm.

Comparative Example 1

Control Solution (a) Preparation of organic stock solution: A 7.5 wt % benzyl alcohol solution, prepared by dissolving benzyl alcohol in RODI water, was combined with PLA-PEG in a mixture having a mole ratio of 16:5 with ethyl acetate and vortexed until dissolved.

(b) Preparation of aqueous phase stock: Sodium cholate (2.75 g) was dissolved in RODI water (955.5 g) with stirring. Benzyl alcohol (40 g) was added to the sodium cholate/water solution and the mixture was stirred until dissolved.

(c) Formation of emulsion: The weight ratio of aqueous phase to organic phase was 5:1. The organic phase was poured into the aqueous phase that was cooled in ice water bath, and the mixture homogenized using a hand homogenizer for 15 seconds. The coarse emulsion was fed through a high pressure homogenizer with pressure set at 10485 psi on gauge for 1 pass to form a nanoemulsion (fine emulsion).

(d) Formation of nanoparticles: The nanoemulsion was poured into 600 g of cold RODI water (less than 2° C.) while stirring on a stir plate to form a quenched phase. (The weight ratio of quench to emulsion is 10:1). To the quenched phase was added 64.3 g of a solution of polysorbate 80 (350 g dissolved in 650 g RODI water) with mixing.

(e) Concentration of nanoparticles through tangential flow filtration (TFF): The quenched phase was concentrated using TFF with 300 kDa Pall cassette (2 membranes) to form a nanoparticle concentrate of approximately 200 mL. The nanoparticle concentrate was diafiltered with approximately 20 diavolumes of cold RODI water at less than 2° C. The volume of the diafiltered nanoparticle concentrate was reduced to minimal volume.

Comparative Example 2

Formulation B (a) Preparation of organic phase stock: Oleic acid (900 mg), trifluoroacetic acid (TFA) (273 mg) was dissolved in benzyl alcohol (8827 mg). The therapeutic agent, 1-(4-{[4-(dimethylamino)piperidin-1-yl]

carbonyl}phenyl)-3-[4-(4,6-dimorpholin-4-yl-1,3,5-triazin-2-yl)phenyl]urea (120 mg) was mixed with the oleic acid/TFA/benzyl alcohol solution and heated to 80° C. for 10 minutes to dissolve the therapeutic agent therein. Once the 1-(4-{[4-(dimethylamino)piperidin-1-yl]carbonyl}phenyl)-3-[4-(4,6-dimorpholin-4-yl-1,3,5-triazin-2-yl)phenyl]urea was dissolved, the solution was allowed to cool to room temperature. This solution was thoroughly mixed with a polymer solution of PLA-PEG in a ratio of 16 moles/5 moles (860 mg), PLA-PEG-GL (18.9 mg) and ethyl acetate (4549 mg) to form a solution.

(b) Preparation of aqueous phase stock: Sodium Cholate (4.5 g) was dissolved in RODI water (955.5 g) on a stir plate. Benzyl alcohol (40 g) was added to the sodium cholate/water solution and the mixture was stirred on a stir plate until dissolved.

(c) Formation of emulsion: The weight ratio of aqueous phase to organic phase was 5:1. The organic phase was poured into 33.4 g of the aqueous phase that was cooled in ice water bath, and the mixture homogenized using a hand homogenizer for 15 seconds. The coarse emulsion was fed through a high pressure homogenizer with pressure set at 10485 psi on gauge for 1 pass to form a nanoemulsion (fine emulsion).

(d) Formation of nanoparticles: The nanoemulsion was poured into 401.2 g of cold RODI water (less than 2° C.) while stirring on a stir plate to form a quenched phase. To the quenched phase was added 51.4 grams of a solution of polysorbate 80 (350 g dissolved in 650 g RODI water) with mixing.

(e) Concentration of nanoparticles through tangential flow filtration (TFF): The quenched phase was concentrated using TFF with 300 kDa Pall cassette (2 membranes) to form a nanoparticle concentrate of approximately 200 mL. The nanoparticle concentrate was diafiltered with approximately 20 diavolumes of cold RODI water at less than 2° C. The volume of the diafiltered nanoparticle concentrate was reduced to minimal volume.

Thus, this formulation contained 1-(4-{[4-(dimethylamino)piperidin-1-yl]carbonyl}phenyl)-3-[4-(4,6-dimorpholin-4-yl-1,3,5-triazin-2-yl)phenyl]urea and the polymers PLA-PEG (in an about 16:5 molar ratio) in a weight ratio of the therapeutic agent to polymers of about 1:14.7. It contained about 6.0% by weight 1-(4-{[4-(dimethylamino)piperidin-1-yl]carbonyl}phenyl)-3-[4-(4,6-dimorpholin-4-yl-1,3,5-triazin-2-yl)phenyl]urea, about 5.4% cholic acid, and about 1.1% by weight oleic acid.

Example 5

Formulation E with Therapeutic Agent

The procedure of Example 1 was repeated except that there was no PLA-PEG-GL polymer present. The PLA-PEG-GL polymer was replaced with 19.2 mg of PLA-PEG in a ratio of 16 mol/5 mol so that the total amount of PLA-PEG present was 850 mg.

Example 6

Formulation F with Therapeutic Agent

The procedure of Example 2 was repeated except that there was no PLA-PEG-GL polymer present. The PLA-PEG-GL polymer was replaced with 20 mg of PLA-PEG in a ratio of 16 mol/5 mol so that the total amount of PLA-PEG present was 860 mg.

Example 7

Formulation F with Therapeutic Agent

The procedure of Example 3 was repeated except that there was no PLA-PEG-GL polymer present. The PLA-PEG-GL polymer was replaced with 14.5 mg of PLA-PEG in a ratio of 16 mol/5 mol so that the total amount of PLA-PEG present was 658 mg.

Example 8

Release Profile of Formulation

Each formulation was prepared at a scale sufficient to deliver 200 mg therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea, at a concentration of >2.5 mg/mL (FORMULATION A=25 g, FORMULATION B=20 g, FORMULATION C=10 g). Nanoparticle suspensions were prepared with 30 wt % sucrose and vialed in >11 mg of therapeutic agent aliquots. Table 1 summarizes the attributes of nanoparticles prepared for this study.

TABLE 1

Summary of FORMULATION A, B, C

| Formulation | Lot Number | Therapeutic Agent Loading | Particle Size (nm) | API Released at 24 hr |
|---|---|---|---|---|
| A | 237-46 | 4% | 130 | 60% |
| B | 237-45 | 5% | 95 | 22% |
| C | 237-44 | 16% | 100 | 2% |

The three batches satisfied particle size and therapeutic agent release criteria (90-150 nm, <50% therapeutic agent released at t>2 h). With the exception of the nanoparticles of FORMULATION A, the batches also met the therapeutic agent loading criteria of >5%. Historically, the therapeutic agent loading for FORMULATION A has been on the lower limit or below the target loading threshold, so this result was not unexpected.

Figure 3:
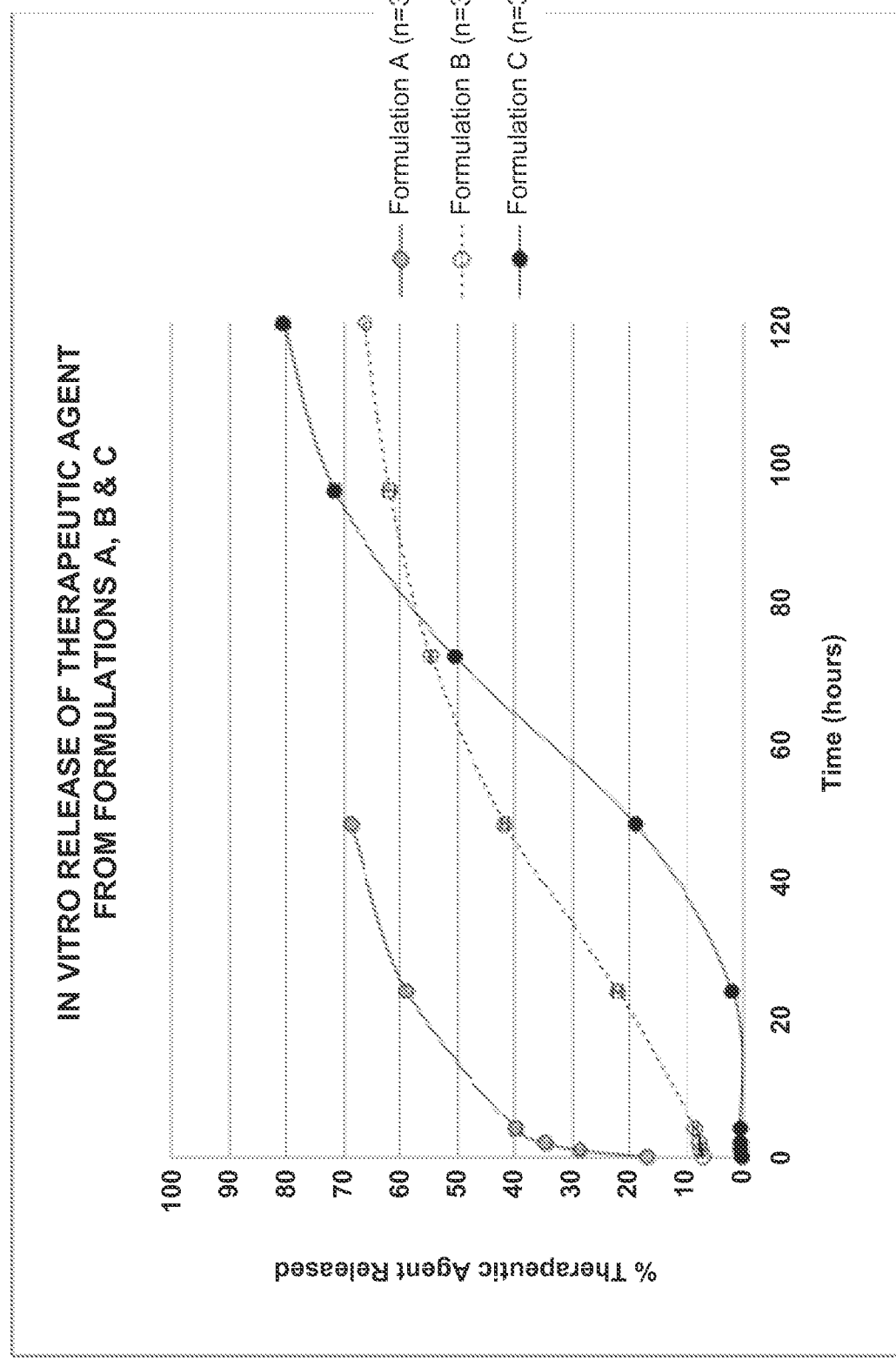
FIG. 3 depicts in vitro release profiles of nanoparticles of three formulations described herein below identified as Formulations A, B, and C, respectively, each comprising 1-(4-{[4-(dimethylamino)piperidin-1-yl]carbonyl}phenyl)-3-[4-(4,6-dimorpholin-4-yl-1,3,5-triazin-2-yl)phenyl]urea. Error bars indicate the standard deviation. Water bath temperature=37° C.

FIG. 3 shows the in vitro release curves for each batch. The in vitro release method used determines release profiles from these nanoparticles at 37° C. conditions using the centrifugal system. Samples were centrifuged at 264,000×g for 30 minutes and the supernatant was assayed for therapeutic agent concentration. Cumulative release percentage was determined by comparing the supernatant concentration with the total therapeutic agent concentration prior to centrifugation.

Figure 4:
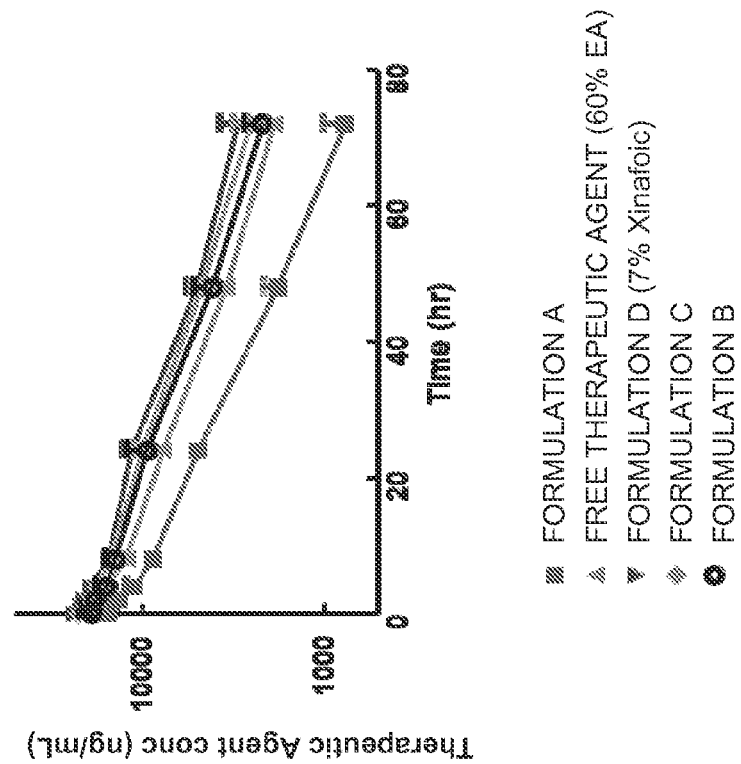
FIG. 4 depicts the pharmacokinetics of the nanoparticles of three formulations described herein and identified as Formulations A, B, and C, respectively, each comprising 1-(4-{[4-(dimethylamino)piperidin-1-yl]carbonyl}phenyl)-3-[4-(4,6-dimorpholin-4-yl-1,3,5-triazin-2-yl)phenyl]urea, in Wistar Han Rats; (a) shows the pharmacokinetics of the nanoparticle relative to free therapeutic agent, while (b) shows the same data with free therapeutic agent omitted.
Figure 4:
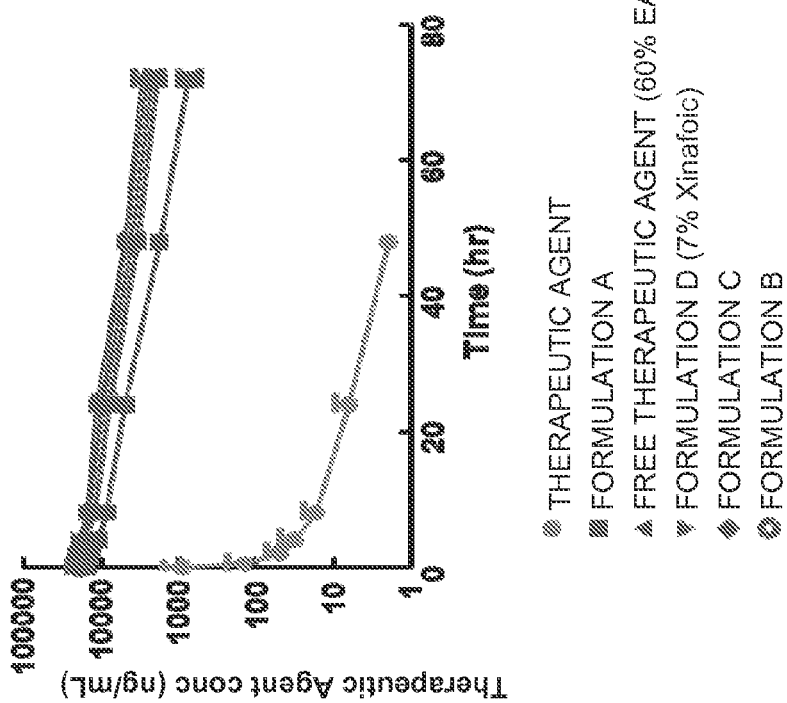

The in vitro release profile in FIG. 3 shows that the rate of the release of therapeutic agent was quantifiably distinct for each of the formulations. FIG. 4 depicts the pharmacokinetics of the therapeutic agent nanoparticles in Wistar Han Rats.

The protocol was as follows: Male Wistar Han rats (approximately six weeks in age; n=4/group) with indwelling jugular vein cannulae were dosed intravenously with a 1 mg/kg bolus of Formulation A, B, and C nanoparticles or Formulation A, B, and C nanoparticles diluted in 0.9% saline. At various times after dosing, serial blood collections were made from the jugular vein cannulae and plasma concentrations of therapeutic agent were quantitated by LC-MS/MS. FIG. 4(a) shows the pharmacokinetics of nanoparticles vs. free therapeutic agent, while (b) shows the same data with free therapeutic agent omitted.

FIG. 4(a) indicates that all three formulations A, B, and C, that were tested exhibited substantially increased retention times in the blood stream over the free API. This corresponds to increased values of AUC and $t_{1/2}$, summarized in Table 2 (TA=therapeutic agent).

The increased emulsion processing time from a 2 g batch to a 5 g batch resulted in a substantial drop in the loading of the therapeutic agent. However, it was shown that using a pH 4.5 buffered quench resulted in nearly a three-fold increase in loading of the therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea.

Figure 5:
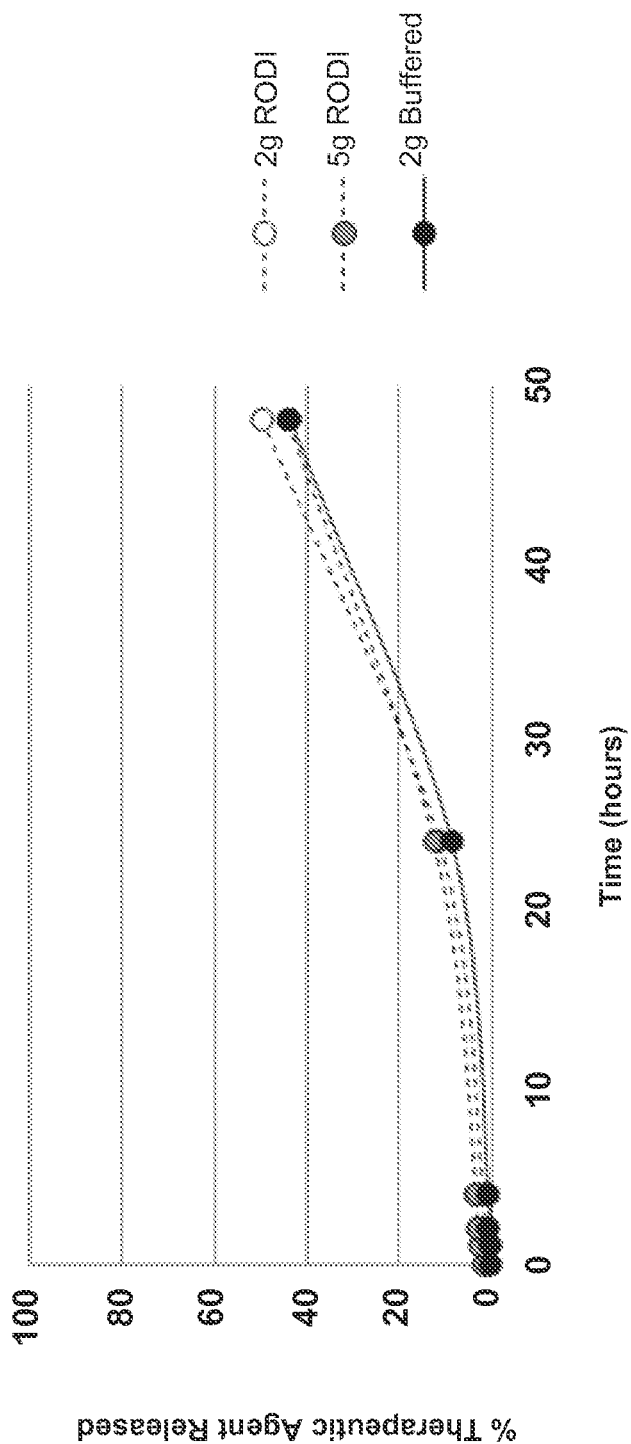
FIG. 5 depicts in vitro release profiles of Formulation A of the drug 1-(4-{[4-(dimethylamino)piperidin-1-yl]carbonyl}phenyl)-3-[4-(4,6-dimorrpholin-4-yl-1,3,5-triazin-2-yl)phenyl]urea. Error bars indicate the standard deviation. Water bath temperature=37° C.

The in vitro release method was used to determine the release profiles from these nanoparticles at 37° C. conditions using the centrifugal system. Samples were centrifuged at 264,000×g for 30 minutes and the supernatant was assayed for therapeutic agent concentration. Cumulative release percentage was determined by comparing the supernatant concentration with the total therapeutic agent concentration prior to centrifugation. FIG. 5 shows the in vitro release profile was unaffected by the use of a buffered quench.

TABLE 2

Summary of $AUC_{all}$ and $t_{1/2}$ data for FORMULATION A, B & C nanoparticles tested.

| Parameter | TA | Formulation A | 60% EA | 7% Xinafoic Acid | Formulation C | Formulation B |
|---|---|---|---|---|---|---|
| $AUC_{all}$ (hr · ng/mL) | 919.5 | 312,972 | 485,188 | 653,749 | 601,768 | 550,539 |
| $t_{1/2}$ (hr) | 13.2 | 17.7 | 23.8 | 25.1 | 23.8 | 23.7 |

Example 9

Release Profile for Formulation C

FORMULATION C was again prepared as in Example 3 using the traditional batch process at the 2 g and 5 g scale. An additional 2 g batch of Formulation C was prepared using a 50 mM citric acid buffer titrated to pH 4.5 with sodium hydroxide to promote potential ion pairing. This pH was chosen because it was in between the $pK_a$ of pamoic acid (~2.5) and the first $pK_a$ of 1-(4-{[4-(dimethylamino)piperidin-1-yl]carbonyl}phenyl)-3-[4-(4,6-dimorpholin-4-yl-1,3,5-triazin-2-yl)phenyl]urea (~6.7). Table 3 summarizes the particle attributes for these small-scale batches:

TABLE 3

Effect of using pH 4.5 50 mM citric acid buffer for the quench medium in Formulation C.

| Batch | Lot Number | Therapeutic Agent Loading | Size (nm) |
|---|---|---|---|
| 2 g RODI Quench | 237-34-1 | 4.48% | 101 |
| 5 g RODI Quench | 237-34-2 | 2.43% | 98 |
| 2 g Buffered Quench | 237-34-3 | 13.18% | 92 |

Example 10

Determination of Particle Attributes for Formulation C

Two 10 g batches of Formulation C were prepared with 100 mM citric acid buffer quench titrated to pH 4.5, each by pooling five 2 g batches to avoid the effects of processing time on drug loading of the therapeutic agent, 1-(4-{[4-(dimethylamino)piperidin-1-yl]carbonyl}phenyl)-3-[4-(4,6-dimorpholin-4-yl-1,3,5-triazin-2-yl)phenyl]urea. Table 4 summarizes the particle attributes for these batches.

TABLE 4

Particle attributes for FORMULATION C batches utilizing pH 4.5 citric acid buffer quench.

| Lot Number | Description | Target API Loading | Organic Phase Solids | Formulation C Loading | Particle Size (nm) | Surfactant |
|---|---|---|---|---|---|---|
| 237-34-3 | 8 wt % TFA 7.5 wt water in BA, 1:1 pamoic to therapeutic agent, 20:80 (BA + DMSO):EA, 50 mM citric acid quench, pH 4.5 | 22% | 10% | 13.18% | 92 | Brij, 0.02 wt % |
| 237-36 | 8 wt % TFA 7.5 wt % water in BA, 1:1 pamoic to therapeutic agent, 20:80 (BA + DMSO):EA, 100 mM citric acid quench, pH 4.5 | 22% | 10% | 18.25% | 100 | Brij, 0.02 wt % |

TABLE 4-continued

Particle attributes for FORMULATION C batches utilizing pH 4.5 citric acid buffer quench.

| Lot Number | Description | Target API Loading | Organic Phase Solids | Formulation C Loading | Particle Size (nm) | Surfactant |
|---|---|---|---|---|---|---|
| 237-44 | 8 wt % TFA 7.5 wt % water in BA, 1:1 pamoic to therapeutic agent, 20:80 (BA + DMSO):EA, 100 mM citric acid quench, pH 4.5, GL Targeted | 22% | 10% | 16.30% | 100 | Brij, 0.02 wt % |

BA = benzyl alcohol
EA = ethyl alcohol

Figure 6:
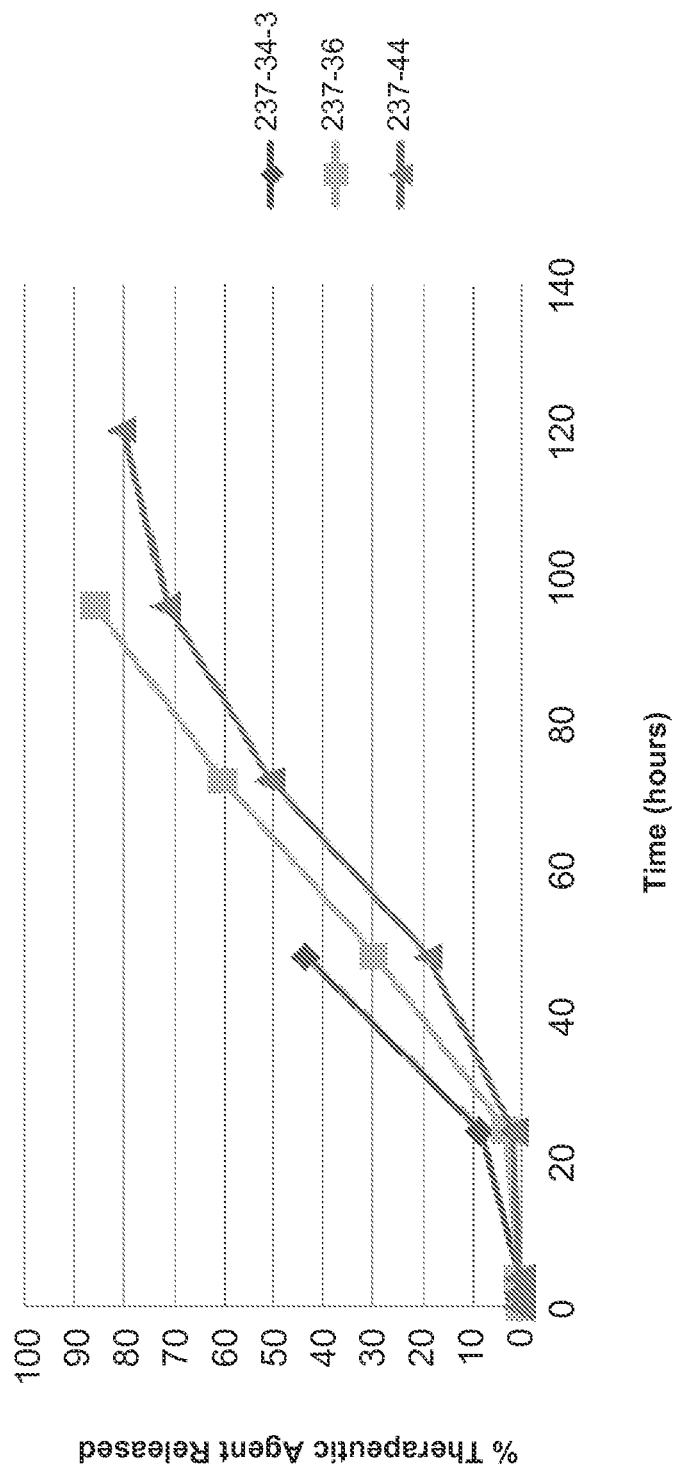
FIG. 6 depicts in vitro release profiles of Formulation C of the drug 1-(4-{[4-(dimethylamino)piperidin-1-yl]carbonyl}phenyl)-3-[4-(4,6-dimorpholin-4-yl-1,3, 5-triazin-2-yl)phenyl]urea using pH 4.5 citric acid buffered quench.

The in vitro release profiles were conducted as follows; the in vitro release method was used to determine the release profiles from these nanoparticles at 37° C. conditions using the centrifugal system. Samples are centrifuged at 264,000×g for 30 minutes and the supernatant was assayed for therapeutic agent concentration. Cumulative release percentage was determined by comparing the supernatant concentration with the total therapeutic agent concentration prior to centrifugation. The results are shown in FIG. 6.

From the investigations, it was ascertained that maximum therapeutic agent loading in the formulation C was achieved at pH 4.5. Without wishing to be bound, it is believed that this may be attributed to the fact that ion pairing between the therapeutic agent and the counter ion is encouraged when the pH of the solution is below the $pK_a$ of the protonated therapeutic agent drug and above the $pK_a$ of the acidic molecule (pamoic acid). This effect is believed to be theoretically maximized when the largest fraction of both species are in their ionized state.

Example 11

MDAMB361 Xenograft Scheduling Study 1-(4-{[4-(Dimethylamino)Piperidin-1-Yl]Carbonyl}Phenyl)-3-[4-(4,6-Dimorpholin-4-yl-1,3,5-Triazin-2-Yl)Phenyl]Urea Nanoparticles Q4D Versus Q8D Female SCID/bg mice at age around 6 weeks were obtained from Charles River Laboratories (Wilmington, Mass.). Animals were maintained under clean room conditions in sterile filter top cages with Alpha-Dri bedding and housed on HEPA-filtered ventilated racks. Animals received sterile rodent chow and water ad libitum. All of the procedures were conducted in accordance with the Institute for Laboratory Animal Research Guide for the Care and Use of Laboratory Animals and with Pfizer Animal Care and Use Committee guidelines.

Three to four days prior to tumor cell inoculation, the animals were implanted with a 0.36 mg, 60-d release 17β-estradiol pellet (Innovative Research of America). The MDA-MB-361 cells which were harvested at 80-90% confluence and viability above 80-90% (NS) were supplemented with 50% Matrigel (BD Biosciences, San Jose Calif.) to facilitate tumor take. Cells (5×106 in 200 μL) were implanted subcutaneously (S.C.) into the hind flank region of the mouse and allowed to grow to the designated size prior to the administration of compound for each experiment. Tumor size was determined by measurement with an electronic calipers and tumor volume was calculated as the product of its length×width²×0.5. When tumor volumes reached an average of 250 mm³, mice were randomized for treatment groups including vehicle control group with intravenous (i.v.) injections of the corresponding drug at 10 mL/kg volume on an every four-day (Q4D) or eight-day (Q8D) schedule. Animals were treated with 5 or 10 mg/kg 1-(4-{[4-(dimethylamino)piperidin-1-yl]carbonyl}phenyl)-3-[4-(4, 6-dimorpholin-4-yl-1,3,5-triazin-2-yl)phenyl]urea or 25 mg/kg of the Formulation B nanoparticle at each injection.

Figure 7:
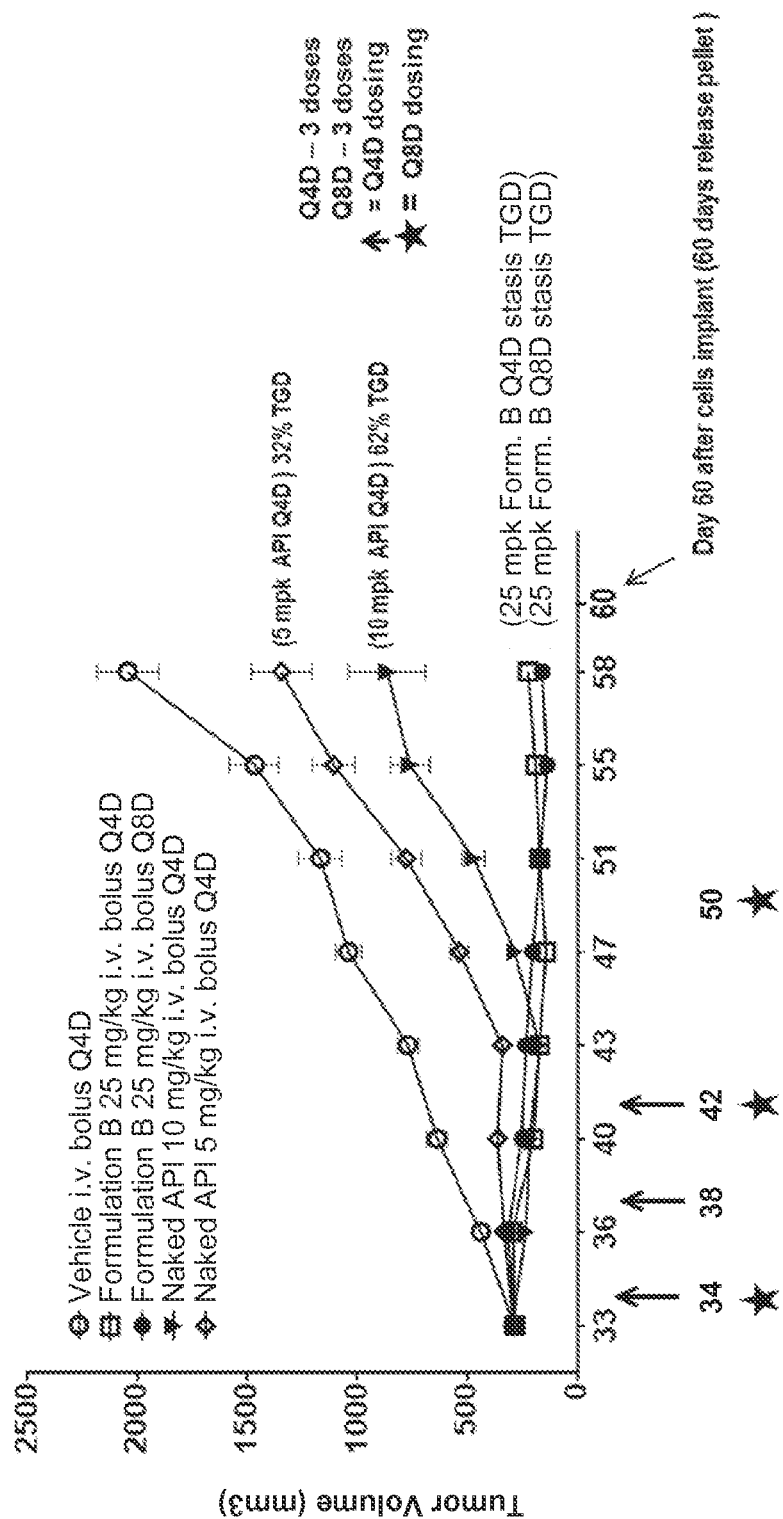
FIG. 7 depicts a MDAMB361 xenograft scheduling study in female SCID/bg mice dosed with Formulation B nanoparticles or 1-(4-{[4-(dimethylamino)piperidin-1-yl]carbonyl}phenyl)-3-[4-(4,6-dimorpholin-4-yl-1,3,5-triazin-2-yl)phenyl]urea (naked API) once every 8 days versus once every 4 days.

FIG. 7 shows that Formulation B nanoparticles dosed every 8 days has similar efficacy as once every 4 days and that Formulation B nanoparticles may afford a 2 week dosing frequency in the clinic.

Example 12

MDAMB361 Tumor Growth Inhibition and Tumor Growth Delay Study

Female SCID/bg mice at age around 6 weeks were obtained from Charles River Laboratories (Wilmington, Mass.). Animals were maintained under clean room conditions in sterile filter top cages with Alpha-Dri bedding and housed on HEPA-filtered ventilated racks. Animals received sterile rodent chow and water ad libitum. All of the procedures were conducted in accordance with the Institute for Laboratory Animal Research Guide for the Care and Use of Laboratory Animals and with Pfizer Animal Care and Use Committee guidelines.

Three to four days prior to tumor cell inoculation, the animals were implanted with a 0.36 mg, 60-d release 17β-estradiol pellet (Innovative Research of America). The MDA-MB-361 cells which were harvested at 80-90% confluence and viability above 80-90% (NS) were supplemented with 50% Matrigel (BD Biosciences, San Jose Calif.) to facilitate tumor take. Cells (5×106 in 200 μL) were implanted subcutaneously (S.C.) into the hind flank region of the mouse and allowed to grow to the designated size prior to the administration of compound for each experiment. Tumor size was determined by measurement with an electronic calipers and tumor volume was calculated as the product of its length×width²×0.5. When tumor volumes reached an average of 250 mm³, mice were randomized for treatment groups including vehicle control group with intravenous (i.v.) injections of the corresponding drug at 10 mL/kg volume on an every four-day (Q4D) schedule for 4 doses. Post the 4th dose, animals were further monitored for tumor growth delay. Animals were treated with 10 mg/kg 1-(4-{[4-(dimethylamino)piperidin-1-yl]carbonyl}phenyl)-3-[4-(4,6-dimorpholin-4-yl-1,3,5-triazin-2-yl)phenyl]urea; 2, 10, or 25 mg/kg of the Formulation A or B nanoparticles; or 10 or 25 mg/kg of the Formulation C nanoparticles at each injection.

Figure 8A:
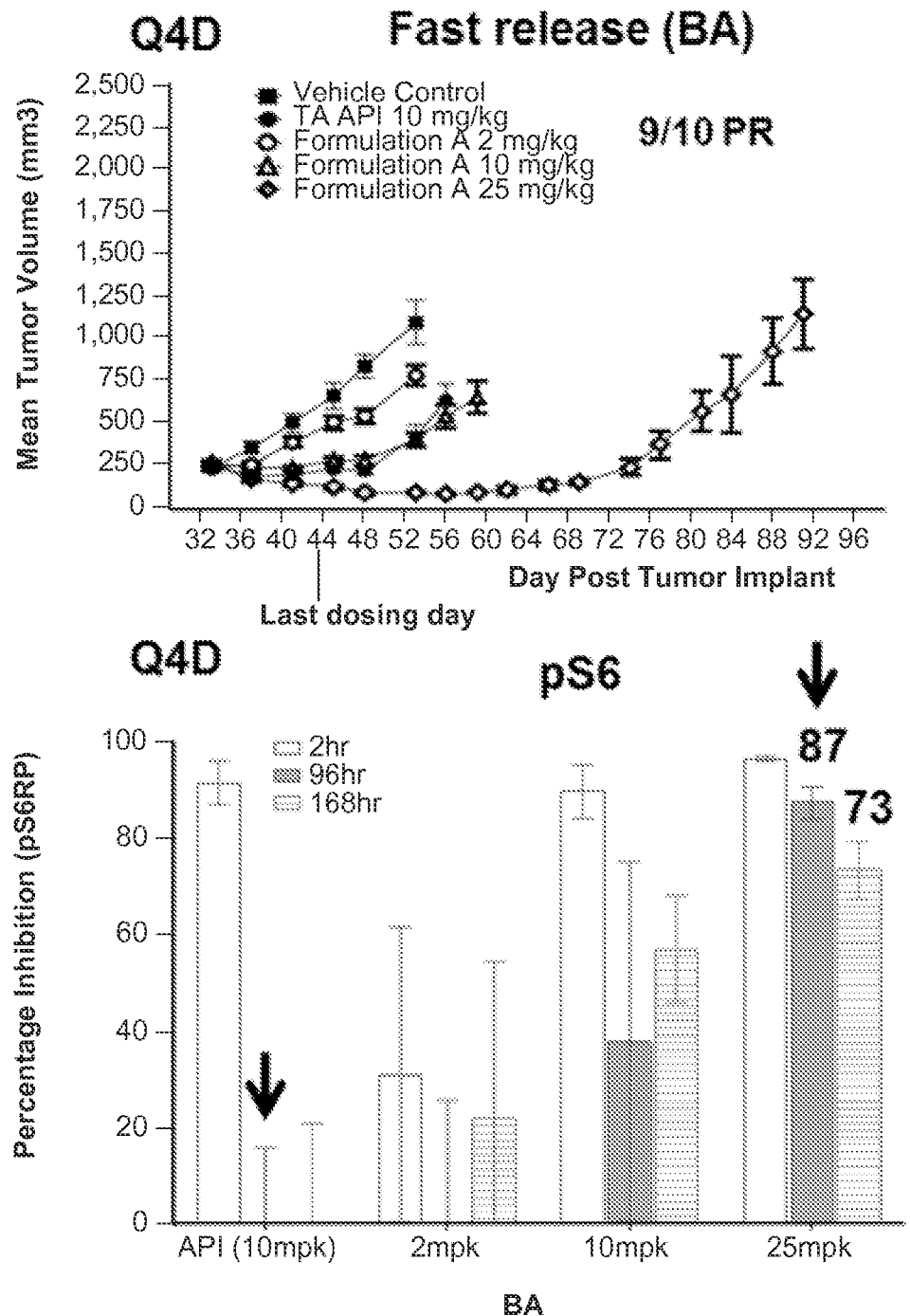
FIGS. 8A, 8B, and 8C depict a MDAMB361 xenograft scheduling study in female SCID/bg mice dosed with Formulation A, B, or C nanoparticles or naked API once every 8 days versus once every 4 days, and in vivo pS6 modulation studies with Formulation A, B, or C nanoparticles or 1-(4-{[4-(dimethylamino)piperidin-1-yl]carbonyl}phenyl)-3-[4-(4,6-dimorpholin-4-yl-1,3,5-triazin-2-yl)phenyl]urea (naked API). TA=therapeutic agent.
Figure 8B:
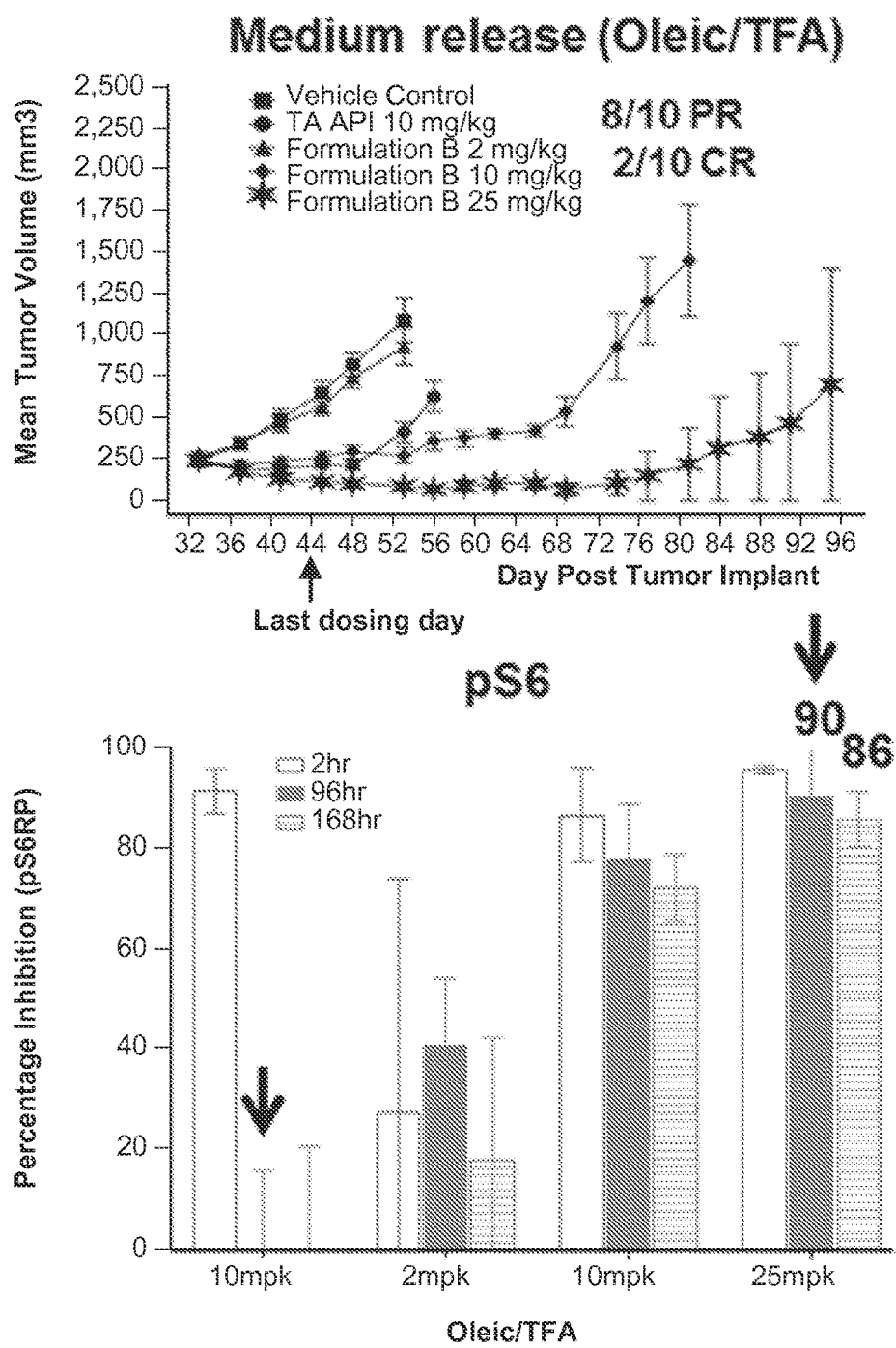
Figure 8C:
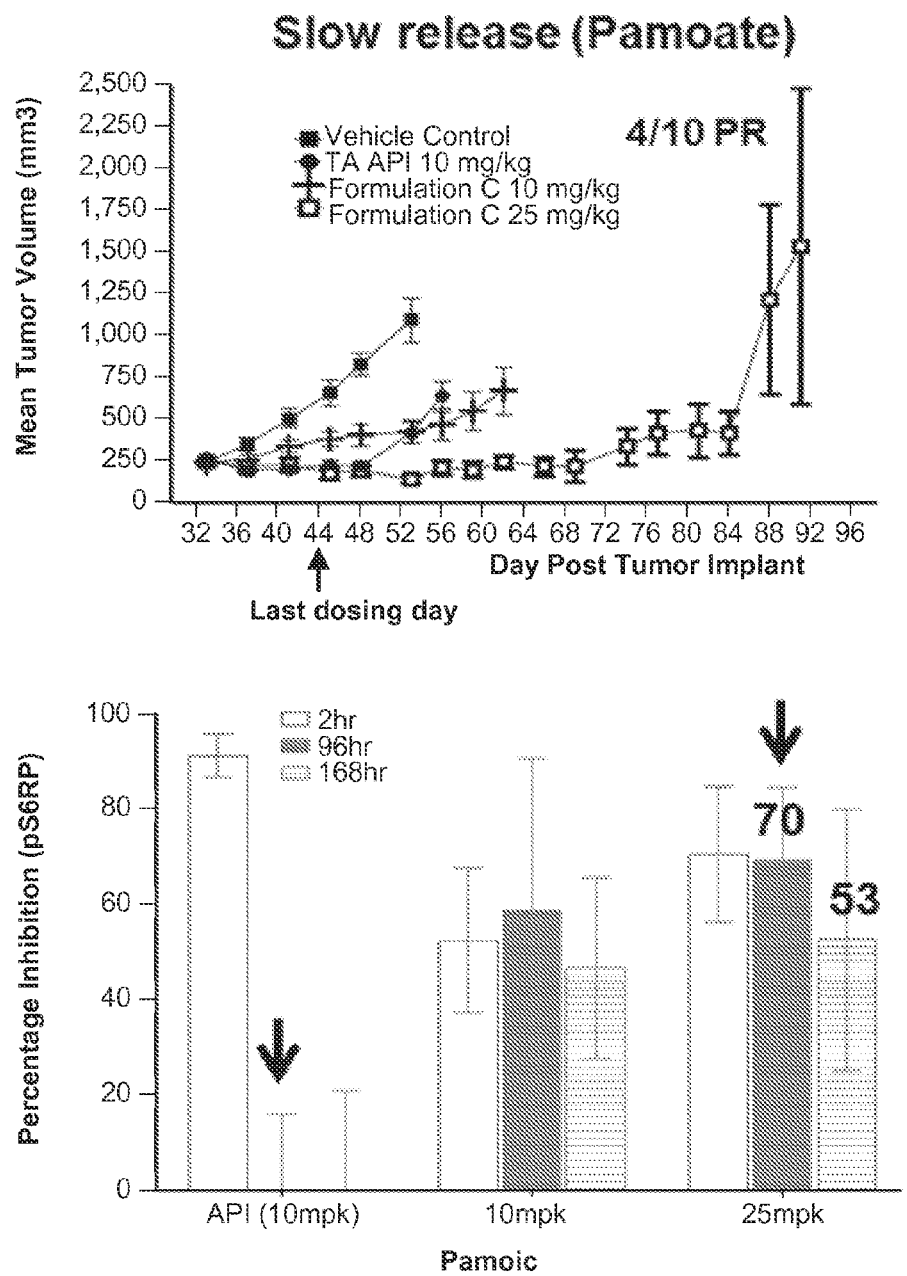

FIGS. 8A, 8B, and 8C show that Formulation B nanoparticles and Formulation C nanoparticles inhibit tumor growth with improved efficacy versus 1-(4-{[4-(dimethylamino)piperidin-1-yl]carbonyl}phenyl)-3-[4-(4,6-dimorpholin-4-yl-1,3, 5-triazin-2-yl)phenyl]urea (naked API) and Formulation A nanoparticles.

Example 13

WM266-4 Model Tumor Growth Inhibition Study

Female nu/nu mice at age around 8 weeks were obtained from Charles River Laboratories (Wilmington, Mass.). Animals were maintained under clean room conditions in sterile filter top cages with Alpha-Dri bedding and housed on HEPA-filtered ventilated racks. Animals received sterile rodent chow and water ad libitum. All of the procedures were conducted in accordance with the Institute for Laboratory Animal Research Guide for the Care and Use of Laboratory Animals and with Pfizer Animal Care and Use Committee guidelines.

The WM266-4 cells which were harvested at 80-90% confluence and viability above 80-90% (NS) were supplemented with 50% Matrigel (BD Biosciences, San Jose Calif.) to facilitate tumor take. Cells ($2\times10^6$ in 200 µL) were implanted subcutaneously (S.C.) into the hind flank region of the mouse and allowed to grow to the designated size prior to the administration of compound for each experiment. Tumor size was determined by measurement with an electronic calipers and tumor volume was calculated as the product of its length$\times$ width$^2\times0.5$. When tumor volumes reached an average of 400 mm$^3$, mice were randomized for treatment groups including vehicle control group with oral daily (QD) of PF-0192513-00-0004 (PD-901) and/or intravenous (i.v.) injections of the nanoparticle drugs, B and C at 10 mL/kg volume on an every four-day (Q4D) schedule for 4 doses. Dosing and drug are described in the figure legends. Animals were treated with 10 mg/kg 1-(4-{[4-(dimethylamino)piperidin-1-yl]carbonyl}phenyl)-3-[4-(4,6-dimorpholin-4-yl-1,3,5-triazin-2-yl)phenyl]urea or 10, 25, or 50 mg/kg of the Formulation B or C nanoparticles at each injection.

Figure 9:
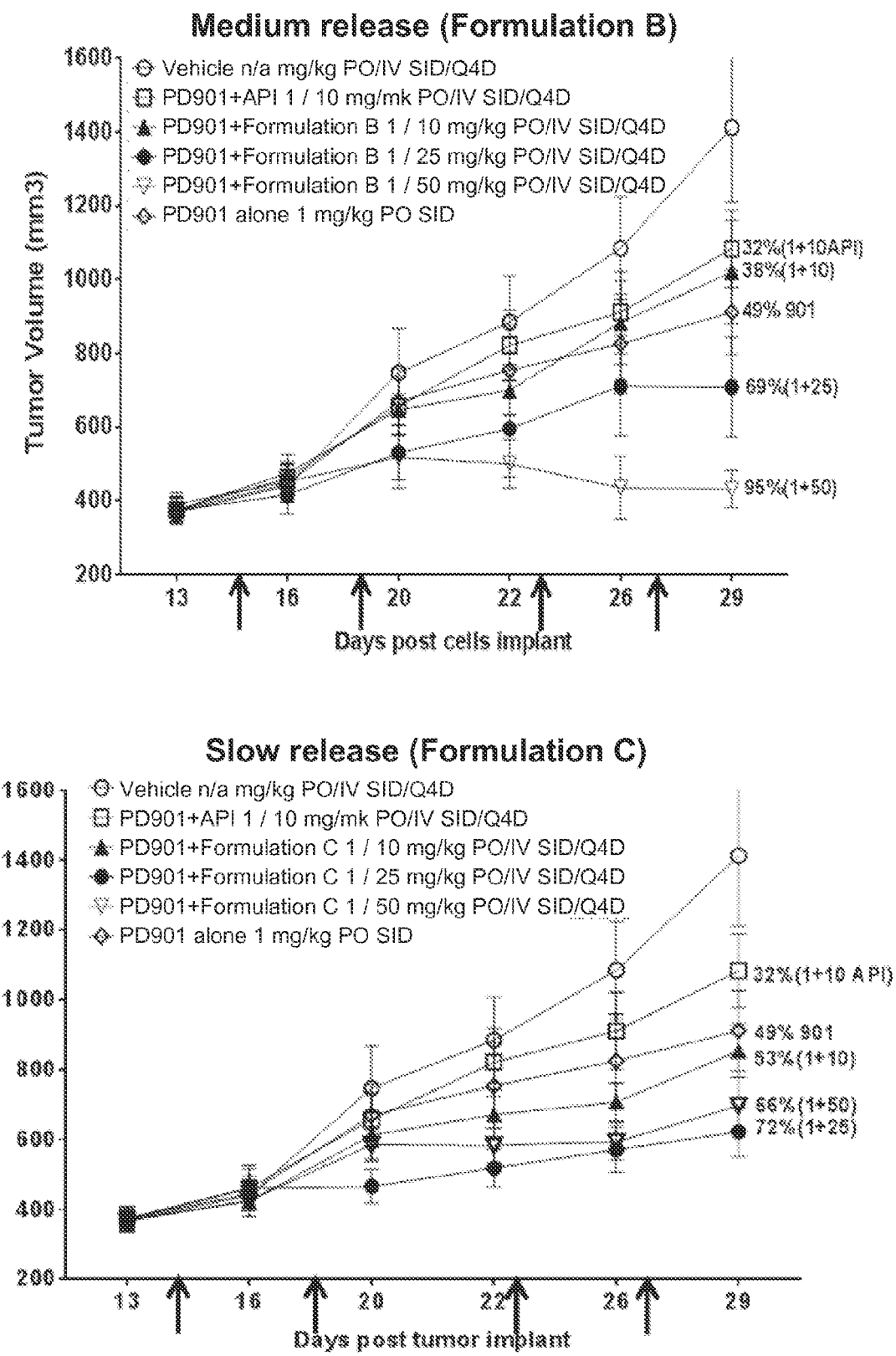
FIG. 9 depicts a WM266-4 model tumor growth inhibition study with female nu/nu mice treated with Formulation B or C nanoparticles or 1-(4-{[4-(dimethylamino)piperidin-1-yl]carbonyl}phenyl)-3-[4-(4,6-dimorpholin-4-yl-1,3,5-triazin-2-yl)phenyl]urea (naked API). TA=therapeutic agent.

FIG. 9 illustrates that Formulation C nanoparticles produce greater tolerability and efficacy than Formulation B nanoparticles or 1-(4-{[4-(dimethylamino)piperidin-1-yl] carbonyl}phenyl)-3-[4-(4,6-dimorpholin-4-yl-1,3,5-triazin-2-yl)phenyl]urea (naked API).

Example 14

In Vivo Target Modulation Studies with Nanoparticles

In vivo target modulation studies were conducted to determine the effects of treatment with the Formulation A, B, and C nanoparticles on the phosphorylation of S6 on S235/S236 and AKT on S473 and T308 by ELISA. Resected fresh tumors were ground into fine powder using metal Martor and granite pestle under liquid nitrogen. The tumor powder was stored at −80° C. until preparation of tumor lysates for ELISA assay. Briefly, an aliquot (50 mg) of tumor powder was put into pre-cold 2 mL glass martor tube, 500 µl cold lysis buffer [20 mM Tris-HCl (pH 7.5), 150 mM NaCl, 1.0 mMNa$_2$EDTA, 1 mM EGTA, 1% NP-40, 1% sodium deoxycholate, 2.5 mM sodium pyrophosphate, 1 mM β-glycerophosphate, 1 mM Na$_3$VO$_4$, 1 µg/ml leupeptin, 1 mM PMSF, 1× protease/phosphatase inhibitor cocktail] was added, the tube was embedded in wet ice, and samples were homogenized at speed 6 for 30 seconds by using a tissue homogenizer. Samples were collected and snap frozen on dry ice and thawed on wet ice. Repeated freeze-thaw cycle, then centrifuged samples in a cold refrigerated Eppendorf centrifuge at 13,000 rpm for 10 minutes. Supernatant was collected and centrifuged again. The total and phosphoAKT (S473 and T308) and the total and phosphoS6 protein levels in tumor lysates were determined by ELISA. The extent of phosphorylation in tumors resected from treated animals was compared with that in tumors resected from vehicle-treated animals at the same time point.

FIGS. 8A, 8B, and 8C show that Formulation B nanoparticles and Formulation C nanoparticles inhibit pS6 with improved efficacy versus 1-(4-{[4-(dimethylamino)piperidin-1-yl]carbonyl}phenyl)-3-[4-(4,6-dimorpholin-4-yl-1,3, 5-triazin-2-yl)phenyl]urea (naked API) and Formulation A nanoparticles, and demonstrate persistent target modulation observed up to day 7 post-dose.

Example 15

Analysis of Glucose and Insulin Levels after Nanoparticle Treatment

Glucose: In mouse or rat studies, approximately 100 µL plasma (EDTA as anticoagulant) was used for assessment of glucose content based on an enzymatic assay as published by Slein (Bergmeyer H U, ed. Slein M W. *Methods of Enzymatic Analysis*. New York, N.Y.: Academic Press; 1974: 1196-1201.), using hexokinase and glucose-6-phosphate dehydrogenase enzymes. Plasma glucose was measured with Advia® 120 Glucose Hexokinase_3 (GLUH_3) system with Automated Hematology Analyzer (Siemens Healthcare Diagnostics Inc., Tarrytown, N.Y.). The Advia Chemistry Glucose Hexokinase_3 (GLUH_3) assay used a two-component reagent. Plasma sample was added to Reagent 1, which contained the buffer, ATP, and NAD. Absorbance readings of the sample in Reagent 1 were taken and used to correct for interfering substances in the sample. Reagent 2 (the buffer, ATP, NAD, Hexokinase, and G6PD) was added, which initiated the conversion of glucose and the development of absorbance at 340/410 nm. The difference between the absorbance in Reagent 1 and Reagent 2 was proportional to the glucose concentration.

Insulin: In mouse or rat studies, approximately 20 µL plasma (EDTA as anticoagulant) was used for assessment of insulin content. The insulin assay was a Sandwich ELISA based using Rat/Mouse Insulin ELISA Kit acquired from EMD Millipore Corporation (St. Charles, Missouri). The assay procedure was as follows: 1) capture of insulin molecules from plasma samples to the wells of a microtiter plate coated by pre-titered amount of a monoclonal mouse anti-rat insulin antibodies and the binding of biotinylated polyclonal antibodies to the captured insulin, 2) wash away unbound materials from samples, 3) bind horseradish peroxidase to the immobilized biotinylated antibodies, 4) wash away free enzyme conjugates, and 5) quantify immobilized antibody-enzyme conjugates by monitoring horseradish peroxidase activities in the presence of the substrate 3,3',5,5'-tetramethylbenzidine. The enzyme activity was measured spectrophotometrically by the increased absorbance at 450 nm, which was directly proportional to the amount of captured insulin in the plasma sample. The plasma insulin concentration was calculated by interpolation from a reference curve generated in the same assay with reference standards of known concentrations of rat or mouse insulin.

Figure 10:
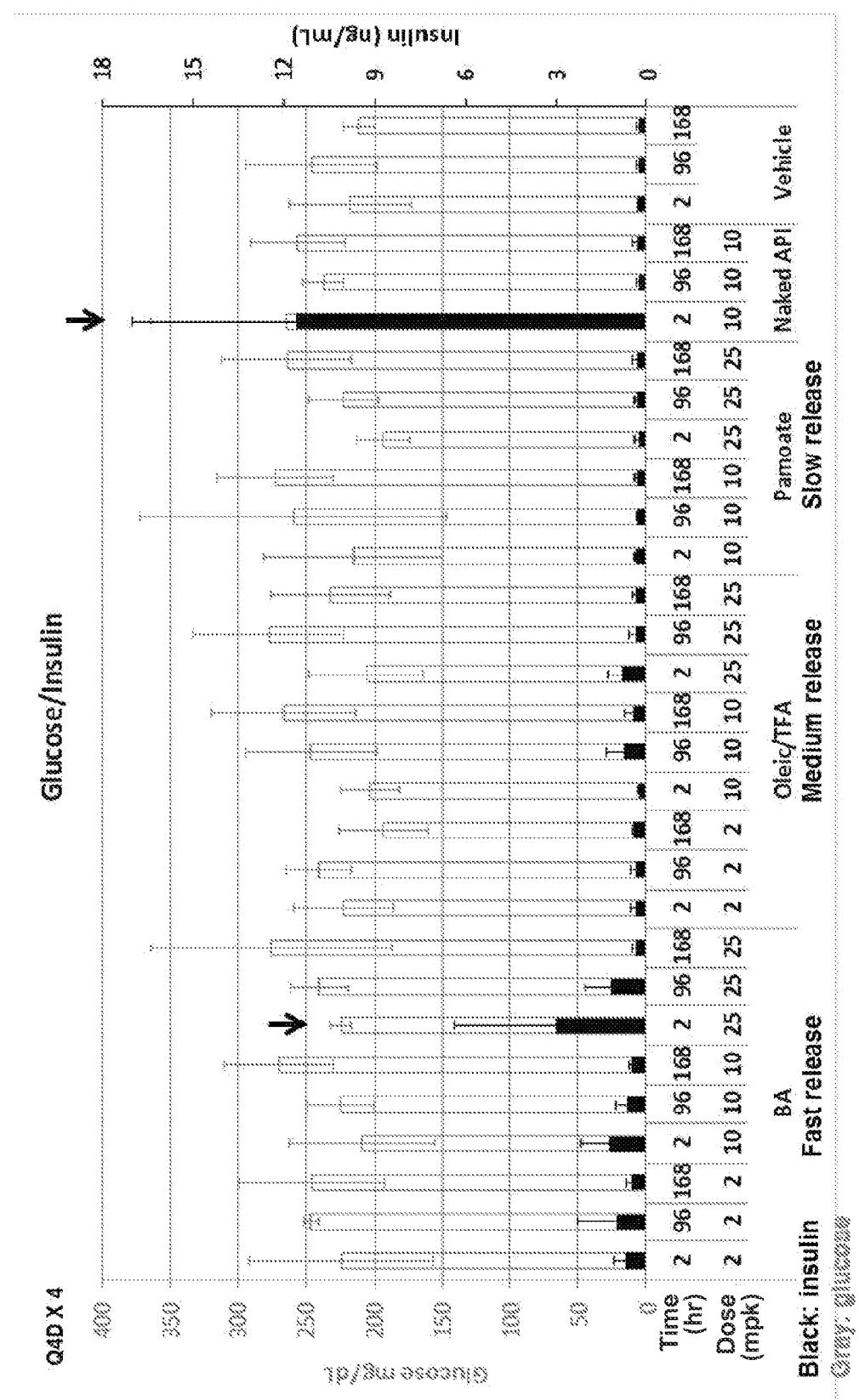
FIG. 10 depicts an analysis of glucose and insulin levels in mice or rats after treatment with Formulation B or C nanoparticles or 1-(4-{[4-(dimethylamino)piperidin-1-yl]carbonyl}phenyl)-3-[4-(4,6-dimorpholin-4-yl-1,3,5-triazin-2-yl)phenyl]urea (naked API).

FIG. 10 illustrates that Formulation B and C nanoparticles may have an improved safety profile over the 1-(4-{[4-(dimethylamino)piperidin-1-yl]carbonyl}phenyl)-3-[4-(4,6-dimorpholin-4-yl-1,3,5-triazin-2-yl)phenyl]urea (naked API).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating cancer, wherein said cancer is selected from breast cancer and prostate cancer, in a subject in need thereof, comprising administering to the subject a therapeutically effective amount of a therapeutic nanoparticle; wherein said therapeutic nanoparticle comprises:
    a therapeutic agent selected from the group consisting of 1-(4-{[4-(dimethylamino)piperidin-1-yl]carbonyl}phenyl)-3-[4-(4,6-dimorpholin-4-yl-1,3,5-triazin-2-yl)phenyl]urea and pharmaceutically acceptable salt thereof;
    a polymer selected from the group consisting of diblock poly(lactic) acid-poly (ethylene)glycol (PLA-PEG) copolymer, diblock poly(lactic acid-co-glycolic acid)-poly (ethylene)glycol (PLGA-PEG) copolymer, and combinations thereof; and
    a substantially hydrophobic acid selected from the group consisting of dioctyl sulfosuccinic acid, 1-hydroxy-2-naphthoic acid, dodecylsulfuric acid, naphthalene-1,5-disulfonic acid, naphthalene-2-sulfonic acid, pamoic acid, undecanoic acid, and combinations thereof;
    wherein the substantially hydrophobic acid and the therapeutic agent form a hydrophobic ion pair that is encapsulated in the therapeutic nanoparticle;
    wherein the hydrophobic ion pair is dispersed throughout a polymeric matrix comprising the polymer; and
    wherein PLA-PEG-GL is additionally present, wherein targeting ligand GL has the following structure:

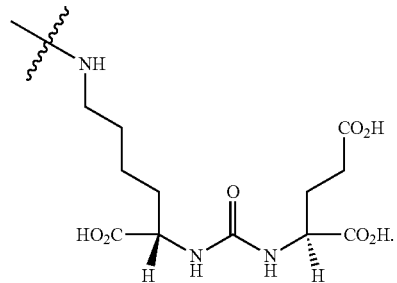 [SMILES: *NCCCC[C@H](NC(=O)N[C@@H](CCC(=O)O)C(=O)O)C(=O)O]

2. The method of claim 1, wherein the cancer is breast cancer.

3. The method of claim 1, wherein the cancer is prostate cancer.

* * * * *